(12) United States Patent  
Chan et al.

(10) Patent No.: US 8,980,848 B2
(45) Date of Patent: Mar. 17, 2015

(54) FLAVONOID DIMERS AND THEIR USE

(75) Inventors: Tak-Hang Chan, Toronto (CA); Larry Ming-Cheung Chow, Kowloon (HK); Kin-Fai Chan, Kowloon (HK); Iris Lai King Wong, Kowloon (HK)

(73) Assignee: The Hong Kong Polytechnic University, Kowloon, Hong Kong (CN)

( * ) Notice: Subject to any disclaimer, the term of this patent is extended or adjusted under 35 U.S.C. 154(b) by 118 days.

(21) Appl. No.: 13/695,697

(22) PCT Filed: May 3, 2011

(86) PCT No.: PCT/CA2011/000517
§ 371 (c)(1),
(2), (4) Date: Nov. 1, 2012

(87) PCT Pub. No.: WO2011/137516
PCT Pub. Date: Nov. 10, 2011

(65) Prior Publication Data
US 2013/0045935 A1 Feb. 21, 2013

Related U.S. Application Data

(60) Provisional application No. 61/330,423, filed on May 3, 2010.

(51) Int. Cl.
*A61K 31/352* (2006.01)
*C07D 311/30* (2006.01)
*C07D 405/14* (2006.01)

(52) U.S. Cl.
CPC ............ *C07D 311/30* (2013.01); *C07D 405/14* (2013.01)
USPC ........................................................ 514/27

(58) Field of Classification Search
None
See application file for complete search history.

(56) References Cited

U.S. PATENT DOCUMENTS

2009/0197943 A1 8/2009 Chan et al.

FOREIGN PATENT DOCUMENTS

| CA | 2652617 A1 | 11/2007 |
| WO | WO 2007/135592 A1 | 11/2007 |

OTHER PUBLICATIONS

Jin Z. H. A. O., Huan-Xu, X. I. E., Hong-Yu, L. I. U., HongXia, M. A., Song-Qiang, X. I. E., & Chao-Jie, W. A. N. G. (2010). Synthesis and Cytotoxicity of N, N-Bis (8-flavonmethyl) geranylamine Derivatives. Chinese Journal of Applied Chemistry, 4, 006.*
Jerzmanowska, Zofia; Jurkowska-Kowalczyk, Ewa, Quercetin Mannich bases, Roczniki Chemii (1970), 44(7-8), 1395-401.*
Wu, E. S. C.; Cole, T. E.; Davidson, T. A.; Blosser,J. C.; Borrelli, A. R.; Kinsolving, C. R.; Milgate, T.E.; Parker, R. B., Flavones. 1. Synthesis and antihypertensive activity of (3-phenylflavonoxy)propanolamines without b-adrenoceptor antagonism, Journal of Medicinal Chemistry (1987), 30(5), 788-92.*
International Search Report (PCT/ISA/210) Issued on Aug. 15, 2011, by the Canadian Patent Office as the International Searching Authority for International Application No. PCT/CA2011/000517.

* cited by examiner

*Primary Examiner* — Shaojia Anna Jiang
*Assistant Examiner* — Dale R Miller
(74) *Attorney, Agent, or Firm* — Buchanan Ingersoll & Rooney PC

(57) ABSTRACT

This invention relates to bis-flavonoid compounds, their synthesis and use for inhibiting multidrug resistance in chemotherapy and protozoan infection, wherein the bis-flavonoids compounds have the formula:

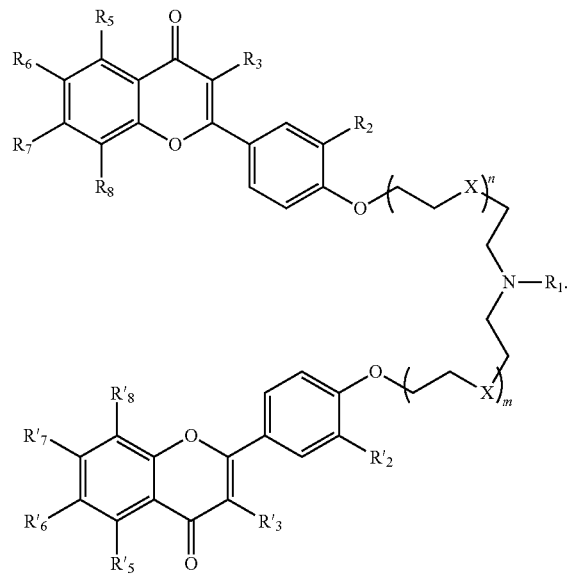

23 Claims, 4 Drawing Sheets

FLAVONOID DIMERS AND THEIR USE

CROSS-REFERENCE TO RELATED APPLICATION

This application incorporates by reference U.S. 61/330,423 from which it also claims priority.

FIELD OF THE INVENTION

This invention relates to flavonoid compounds, their synthesis and use for inhibiting multidrug resistance in chemotherapy and protozoan infection.

BACKGROUND OF THE INVENTION

Multidrug resistance (MDR) is a limiting factor to clinical outcome of chemotherapy. One such resistance mechanism is that mediated by the overexpression of drug efflux transporters such as permeability-glycoprotein (P-gp) and Multidrug resistance protein 1 (MRP1), also called ABCC1 and other proteins in the ABCG2 family. These protein transporters drive out diverse anticancer agents, resulting in lowered intracellular concentration of drug. Unlike P-glycoprotein, MRP1 pumps hydrophilic drugs either conjugated (e.g. glucuronate, sulfate) or unconjugated. The discovery of chemosensitizing or modulating agents against P-gp has attracted interest from both academia and industry. The calcium channel blocker Verapamil was one of the first compounds reported to reverse resistance by inhibiting P-gp-mediated drug efflux (Tsuruo et al., *Cancer Res* 1981, 41, 1967-1972). Since then, there is a considerable body of data suggesting that MDR due to P-gp can be effectively modulated by a range of compounds including dexverapamil, dexniguldipine, PSC 833 (Twentyman, P. R. et al. *Eur J Cancer* 1991, 27, 1639-1642) and VX-710. These second generation MDR modulators have shown encouraging results, but their clinical utility is limited by reportedly unpredictable drug-drug interaction (Lum, B. L et al. *Hematol Oncol Clin North Am* 1995, 9, 319-336). Third generation MDR modulators including zosuquidar LY335979, tariquidar XR9576, laniquidar R101933, the acridonecarboxamide GF120918 and the substituted diarylimidazole ONT-090 have been developed in effort to overcome the limitations of second generation compounds.

Flavonoids represent a promising class of compounds for modulating MDR, in part because they have generally low toxicity. Chrysin, quercetin, kaempferol and dehydrosilybin are reported to bind to the NBD2 cytosolic domain of mouse P-gp (Di Pietro A. et al. *Cell. Mol. Life. Sci.* 2002, 59, 307-322.). Even with their low toxicity, known flavonoids have only moderate activity as modulators of MDR. They have a broad spectrum of biological activity including anti-estrogen activity and they inhibit other ATPases. High doses of flavonoids as MDR modulators may cause side effects. Flavonoid dimers that sensitize chemorestistant tumors or parasitic infection including *Leishmania* have been characterized. (Chan, K. F. et al. *J Med Chem* 2006, 49, 6742-6759; Chan, K. F. et al. *Chem. Med. Chem.* 2009, 4, 594-614; Wong, I. L. et al. *Antimicrob Agents Chemother* 2007, 51, 930-940; Wong, I. L. et al. *J Med Chem* 2009, 52, 5311-5322; Wong, I. L. et al. *Leishmania. J Antimicrob Chemother* 2009, 63, 1179-1190; WO 2007/135592). The compounds inhibit membrane transporters like P-gp and MRP1 which would otherwise cause drug efflux. On the other hand, there is a limitation to the potential use of these flavonoid dimers in a clinical setting. Their modulating activity is not as potent compared to other compounds previously. More importantly, these compounds are quite insoluble in water or in non-polar organic solvents such as octanol and may not be well absorbed in vivo.

Leishmaniasis is one of several major parasitic diseases targeted by the World Health Organization (WHO). Leishmaniasis is endemic in over eighty countries in the world. More than 350 million people are at risk of infection and about two million people are infected annually. 500,000 of these cases are of the visceral form which could be fatal if left untreated. Currently, there is no vaccine for leishmaniasis. One treatment regimen is chemotherapy including pentavalent antimonials ($Sb^V$) which has been used for more than 50 years. Antimonials are not ideal due to the difficulty of administration, side effects and emergence of antimonials-resistant cases. It has been reported that more than 50% of the visceral leishmaniasis cases in India are resistant to the antimonials (Shyam S. et al. *Am. J. Trop. Med. Hyg,* 1997, 56, 522-5).

Leishmaniasis is responsible for considerable morbidity and mortality worldwide. However, chemotherapy currently available for treating leishmaniasis is far from satisfactory because of limited efficacy, toxic side effects, need for prolonged hospitalization during treatment period and emergence of drug resistance. There is an urgent need for novel, safer and more efficacious antileishmanial medicaments. Newer antileishmanials such as amphotericin B, miltefosine and paromomycin also have intrinsic limitations including toxicity, low efficacy, cost and inconvenient treatment protocol.

Plant derived compounds have recently been reported to exhibit antiparasitic properties of surprising efficacy and selectivity (Kayser, O. et al. *Parasitol Res* 2003, 90 Suppl 2, S55-62.). Flavonoids have been reported to have a wide range of biological activity, particularly as antioxidative and anticancer agents. Flavonoids represent a large family of polyphenolic compounds found in vegetables and fruits. Because humans consume large quantities of flavonoids in the diet, it is generally accepted that flavonoids are safe. The general structure of flavonoids contains a flavin nucleus with two aromatic rings (A and B rings) interconnected by third heterocyclic ring C. The most common flavonoids are flavone and isoflavone (Tasdemir, D.; et al. *Antimicrob Agents Chemother* 2006, 50, 1352-1364).

Biflavonoids are characterized by two flavonoid monomeric units (flavone or flavanone) covalently linked either with C—C or C—O—C bonds. Biflavonoids are rich in many species of plant and reported to have significant antiviral and antiprotozal activity (Weniger, B. et al. *Phytomedicine* 2006, 13, 176-180). Weniger et al. has reported that lanaroflavone, bilobetin, ginkgetin, isoginkgetin and sciadopitysin exhibit anti-axenic amastigote activity in vitro.

The mode of action of flavonoids has been investigated. For the proanthcyanidins, the leishmanicidal activity was reported to be due to macrophage activation rather than direct antiparasitic activity by generation of nitric oxide and tumor necrosis factor-α (Kolodziej, H. et al. *Biol Pharm Bull* 2001, 24, 1016-1021). Quercetin and luteolin inhibit topoisomerase and induce cell cycle arrest leading to apoptosis of *Leishmania* (Mitta, B.; et al. *Mol Med* 2000, 6, 527-541). A biflavonoid, 2",3"-diidroochnaflavone, isolated from the leaves of *Luxemburgia nobilis,* has been reported as cytotoxic to murine Ehrlich carcinoma and human leukemia K562 cells and found to have inhibitory activity of topoisomerase I and II-α(Oliveira, M. C. et al. *Planta Med* 2005, 71, 561-563). Morelloflavone, a biflavonoid, was found to inhibit tumor angiogenesis by targeting Rho GTPase and extracellular signal-regulated kinase signaling pathway (Pang, X. et al. *Cancer Res* 2009, 69, 518-525).

There is a need to provide compounds that are able to overcome at least one, but preferably more, of the problems as set forth in the prior art. It would be desirable to have effective against promastigotes and amastigotes. It would further be desirable to have compounds that are safe and non toxic to macrophages, and easy to synthesize.

SUMMARY OF THE INVENTION

In one aspect, there is provided a compound of formula Flavonoid-Linker-Y-Linker-Flavonoid
wherein
the flavonoid is selected from the group consisting of chalcone, flavone, flavonol, flavanone, anthocyanin, and isoflavonoid;
each linker independently comprises one or more groups selected from the group consisting of alkylene, ethylene amino, ethylene thio, ethylene glycol, propylene glycol, o-phenylenedioxy, m-phenylenedioxy, and p-phenylenedioxy or a combination thereof;
Y is an optionally substituted amino group or a S atom; provided that said linker is not connected to Y by a heteroatom In another aspect, there is provided a method of synthesizing a compound of formula Flavonoid-Linker-Y-Linker-Flavonoid as defined herein.

In another aspect, there is provided a method of reducing P-glycoprotein based multidrug resistance comprising the step of administering an effective amount of a compound as defined herein, or a pharmaceutically acceptable salt or solvate thereof.

In another aspect, there is provided a method of treating cancer comprising the step of administering an effective amount of a compound as defined herein, or a pharmaceutically acceptable salt or solvate thereof and an effective amount of an anti-cancer agent.

BRIEF DESCRIPTION OF THE DRAWING

Particular embodiments of the present invention will now be explained by way of example and with reference to the accompanying drawings, in which.

DETAILED DESCRIPTION OF THE PREFERRED EMBODIMENT

Figure 1:
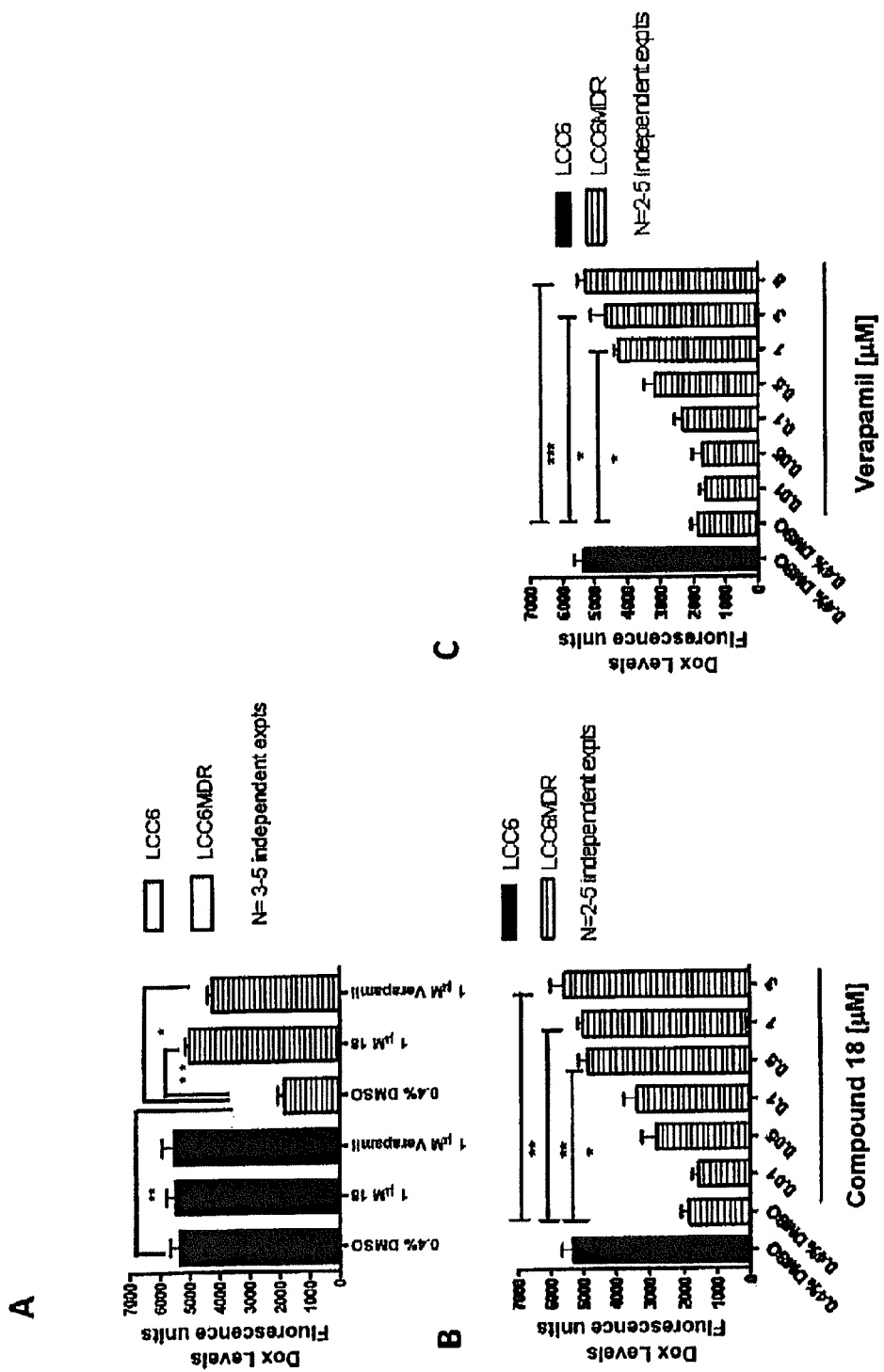
FIG. 1 shows the effect of compound 18 and Verapamil on Doxorubicin accumulation in LCC6 and LCC6MDR cells at equimolar concentrations (A); and dose dependent effect of compound 18 (B) and Verapamil (C) on Doxorubicin accumulation in LCC6MDR cells.

While the making and using of various embodiments are discussed below, it should be appreciated that the specific embodiments discussed herein are merely illustrative of specific ways of making and using the invention and should not be construed as to limit the scope of the invention.

In one embodiment, there is provided a compound of formula II:

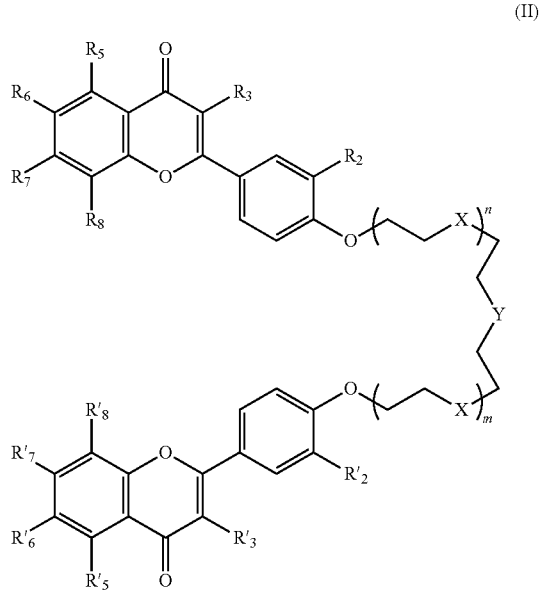

(II)

or a pharmaceutically acceptable salt or solvate thereof, wherein

Y is N—R1 or S $R_1$ is independently selected from the group consisting of H, alkyl, alkenyl, alkoxy, cycloalkyl, heterocycloalkyl, cycloalkenyl, heterocycloalkenyl, aryl, heteroaryl, —$(CH_2)_q$-aryl, —$(CH_2)_q$-heteroaryl, —$(CH_2)_q$-cycloalkyl, $(CH_2)_q$-cycloalkenyl, —$(CH_2)_q$-heterocycloalkyl, —$(CH_2)_q$-heterocycloalkenyl, —C(O)-alkyl, —C(O)-aryl, —C(O)-heteroaryl, —C(O)-cycloalkyl, —C(O)-cycloalkenyl, —C(O)-heterocycloalkyl, —C(O)-heterocycloalkenyl, —C(O)O-alkyl, —C(O)O-aryl, —C(O)O-heteroaryl, —C(O)β-cycloalkyl, —C(O)β-cycloalkenyl, —C(O)O-heterocycloalkyl, —C(O)O-heterocycloalkenyl, —S-alkyl, —S-aryl, —S-heteroaryl, —S-cycloalkyl, —S-heterocyloalkyl, —SO-alkyl, —SO-aryl, —SO-heteroaryl, —SO-cycloalkyl, —SO-heterocycloalkyl, —$SO_2$-alkyl, —$SO_2$-aryl, —$SO_2$-heteroaryl, —$SO_2$-cycloalkyl, or —$SO_2$-heterocycloalkyl, any of which may be optionally substituted;

$R_2$ is selected from the group consisting of H, OH, halogen, alkyl, alkenyl, alkoxy, aryloxy, cycloalkyl, heterocycloalkyl, cycloalkenyl, heterocycloalkenyl, aryl, —O—$(CH_2)_q$-aryl, —$(CH_2)_q$-cycloakyl, —$(CH_2)_q$-heterocycloalkyl, —$(CH_2)_q$-aryl, —$(CH_2)_q$-heteroaryl, —C(O)-alkyl, —C(O)-aryl, —C(O)-heteroaryl, —C(O)-cycloalkyl, —C(O)-heterocycloalkyl, —C(O)O-alkyl, —C(O)O-aryl, —C(O)O-heteroaryl, —C(O)O-cycloalkyl, or —C(O)O-heterocycloalkyl, any of which may be optionally substituted;

n, and m are independently an integer from 1 to 6;

X is selected from $CH_2$, O, S or N—$R_1$;

$R_3$; $R'_3$; $R_5$; $R'_5$; $R_6$; $R'_6$; $R_7$; $R'_7$; $R_8$; $R'_8$ are each independently H, OH, halogen, alkyl, alkenyl, alkoxy, cycloalkyl, heterocycloalkyl, cycloalkenyl, heterocycloalkenyl, aryl, aryloxy, —O—(CH$_2$)$_q$-aryl, —(CH$_2$)$_q$-aryl, —C(O)-alkyl, —C(O)-aryl, —C(O)-heteroaryl, —C(O)-cycloalkyl, —C(O)-heterocycloalkyl, —C(O)O-alkyl, —C(O)O-aryl, —C(O)O-heteroaryl, —C(O)β-cycloalkyl, or —C(O)O-heterocycloalkyl, nitro, amino, cyano, nitroso, or azido group, any of which may be optionally substituted; and q is an integer from 1 to 6.

In a further embodiment, there is provided a compound of formula IVa or IVb

IVa

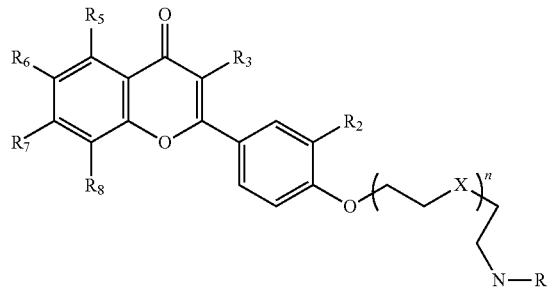

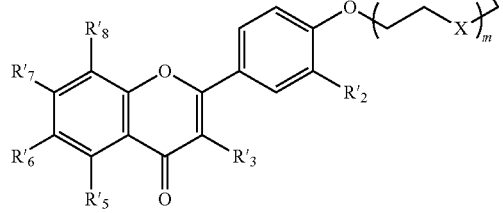

IVb

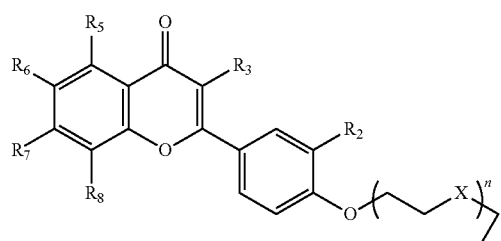

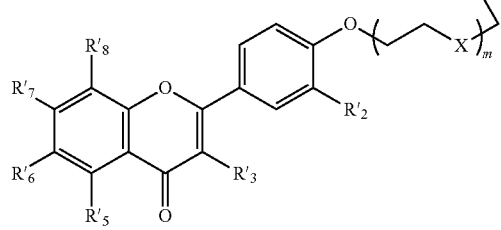

or a pharmaceutically acceptable salt or solvate thereof

In another embodiment, there is provided a compound of formula Va, Vb, Vc or Vd

Va

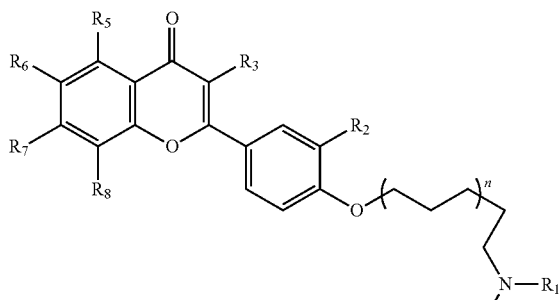

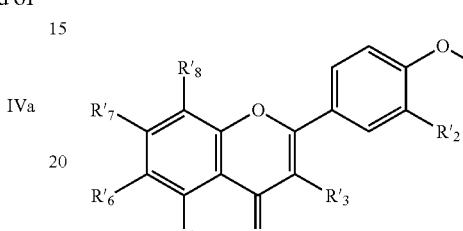

Vb

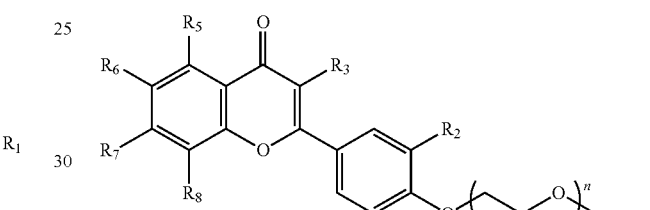

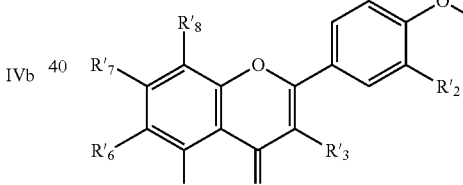

Vc

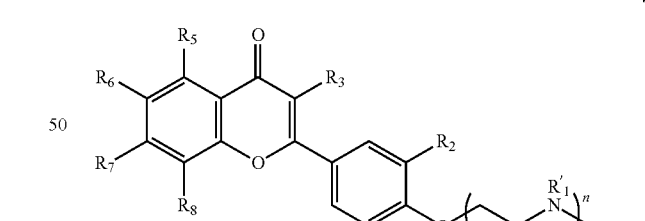

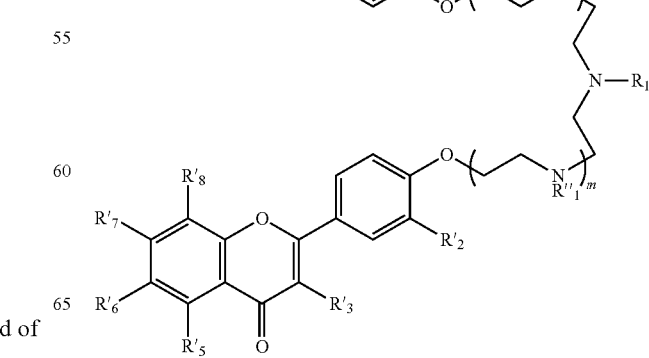

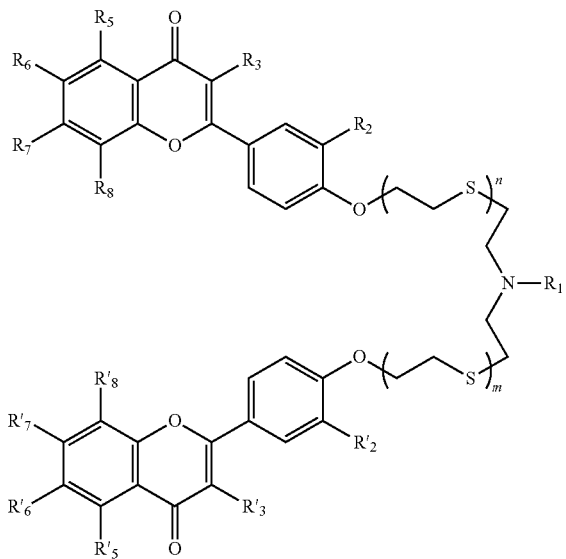

or a pharmaceutically acceptable salt or solvate thereof.

In one embodiment, there is provided a compound of formula II, IVa, IVb, Va, Vb, Vc, or Vd or a pharmaceutically acceptable salt or solvate thereof, wherein Y, when present, is N—R1 or S wherein $R_1$ is selected from the group consisting of H, alkyl, alkenyl, alkoxy, cycloalkyl, heterocycloalkyl, cycloalkenyl, heterocycloalkenyl, aryl, heteroaryl, —$(CH_2)_q$-aryl, —$(CH_2)_q$-heteroaryl, —$(CH_2)_q$-cycloalkyl, —$(CH_2)_q$-cycloalkenyl, —$(CH_2)_q$-heterocycloalkyl, —$(CH_2)_q$-heterocycloalkenyl, —C(O)-alkyl, —C(O)-aryl, —C(O)-heteroaryl, —C(O)-cycloalkyl, —C(O)-cycloalkenyl, —C(O)-heterocycloalkyl, —C(O)-heterocycloalkenyl, —C(O)O-alkyl, —C(O)O-aryl, —C(O)O-heteroaryl, —C(O)β-cycloalkyl, —C(O)β-cycloalkenyl, —C(O)O-heterocycloalkyl, —C(O)O-heterocycloalkenyl, —S-alkyl, —S-aryl, —S-heteroaryl, —S-cycloalkyl, —S-heterocycloalkyl, —SO-alkyl, —SO-aryl, —SO-heteroaryl, —SO-cycloalkyl, —SO-heterocycloalkyl, —$SO_2$-alkyl, —$SO_2$-aryl, —$SO_2$-heteroaryl, —$SO_2$-cycloalkyl, or —$SO_2$-heterocycloalkyl, any of which may be optionally substituted;

$R_2$ and $R'_2$ is selected from the group consisting of H, OH, halogen, alkyl, alkenyl, alkoxy, aryloxy, cycloalkyl, heterocycloalkyl, cycloalkenyl, heterocycloalkenyl, aryl, —O—$(CH_2)_q$-aryl, —$(CH_2)_q$-cycloakyl, —$(CH_2)_q$-heterocycloalkyl, —$(CH_2)_q$-aryl, —$(CH_2)_q$-heteroaryl, —C(O)-alkyl, —C(O)-aryl, —C(O)-heteroaryl, —C(O)-cycloalkyl, —C(O)-heterocycloalkyl, —C(O)O-alkyl, —C(O)O-aryl, —C(O)O-heteroaryl, —C(O)O-cycloalkyl, or —C(O)O-heterocycloalkyl, any of which may be optionally substituted;

n, and m are independently an integer from 1 to 6;

X is selected from $CH_2$, O, S or N—$R_1$;

$R_3$; $R'_3$; $R_5$; $R'_5$; $R_6$; $R'_6$; $R_7$; $R'_7$; $R_8$; $R'_8$ are each independently H, OH, halogen, alkyl, alkenyl, alkoxy, cycloalkyl, heterocycloalkyl, cycloalkenyl, heterocycloalkenyl, aryl, aryloxy, —O—$(CH_2)_q$-aryl, —$(CH_2)_q$-aryl, —C(O)-alkyl, —C(O)-aryl, —C(O)-heteroaryl, —C(O)-cycloalkyl, —O(O)-heterocycloalkyl, —C(O)O-alkyl, —C(O)O-aryl, —C(O)O-heteroaryl, —C(O)β-cycloalkyl, or —C(O)O-heterocycloalkyl, nitro, amino, cyano, nitroso, or azido group, any of which may be optionally substituted;

q is an integer from 1 to 6.

In another embodiment, there is provided a compound of formula II, IVa, IVb, Va, Vb, Vc, or Vd or a pharmaceutically acceptable salt or solvate thereof, wherein $R_1$ is selected from the group consisting of H, alkyl, alkenyl, alkoxy, cycloalkyl, heterocycloalkyl, cycloalkenyl, heterocycloalkenyl, aryl, heteroaryl, —$(CH_2)_q$-aryl, —$(CH_2)_q$-heteroaryl, —$(CH_2)_q$-cycloalkyl, —$(CH_2)_q$-cycloalkenyl, —$(CH_2)_q$-heterocycloalkyl, —$(CH_2)_q$-heterocycloalkenyl, —C(O)-alkyl, —C(O)-aryl, —C(O)-heteroaryl, —C(O)-cycloalkyl, —C(O)-cycloalkenyl, —C(O)-heterocycloalkyl, —C(O)-heterocycloalkenyl, —C(O)O-alkyl, —C(O)O-aryl, —C(O)O-heteroaryl, —C(O)O-cycloalkyl, —C(O)O-cycloalkenyl, —C(O)O-heterocycloalkyl, —C(O)O-heterocycloalkenyl, —S-alkyl, —S-aryl, —S-heteroaryl, —S-cycloalkyl, —S-heterocycloalkyl, —SO-alkyl, —SO-aryl, —SO-heteroaryl, —SO-cycloalkyl, —SO-heterocycloalkyl, —$SO_2$-alkyl, —$SO_2$-aryl, —$SO_2$-heteroaryl, —$SO_2$-cycloalkyl, or —$SO_2$-heterocycloalkyl, any of which may be optionally substituted.

In another embodiment, there is provided a compound of formula II, IVa, IVb, Va, Vb, Vc, or Vd or a pharmaceutically acceptable salt or solvate thereof, wherein $R_1$ is selected from the group consisting of H, alkyl, aryl, —$(CH_2)_q$-aryl, —$(CH_2)_q$-heteroaryl, —$(CH_2)_q$-cycloalkyl, —C(O)-alkyl, —C(O)-aryl, —C(O)O-alkyl, —$SO_2$-alkyl, —$SO_2$-aryl, any of which may be optionally substituted.

In another embodiment, there is provided a compound of formula II, IVa, IVb, Va, Vb, Vc, or Vd or a pharmaceutically acceptable salt or solvate thereof, wherein $R_1$ is selected from the group consisting of H, C1-6alkyl, C6-10aryl, —$(CH_2)_{1-3}$—C6-10aryl, —$(CH_2)_{1-3}$-heteroaryl, —$(CH_2)_{1-3}$-cycloalkyl, —C(O)—C1-6alkyl, —C(O)—C6-10aryl, —C(O)O—C1-6alkyl, —$SO_2$—C1-6alkyl, —$SO_2$—C6-10aryl, any of which may be optionally substituted.

In another embodiment, there is provided a compound of formula II, IVa, IVb, Va, Vb, Vc, or Vd or a pharmaceutically acceptable salt or solvate thereof, wherein $R_1$ is selected from the group consisting of H, methyl, ethyl, phenyl, —$(CH_2)$-phenyl —$(CH_2)$-pyridyl;, —$(CH_2)$-phthalimidyl, —$(CH_2)$-piperonyl; —$(CH_2)$-naphthyl; —$(CH_2)$-benzimidazolyl; —$(CH_2)$-pyrimidinyl; —$(CH_2)$-quinolinyl; —$(CH_2)$-cyclohexyl, —C(O)-methyl, —C(±)-ethyl, —C(O)-trityl, —C(O)-phenyl, —C(O)O-tert-butyl, —$SO_2$-methyl, —$SO_2$-phenyl and —$SO_2$-naphthyl, any of which may be optionally substituted.

In another embodiment, there is provided a compound of formula II, IVa, IVb, Va, Vb, Vc, or Vd or a pharmaceutically acceptable salt or solvate thereof, $R_1$ is as defined herein and is optionally substituted with halo, carboxyalkyl, azido, cyano, hydroxyl, nitro, nitroso, NR20R21, $CF_3$, $OCF_3$, —C(O)-aryl, —C(O)O-alkyl, alkyl, alkoxy, aryl, aryloxy, heteroaryl, alkenyl, cycloalkyl, heterocycloalkyl, cycloalkenyl, heterocycloalkenyl, or halogen, and R20 and R21 each independently are H, alkyl or a protecting group;

In another embodiment, there is provided a compound of formula II, IVa, IVb, Va, Vb, Vc, or Vd or a pharmaceutically acceptable salt or solvate thereof, wherein $R_1$ is as defined in table A of substituent R1:

Table A of substituent R1:

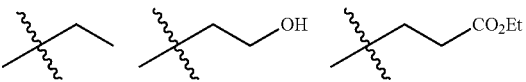

Table A of substituent R1:
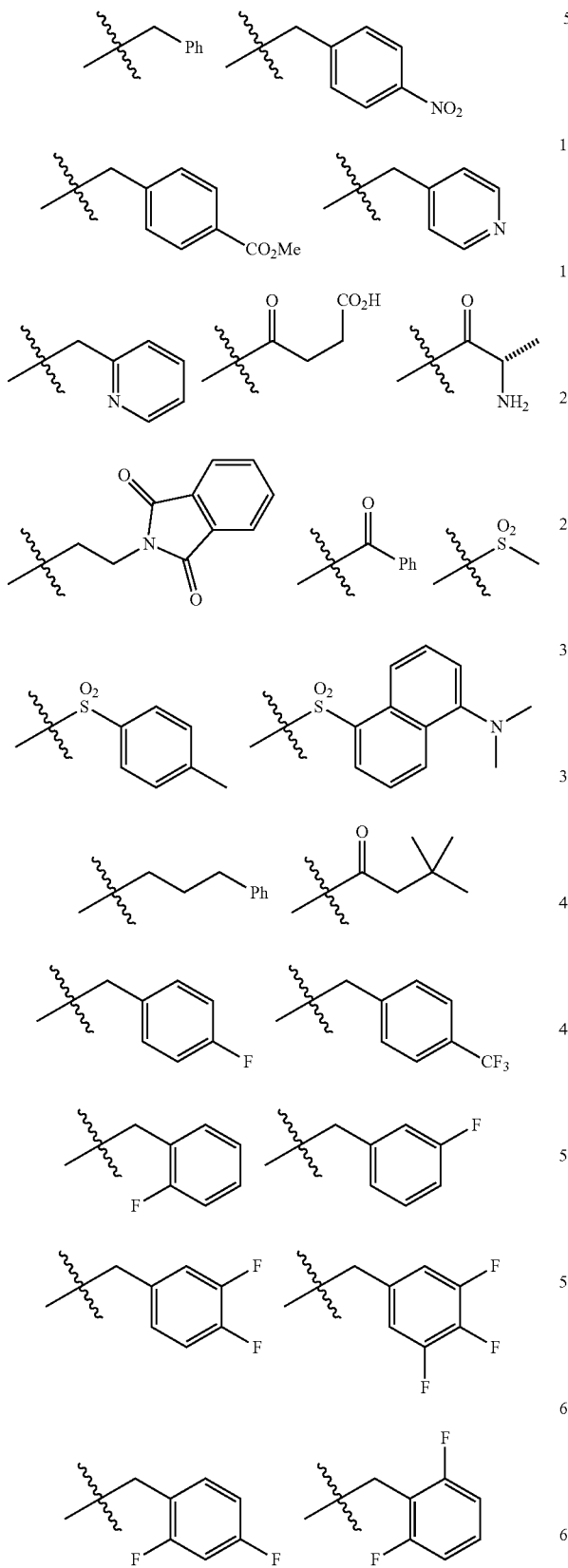
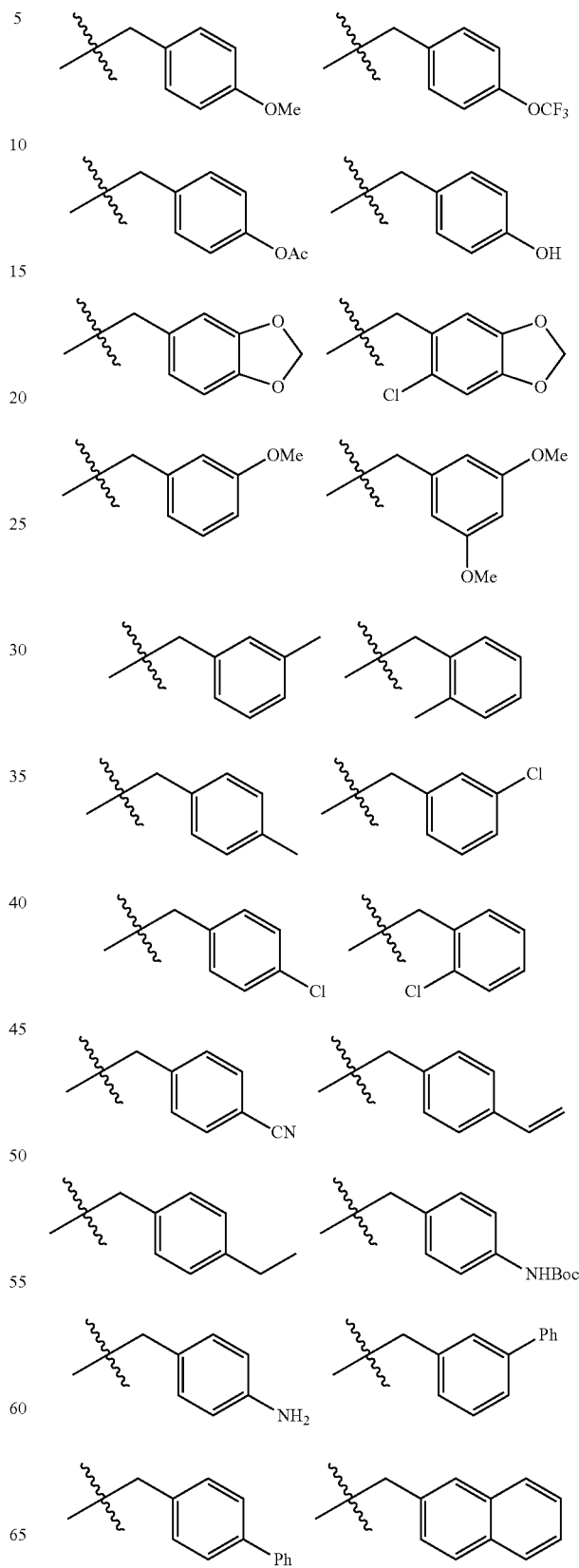

Table A of substituent R1:

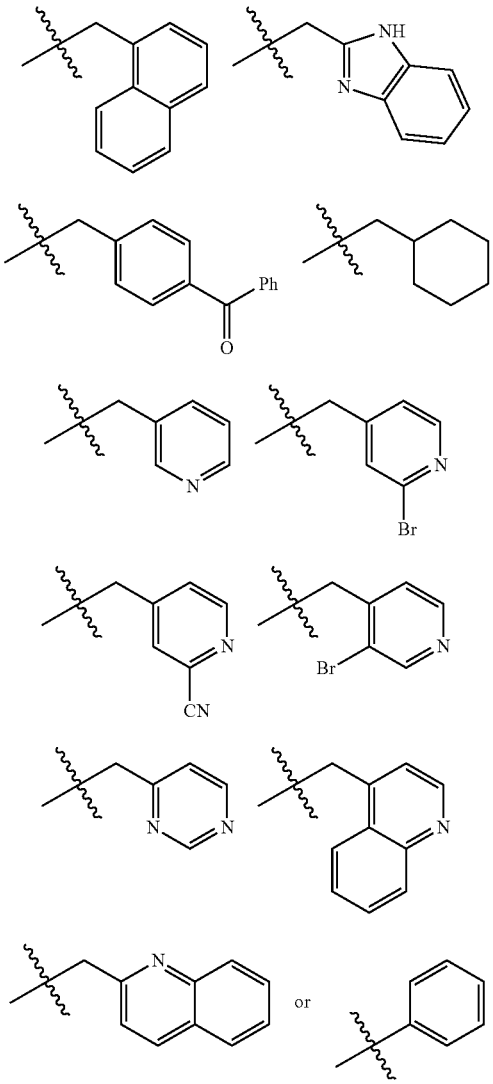

In another embodiment, there is provided a compound of formula II, IVa, IVb, Va, Vb, Vc, or Vd or a pharmaceutically acceptable salt or solvate thereof, $R_1$ is selected from $CH_2CH_3$, $CH_2CH_2$-phthalimido, $CH_2CH_2CH_2—C_6H_6$, $CH_2C_6H_5$, $CH_2(2F—C_6H_4)$, $CH_2(3F—C_6H_4)$, $CH_2(4NO_2—C_6H_4)$, $CH_2(4F—C_6H_4)$, $CH_2(4CF_3—C_6H_4)$, $CH_2(4OMe-C_6H_4)$, $CH_2(4-C_6H_5—C_6H_4)$, $CH_2(3,4-F—C_6H_3)$, $CH_2(3,4,5-F—C_6H_2)$, and $CH_2(2-C_5H_4N)$;

In another embodiment, there is provided a compound of formula II, IVa, IVb, Va, Vb, Vc, or Vd or a pharmaceutically acceptable salt or solvate thereof, wherein $R_1$ is selected from $CH_2C_6H_5$, $CH_2(2F—C_6H_4)$, $CH_2(3F—C_6H_4)$, $CH_2(4NO_2—C_6H_4)$, $CH_2(4F—C_6H_4)$, $CH_2(4CF_3—C_6H_4)$, $CH_2(4OMe—C_6H_4)$, $CH_2(4-C_6H_5—C_6H_4)$, $CH_2(3,4-F—C_6H_3)$, and $CH_2(3,4,5-F—C_6H_2)$;

In another embodiment, there is provided a compound of formula II, IVa, IVb, Va, Vb, Vc, or Vd or a pharmaceutically acceptable salt or solvate thereof, wherein $R_1$ is selected from $CH_2CH_3$, $CH_2CH_2OH$, $(CH_2)_2CO_2CH_2CH_3$, $C(=O)OC(CH_3)_3$, $CH_2C_6H_5$, $CH_2(4NO_2—C_6H_4)$, $CH_2(4-CO_2CH_3—C_6H_4)$, $CH_2(4-C_5H_4N)$, $CH_2(2-C_5H_4N)$, $C=O(CH_2)_2CO_2H$, $SO_2CH_3$, $SO_2(4-CH_3—C_6H_4)$, and $(CH_2)_3C_6H_5$.

In another embodiment, there is provided a compound of formula II, IVa, IVb, Va, Vb, Vc, or Vd or a pharmaceutically acceptable salt or solvate thereof, wherein
$R_1$ is as defined above in any embodiment and $R_2$ and $R'_2$ are independently selected from the group consisting of H, OH, halogen, or an alkyl, alkoxy, —O—$(CH_2)_q$-aryl, —C(O)-alkyl, —C(O)O-alkyl, which may be optionally substituted;

In another embodiment, there is provided a compound of formula II, IVa, IVb, Va, Vb, Vc, or Vd or a pharmaceutically acceptable salt or solvate thereof, wherein
$R_1$ is as defined above in any embodiment and $R_2$ and $R'_2$ are independently selected from the group consisting of H, OH, halogen, —O—$(CH_2)$-aryl, C1-6alkyl, or C1-6alkoxy, any of which may be optionally substituted.

In another embodiment, there is provided a compound of formula II, IVa, IVb, Va, Vb, Vc, or Vd or a pharmaceutically acceptable salt or solvate thereof, wherein
$R_1$ is as defined above in any embodiment and $R_2$ and $R'_2$ are independently selected from the group consisting of H, OH, halogen, —O—$CH_2$-phenyl, methyl or methoxy, any of which may be optionally substituted.

In another embodiment, there is provided a compound of formula II, IVa, IVb, Va, Vb, Vc, or Vd or a pharmaceutically acceptable salt or solvate thereof, wherein $R_1$, $R_2$ and $R'_2$ are as defined above in any embodiment and $R_3$; $R'_3$; $R_5$; $R'_5$; $R_6$; $R'_6$; $R_7$; $R'_7$, $R_8$; $R'_8$ are each independently H, OH, halogen, alkyl, alkoxy, aryloxy, —O—$(CH_2)_q$-aryl, —$(CH_2)_q$-aryl, —C(O)-alkyl, or —C(O)O-alkyl, any of which may be optionally substituted or a nitro, amino, cyano, nitroso, or azido group.

In another embodiment, there is provided a compound of formula II, IVa, IVb, Va, Vb, Vc, or Vd or a pharmaceutically acceptable salt or solvate thereof, wherein $R_1$, $R_2$ and $R'_2$ are as defined above in any embodiment and $R_3$, $R'_3$; $R_5$; $R'_5$; $R_6$; $R'_6$; $R_7$; $R'_7$; $R_8$; $R'_8$ are each independently H, OH, halogen, $C_{1-4}$alkyl, $C_{1-4}$alkoxy, $C_{6-10}$aryloxy, —O—$(CH_2)$-aryl, or $(CH_2)$-phenyl.

In another embodiment, there is provided a compound of formula II, IIIa, IIIb, IVa, IVb, Va, Vb, Vc, or Vd or a pharmaceutically acceptable salt or solvate thereof, wherein $R_1$, $R_2$ and $R'_2$, $R_3$; $R'_3$; $R_5$; $R'_5$; $R_6$; $R'_6$; $R_7$; $R'_7$; $R_8$; $R'_8$ are as defined above in any embodiment and wherein n, m and q are 1.

In one embodiment, there is provided a compound of formula II, IIIa, IIIb, IVa, IVb, Va, Vb, Vc, or Vd or a pharmaceutically acceptable salt or solvate thereof, wherein
X=O; n=1 and m=1
$R_2$=H or $CH_3O$; $R'_2$=H or $CH_3O$
$R_1$=H; $CH_2CH_3$; $CH_2CH_2OH$; $(CH_2)_2CO_2CH_2CH_3$; $C(=O)OC(CH_3)_3$; $CH_2C_6H_5$; $CH_2(4-NO_2—C_6H_4)$; $CH_2(4-CO_2CH_3—C_6H_4)$; $CH_2(4-C_5H_4N)$; $CH_2(2-C_5H_4N)$; C=O$(CH_2)_2CO_2H$; $SO_2CH_3$; $SO_2(4-CH_3—C_6H_4)$; $(CH_2)_3C_6H_5$; Dansyl; L-alanyl; C=O$C_6H_5$; C=O$CH_2C(CH_3)_3$; $CH_2(4-F—C_6H_4)$; $CH_2(4-CF_3—C_6H_4)$; $CH_2(2-F—C_6H_4)$; $CH_2(3-F—C_6H_4)$; $CH_2(2,3-F_2C_6H_3)$; $CH_2(3,4,5-F_3—C_6H_2)$; $CH_2(4-OCH_3—C_6H_4)$ and $R_3$; $R'_3$; $R_5$; $R'_5$; $R_6$; $R'_6$; $R_7$; $R'_7$; $R_8$; $R'_8$ are H; or
$R_5$; $R'_5$; $R_7$; $R'_7$ are OH and $R_3$; $R'_3$, $R_6$; $R'_6$; $R_8$; $R'_8$ are H
$R_6$; and $R'_6$ are $CH_3$ and $R_3$; $R'_3$; $R_5$; $R'_5$; $R_7$; $R'_7$; $R_8$; $R'_8$ are H; or
$R_7$ and $R'_7$ are $CH_3$ and $R_3$; $R'_3$; $R_5$; $R'_5$; $R_6$; $R'_6$; $R_8$; $R'_8$ are H; or
$R_3$ and $R'_3$ are $CH_3$ and $R_5$; $R'_5$; $R_6$; $R'_6$; $R_7$; $R'_7$, $R_8$; $R'_8$ are H; or
$R_6$; and $R'_6$ are $CH_2CH_3$ and $R_3$; $R'_3$; $R_5$; $R'_5$; $R_7$; $R'_7$; $R_8$; $R'_8$ are H; or $R_7$ and $R'_7$ are F and $R_3$; $R'_3$, $R_5$; $R'_5$; $R_6$; $R'_6$, $R_8$; $R'_8$ are H; or $R'_6$=$CH_3$ and $R'_8$=$N_3$ and R and $R_3$; $R'_3$; $R_5$; $R'_5$; $R_6$; $R_7$; $R'_7$; $R_8$; are H; or $R_6$=$CH_3$; $R'_6$=$CH_3$ and $R'_8$=$N_3$ and $R_3$; $R'_3$; $R_5$; $R'_5$; $R_7$; $R'_7$; $R_8$; are H; or $R_6$=$CH_3$; $R'_6$=$CH_3$ and $R'_5$=$NO_2$ and $R_3$; $R'_3$; $R_5$; $R'_5$; $R_7$; $R'_7$; $R_8$; are H; or $R_6$=$CH_3$, $R'_6$=$CH_3$ and $R'_8$=$NH_2$ and $R_3$; $R'_3$; $R_5$; $R'_5$; $R_7$; $R'_7$; $R_8$; are H.

In one embodiment, there is provided a compound of formula II or a pharmaceutically acceptable salt or solvate thereof, wherein Y is N—R1

$R_1$ is selected from the group consisting of H or a group alkyl, aryl, —$(CH_2)_q$-aryl, —$(CH_2)_q$-heteroaryl, —$(CH_2)_q$-cycloalkyl, —C(O)-aryl, —C(O)O-alkyl, —$SO_2$-alkyl, and —$SO_2$-aryl, any of which may be optionally substituted with azido, cyano, hydroxyl, nitro, nitroso, $NR_{20}R_{21}$, perfluoroalkyl, perfluoroalkyloxy, —C(O)-aryl, —C(O)O-alkyl, alkyl, alkoxy, aryl, aryloxy, heteroaryl, alkenyl, cycloalkyl, heterocycloalkyl, cycloalkenyl, heterocycloalkenyl, or halogen, wherein $R_{20}$ and $R_{21}$ each independently are H, alkyl or a protecting group; and when R1 comprises an aryl, an additional optional substituent is alkylenedioxy;

$R_2$ and $R'_2$ are independently selected from the group consisting of H, OH, halogen, or an alkyl, alkoxy, —O—$(CH_2)_q$-aryl, —C(O)-alkyl, —C(O)O-alkyl, which may be optionally substituted n, and m are an integer 1; and q is 1 to 3;

X is O;

$R_3$; $R'_3$; $R_5$; $R'_5$; $R_6$; $R'_6$; $R_7$; $R'_7$; $R_8$; $R'_8$ are each independently H, OH, halogen, C1-4alkyl, C1-4-alkoxy, C6-10aryloxy, —O—$(CH_2)$-aryl, or $(CH_2)$-aryl.

In one embodiment, there is provided a compound of formula II or a pharmaceutically acceptable salt or solvate thereof, wherein Y is N—R1

$R_1$ is selected from the group consisting of H or a group alkyl unsubstituted or substituted by an hydroxyl or carboxyalkyl; aryl; —$(CH_2)$-aryl unsubstituted or substituted by one or more halogen, carboxymethyl, carboxyethyl, nitro, $OCF_3$, $CF_3$, methylenedioxy, methyl, methoxy, phenyl, $NH_2$, NHBOC, C(O)Ph, cyano, ethylene; —$(CH_2)$-heteroaryl unsubstituted or substituted by a halogen or cyano; —$(CH_2)$ cycloalkyl, —C(O)-alkyl unsubstituted or substituted by an amino, alkyl (such as methyl, ethyl or methylene-t-butyl) or carboxy; —C(O)-aryl, —$SO_2$-alkyl, and —$SO_2$-aryl unsubstituted or substituted by a methyl or amino (such as dimethylamino);

$R_2$ and $R'_2$ are independently selected from the group consisting of H, OH, halogen, or an methyl, methoxy, —$OCH_2$-phenyl, —C(O)-alkyl, —C(O)O-alkyl, which may be optionally substituted n, and m are an integer 1;

X is O;

$R_3$; $R'_3$; $R_5$; $R'_5$; $R_6$; $R'_6$; $R_7$; $R'_7$; $R_8$; $R'_8$ are each independently H, OH, halogen, $C_{1-4}$alkyl, C1-4-alkoxy, C6-10aryloxy, —O—$(CH_2)$-aryl, or $(CH_2)$-aryl.

In one embodiment, there is provided a compound of formula II or a pharmaceutically acceptable salt or solvate thereof, wherein Y is N—R1

$R_1$ is as defined in table A of substituent R1 above;

$R_2$ and $R'_2$ are independently selected from the group consisting of H, OH, halogen, or an alkyl, alkoxy, —O—$(CH_2)_q$-aryl, —C(O)-alkyl, —C(O)O-alkyl, which may be optionally substituted n, and m are an integer 1;

X is O;

$R_3$; $R'_3$; $R_5$; $R'_5$; $R_6$; $R'_6$; $R_7$; $R'_7$; $R_8$; $R'_8$ are each independently H, OH, halogen, $C_{1-4}$alkyl, C1-4-alkoxy, C6-10aryloxy, —O—$(CH_2)$-aryl, or $(CH_2)$-aryl.

In an embodiment, there is provided herein a pharmaceutical composition comprising a compound as defined herein or a pharmaceutically acceptable salt or solvate thereof, and one or more than one pharmaceutically acceptable carriers. Many pharmaceutically acceptable carriers are known in the art. It will be understood by those in the art that a pharmaceutically acceptable carrier must be compatible with the other ingredients of the formulation and tolerated by a subject in need thereof.

In another embodiment, the pharmaceutical composition comprises at least one additional active ingredient including, but are not limited to, antioxidants, free radical scavenging agents, peptides, growth factors, antibiotics, bacteriostatic agents, immunosuppressives, anticoagulants, buffering agents, anti-inflammatory agents, anti-pyretics, time-release binders, anesthetics, steroids and corticosteroids, or other active ingredient commonly used in combination therapy for cancer as anti-cancer agent including but not limited to Paclitaxel, Doxorubicin, Daunorubicin, Mitoxantrone, Taxol, Docetaxel, Vinblastine, Vincristine, Camptothecin Topotecan, Etoposide, Teniposide and other natural, modified or synthetic chemotherapeutic agents known in the art. In another embodiment, the pharmaceutical composition comprises at least one additional active ingredient including, but are not limited to, antioxidants, free radical scavenging agents, peptides, growth factors, antibiotics, bacteriostatic agents, immunosuppressives, anticoagulants, buffering agents, anti-inflammatory agents, anti-pyretics, time-release binders, anesthetics, steroids and corticosteroids, or other active ingredient commonly used for treating protozoan infection including pentavalent antimonials ($Sb^V$) such as sodium stibogluconate, amphotericin B (with or without liposomal formulations), miltefosine and paromomycin.

In an embodiment, the pharmaceutical compositions comprise a compound as defined herein or a pharmaceutically acceptable salt or solvate thereof, and a pharmaceutically acceptable carrier, optionally in association with at least one additional active agent. In another embodiment, the pharmaceutical compositions comprise a compound of the present invention formula II, IVa, IVb, Va, Vb, Vc, or Vd and a pharmaceutically acceptable carrier, optionally in association with at least one additional active agent.

In another aspect, the compounds and compositions comprise a compound selected from the group consisting of the compounds described herein, pharmaceutically acceptable salts, analogs, and mixtures thereof. Pharmaceutically acceptable salts of known in the art and it should be understood that pharmaceutically acceptable salts of the compounds described herein are encompassed by the present invention.

Compositions and formulations of the invention include those suitable for oral, rectal, nasal, topical (including transdermal, buccal and sublingual), vaginal, parental (including subcutaneous, intramuscular, intravenous and intradermal) and pulmonary administration. Compositions of the present invention suitable for oral administration can be presented for example as discrete units such as capsules, cachets or tablets, each containing a predetermined amount of the active ingredient; or as an oil-in-water liquid emulsion, water-in-oil liquid emulsion or as a supplement within an aqueous solution. The active ingredient can also be presented as bolus, electuary, or paste. Formulations suitable for topical administration in the mouth include lozenges comprising the active ingredient, pastilles comprising the active ingredient in gelatin and glycerin, or sucrose and acacia.

Pharmaceutical compositions for topical administration according to the present invention can be formulated for example as an ointment, cream, suspension, lotion, powder, solution, paste, gel, spray, aerosol or oil. Alternatively, a formulation may comprise a patch or a dressing such as a bandage or adhesive plaster impregnated with active ingredients, and optionally one or more excipients or diluents.

Formulations suitable for topical administration to the eye also include eye drops wherein the active ingredient is dissolved or suspended in a suitable carrier, especially a sterile aqueous solvent for the agent. Formulations for rectal administration may be provided as a suppository with a suitable base comprising, for example, cocoa butter or a salicylate. Formulations suitable for vaginal administration can be presented as pessaries, tampons, creams, gels, pastes, foams or spray formulations containing in addition to the agent, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held to the nose. Suitable formulations wherein the carrier is a liquid for administration by nebulizer include for example aqueous or oily solutions of the agent.

Formulations suitable for parenteral administration include aqueous and non-aqueous isotonic sterile injection solutions which may contain preservatives, buffers, bacteriostatic agents and solutes which render the formulation isotonic with the blood of the patient; and aqueous and nonaqueous sterile suspensions which can include suspending agents and thickening agents, and liposomes or other microparticulate systems which are designed to target the compound to blood components or one or more organs. Extemporaneous injection solutions and suspensions can be prepared from sterile powders, granules and tablets.

It should be understood that in addition to the ingredients particularly mentioned above, the compositions and formulations of this invention can include other agents conventional in the art regarding the type of formulation in question. For example, formulations suitable for oral administration can include such further agents as sweeteners, thickeners, and flavoring agents. It also is intended that the agents, compositions, and methods of this invention be combined with other suitable compositions and therapies.

Various delivery systems are known and can be used to administer a therapeutic agent of the invention, e.g., encapsulation in liposomes, microparticles, microcapsules and the like. Methods of delivery include, but are not limited to, intraarterial, intramuscular, intravenous, intranasal, and oral routes. In a specific embodiment, the compounds and pharmaceutical compositions of the invention can be administered locally to the area in need of treatment; such local administration can be achieved, for example, by local infusion during surgery, by injection, or by means of a catheter.

Therapeutic amounts can be empirically determined and will vary with the pathology being treated, body mass of the subject being treated, and the efficacy and toxicity of the agent. Similarly, suitable dosage formulations and methods of administering the agents can be readily determined by those of skill in the art. For example, a daily dosage can be divided into one, two or more doses in a suitable form to be administered at one, two or more times throughout a time period.

The compounds and pharmaceutical compositions can be administered by any of a variety of routes, such as orally, intranasally, parenterally or by inhalation, and can take the form, for example, of tablets, lozenges, granules, capsules, pills, ampoule, suppositories or aerosol form. They can also be in the form of suspensions, solutions, and emulsions of the active ingredient in aqueous or nonaqueous diluents, syrups, granulates or powders. In addition to an agent of the present invention, the pharmaceutical compositions can also contain other pharmaceutically active compounds.

Ideally, the therapeutic agent of the invention should be administered to achieve peak concentrations of the active compound at sites of the disease. Peak concentrations at disease sites can be achieved, for example, by intravenously injecting the agent, optionally in saline, or orally administering, for example, a tablet, capsule or syrup containing the active ingredient.

Advantageously, the compounds and compositions of the invention can be administered simultaneously or sequentially with other drugs or biologically active agents. Examples include, but are not limited to, antioxidants, free radical scavenging agents, peptides, growth factors, antibiotics, bacteriostatic agents, immunosuppressives, anticoagulants, buffering agents, anti-inflammatory agents, anti-pyretics, time-release binders, anesthetics, steroids and corticosteroids.

Another aspect of the present invention is directed to methods of reversing multidrug resistance mediated by protein transporters including without limitation P-gp and MRP1.

In an aspect, a method of inhibiting P-gp and MRP1 activity is provided, comprising contacting a cell with a sufficient amount of a compound or composition of the invention.

In another aspect, the present invention provides a method of reversing multidrug resistance, comprising administering to a subject a therapeutically effective amount of a compound or pharmaceutical composition of the present invention.

A method of treating cancer comprising the step of administering an effective amount of a compound, or a pharmaceutically acceptable salt or solvate thereof or pharmaceutical composition of the present invention and an effective amount of an anti-cancer agent.

In accordance with another embodiment of the present invention, there is provided a method of treating protozoan disease, comprising administering to a subject a therapeutically effective amount of a compound or pharmaceutical composition of the present invention.

A protozoan disease to be treated in accordance with an embodiment of the present invention may be selected from the group consisting of, but not limited to, malaria, leishmaniasis, Chagas disease, trypanosomiasis, and toxoplasmosis.

In another embodiment of the present invention, there is provided herein a method of inhibiting a protozoan disease, comprising administering to a subject a therapeutically effective amount of a compound or pharmaceutical composition of the present invention.

For the purpose of the present invention the following terms are defined below:

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "inhibition" is intended to mean a substantial slowing, interference, suppression, prevention, delay and/or arrest of a chemical or biochemical action.

The term "pharmacological inhibition" is intended to mean a substantial slowing, interference, suppression, prevention, delay and/or arrest of a chemical action which is caused by an effective amount of a compound, drug, or agent.

The term "inhibitor" is intended to mean a compound, drug, or agent that substantially slows, interferes, suppresses, prevents, delays and/or arrests a chemical action.

The term "alkyl group", as used herein, is understood as referring to a saturated, monovalent unbranched or branched hydrocarbon chain. Examples of alkyl groups include, but are not limited to, C1-10 alkyl groups, preferably C1-6alkyl and most preferably C1-4alkyl. Examples of alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, nonyl and decyl. The term "alkyl" is also meant to include alkyls in which one or more hydrogen atom is replaced by a halogen, ie. an alkylhalide, for example, but not exclusively, C1-C10-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl.

The term "aryl" represents a carbocyclic moiety containing at least one benzenoid-type ring (i.e., may be monocyclic or polycyclic). Preferably "aryl" has 6 to 10 carbon atoms. Examples include but are not limited to phenyl, tolyl, dimethylphenyl, aminophenyl, anilinyl, naphthyl, anthryl, phenanthryl or biphenyl.

The term "aryloxy" represents an aryl moiety, which is covalently bonded to the adjacent atom through an oxygen atom. Examples include but are not limited to phenoxy, dimethylphenoxy, aminophenoxy, anilinoxy, naphthoxy, anthroxy, phenanthroxy or biphenoxy.

The term "arylalkyl" represents an aryl group attached to the adjacent atom by an alkyl, alkenyl or alkynyl. Examples include but are not limited to benzyl, benzhydryl, trityl, phenethyl, 3-phenylpropyl, 2-phenylpropyl, 4-phenylbutyl and naphthylmethyl.

The term "heteroaryl" represents a 3 to 11 membered optionally substituted saturated, unsaturated, partially saturated or aromatic cyclic moiety wherein said cyclic moiety is interrupted by at least one heteroatom selected from oxygen (O), sulfur (S) or nitrogen (N). Heteraryls may be monocyclic or polycyclic rings. Heteroaryls may be 3 to 6 membered monocyclic ring or 5 to 6 membered monocyclic ring. Heteroaryls may be 7 to 12 membered bicyclic ring or 9 to 10 membered bicyclic ring. Examples of heteroaryls include but are not limited to azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl oxazolyl, piperazinyl, piperonyl, pyrazinyl, pyridazinyl, pyrimidinyl, piperidyl, piperidino, pyridyl, pyranyl, pyrazolyl, pyrrolyl, pyrrolidinyl, phthalimidyl, thiatriazolyl, tetrazolyl, thiadiazolyl, triazolyl, thiazolyl, thienyl, tetrazinyl, thiadiazinyl, triazinyl, thiazinyl and thiopyranyl, furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl.

The term "alkenyl" refers to a straight or branched chain alkyl moiety having two or more carbon atoms (e.g., two to six carbon atoms, $C_{2-6}$ alkenyl) and having in addition one double bond, of either E or Z stereochemistry where applicable. Examples of alkenyl, groups include but are not limited to, allyl, vinyl, acetylenyl, ethylenyl, propenyl, isopropenyl, butenyl, isobutenyl, hexenyl, butadienyl, pentenyl, pentadienyl, hexenyl, hexadienyl, hexatrienyl, heptenyl, heptadienyl, heptatrienyl, octenyl, octadienyl, octatrienyl, octatetraenyl.

The term "cycloalkyl" refers to a saturated alicyclic moiety having three or more carbon atoms (e.g., from three to six carbon atoms) and which may be optionally benzofused at any available position. This term includes, for example, cyclopropyl, cyclobutyl, cyclopentyl, cyclohexyl, indanyl and tetrahydronaphthyl.

The term "heterocycloalkyl" refers to a saturated heterocyclic moiety having three or more carbon atoms (e.g., from three to six carbon atoms) and one or more heteroatom from the group N, O, S (or oxidised versions thereof) and which may be optionally benzofused at any available position. This term includes, for example, azetidinyl, pyrrolidinyl, tetrahydrofuranyl, piperidinyl, indolinyl and tetrahydroquinolinyl.

The term "cycloalkenyl" refers to an alicyclic moiety having three or more carbon atoms (e.g., from three to six carbon atoms) and having in addition one double bond. This term includes, for example, cyclopentenyl or cyclohexenyl.

The term "heterocycloalkenyl" refers to an alicyclic moiety having from three to six carbon atoms and one or more heteroatoms from the group N, O, S (or oxides thereof) and having in addition one double bond. This term includes, for example, dihydropyranyl.

The term "alkoxy" refers to straight-chain or branched alkyl groups having 1 to 10 carbon atoms as mentioned above, which are attached to the skeleton via an oxygen atom (—O—), for example C1-C10 alkoxy such as methyloxy, ethyloxy, propyloxy, 1-methylethyloxy, butyloxy, 1-methylpropyloxy, 2-methylpropyloxy, 1,1-dimethylethyloxy, isopropoxy, butoxy, isobutoxy, sec-butoxy, tert-butoxy, pentyloxy, isopentyloxy, neopentyloxy, tert-pentyloxy, hexyloxy, isohexyloxy, trifluoromethoxy and neohexyloxy.

The term "halogen" means a halogen atom such as fluorine, chlorine, bromine, or iodine.

The term "optionally substituted" means optionally substituted with one or more of the aforementioned groups (e.g., nitro, amino, CN, —C(O)O-alkyl, alkyl, aryl, heteroaryl, acyl, alkenyl, cycloalkyl, heterocycloalkyl, cycloalkenyl, heterocycloalkenyl, or halogen), at any available position or positions. Examples of optionally substitutions include, but is not limited, to, nitro, amino, CN, C(O)O—C1-6alkyl, halogen, The term "analog" is intended to mean a compound that is similar or comparable, but not identical, to a reference compound, i.e. a compound similar in function, structure, properties and/or appearance to the reference compound. As used herein, an analog is a chemical compound that may be structurally related to another but differs in composition (for example as in the replacement of one atom by an atom of a different element or in the presence of a particular functional group). An analog may be derived from a natural source or be prepared using chemical synthesis.

The term "cancer" is intended to mean any cellular malignancy whose unique trait is the loss of normal controls which results in unregulated growth, lack of differentiation and ability to invade local tissues and metastasize. More specifically, cancer is intended to include, without limitation, prostate cancer, leukemia, hormone dependent cancers, breast cancer, colon cancer, lung cancer, epidermal cancer, liver cancer, esophageal cancer, stomach cancer, cancer of the brain, and cancer of the kidney.

The terms "treatment" or "treating" are intended to mean obtaining a desired pharmacologic and/or physiologic effect, such as inhibition of cancer cell growth or induction of apoptosis of a cancer cell or an improvement in a disease condition in a subject or improvement of a symptom associated with a disease or a medical condition in a subject. The effect may be prophylactic in terms of completely or partially preventing a disease or symptom associated therewith and/or may be therapeutic in terms of a partial or complete cure for a disease and/or the pathophysiologic effect attributable to the disease. "Treatment" as used herein covers any treatment of a disease in a mammal and includes: (a) preventing a disease or condition (such as preventing cancer) from occurring in an individual who may be predisposed to the disease but has not yet been diagnosed as having it; (b) inhibiting the disease, (e.g., arresting its development); or (c) relieving the disease (e.g., reducing symptoms associated with the disease).

The term "biological activity" is intended to mean having the ability to reverse multidrug resistance or inhibit P-gp or MRP1-like activity, having the ability to inhibit cell growth, induce apoptosis, and/or suppress the transforming activity in cancer cells. "Biological activity" also means having therapeutic efficacy and/or the ability to treat cancer or protozoan disease in a subject.

The term "administering" and "administration" is intended to mean a mode of delivery including, without limitation, oral, rectal, parenteral, subcutaneous, intravenous, intramuscular, intraperitoneal, intraarterial, transdermally or via a mucus membrane; the preferred one being orally. One skilled in the art recognizes that suitable forms of oral formulation include, but are not limited to, a tablet, a pill, a capsule, a lozenge, a powder, a sustained release tablet, a liquid, a liquid suspension, a gel, a syrup, a slurry, a suspension, and the like. For example, a daily dosage can be divided into one, two or more doses in a suitable form to be administered at one, two or more times throughout a time period.

The term "therapeutically effective" is intended to mean an amount of a compound sufficient to substantially improve a symptom associated with a disease or a medical condition or to improve, ameliorate or reduce the underlying disease or medical condition. For example, in the treatment of cancer, a compound which decreases, prevents, delays, suppresses, or arrests any symptom of the disease would be therapeutically effective. A therapeutically effective amount of a compound may provide a treatment for a disease such that the onset of the disease is delayed, hindered, or prevented, or the disease symptoms are ameliorated, or the term of the disease is altered.

When the compounds of this invention are administered in combination with other agents, they may be administered prior, sequentially or concurrently to an individual. Alternatively, pharmaceutical compositions according to the present invention may be comprised of a combination of analogs of the present invention, as described herein, and another therapeutic or prophylactic agent known in the art.

It will be understood that a specific "effective amount" for any particular in vivo or in vitro application will depend upon a variety of factors including the activity of the specific compound employed, the age, body weight, general health, sex, and/or diet of the individual, time of administration, route of administration, rate of excretion, drug combination and the severity of the particular disease being treated. For example, the "effective amount" may be the amount of the compounds of the invention necessary to achieve inhibition of MDR and or inhibit promastigotes and amastigotes.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include citric acid, lactic acid, tartaric acid, fatty acids, and the like. Pharmaceutically acceptable salts are known in the art.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

As used herein, the term "pharmaceutically acceptable carrier" includes any and all solvents such as phosphate buffered saline, water, saline, dispersion media, coatings, antibacterial and antifungal agents, isotonic and absorption delaying agents and the like. The use of such media and agents for pharmaceutically active substances is well known in the art. Supplementary active ingredients can also be incorporated into the compositions. The pharmaceutical compositions of the invention can be formulated according to known methods for preparing pharmaceutically useful compositions. Formulations are described in a number of sources which are well known and readily available to those skilled in the art. For example, Remington's Pharmaceutical Science (Martin E W (1995) Easton Pa., Mack Publishing Company, 19th ed.) describes formulations which can be used in connection with the subject invention.

In one embodiment, there is provided a method of synthesizing a compound of formula:

Flavonoid-Linker-Y-Linker-Flavonoid wherein
the flavonoid is flavanone of formula VI and
the residue Linker-Y-Linker- is a group of formula VII;
including the steps of:
a) reacting a flavonoid of formula (VI) with the compound of formula (VII) to form a compound of formula (VIII)

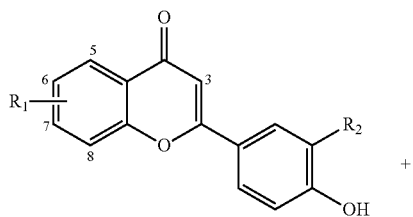

(VI)

-continued

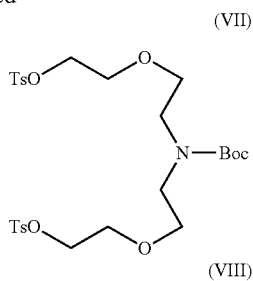
(VII)

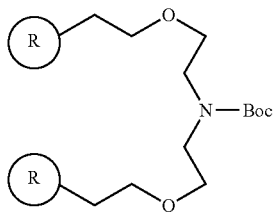
(VIII)

b) reacting a compound of formula (VIII) with acid to form a compound of formula IX wherein R is a flavonoid of formula X

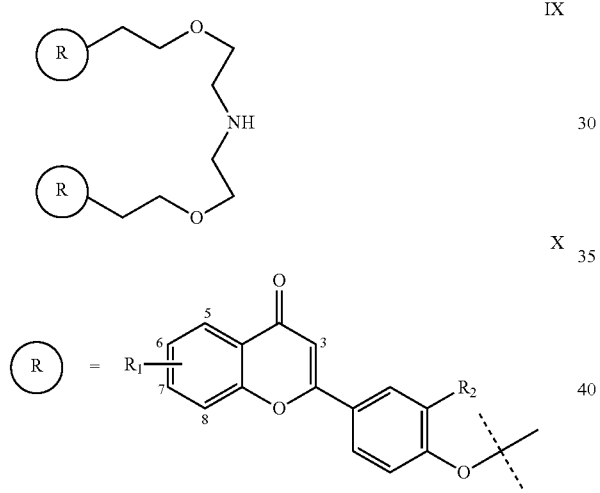

c) reacting a compound of formula IX with a group selected from the group consisting of acyl, alkyl, haloalkyl, alkenyl, alkoxy, cycloalkyl, halo-alkoxy, heterocycloalkyl, cycloalkenyl, heterocycloalkenyl, aryl, aryl alkyl, acyl, acyloxy, arylsulfonyl and alkylsulfonyl group, any of which may be optionally substituted; to form a compound of formula XI:

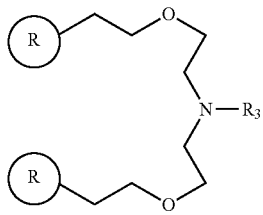

The present description refers to a number of chemical terms and abbreviations used by those skilled in the art. Nevertheless, definitions of selected terms are provided for clarity and consistency: PEG: Polyethylene glycol; DMF: Dimethylformamide; PEM: peritoneal elicited macrophage; SSG: sodium stibogluconate; PBS: phosphate-buffered saline; ACN: Acetonitrile; PMS: phenazine methosulfate; $OsO_4$: Osmium tetroxide; NMO: N-Methylmorpholine-N-Oxide; $Ac_2O$:Acetic anhydride; Py: Pyridine; TFA: Trifluoroacetic acid; HBTU: O-(Benzotriazol-1-yl)-N,N,N',N'-tetramethyluronium hexa-fluorophosphate; DMEM: Dulbecco's Modified Eagle's Medium; HOBT: 1 Hydroxybenzotriazole; DIPEA: N,N-Diisopropylethylamine; DMAP: 4-Dimethylaminopyridine; Bn: Benzyl; MeOH: Methanol; TLC: Thin Layer Chromatography; NMR: Nuclear Magnetic Resonance; MS: Mass Spectroscopy; ESI: Electrospray Ionization; ND: Not determined. FAB: Fast Atom Bombardment; SPE: Solid-Phase Extraction; DMSO: Dimethyl Sulfoxide; THF: Tetrahydrofuran.

Methods of Synthesis

The compounds of the invention can be prepared according to the synthetic routes outlined in Schemes 1, 2 and 3 by the methods described in detail herein.

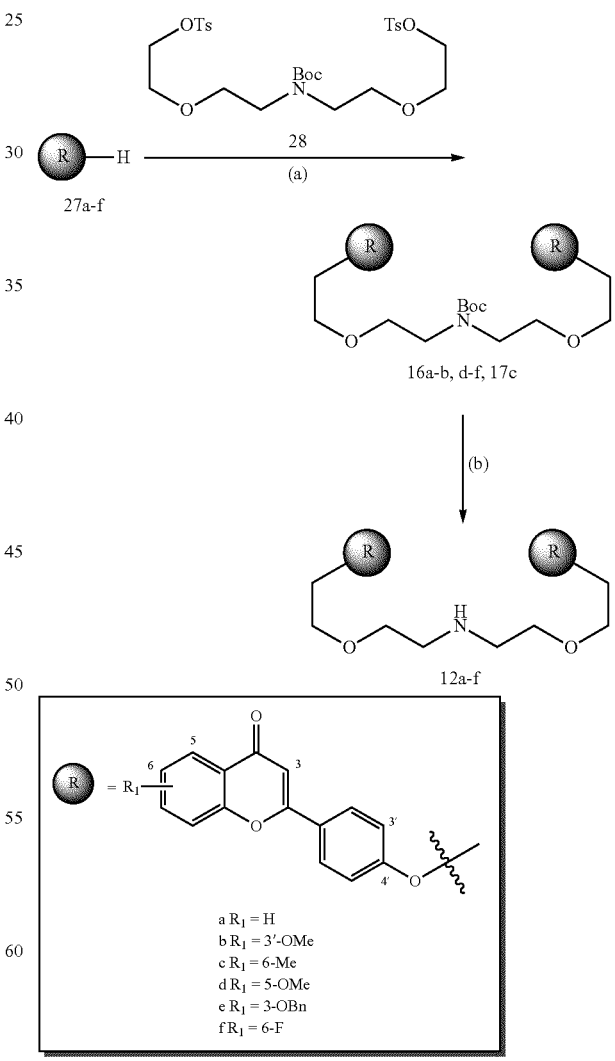

[a]Reagents and conditions: (a) $K_2CO_3$, DMF, reflux, 2 h; (b) trifluoroacetic acid, $CH_2Cl_2$, 0° C. to r.t., 2 h;

Scheme 2. Synthesis of compounds 13-15, 18-26, and 33-62.[a]
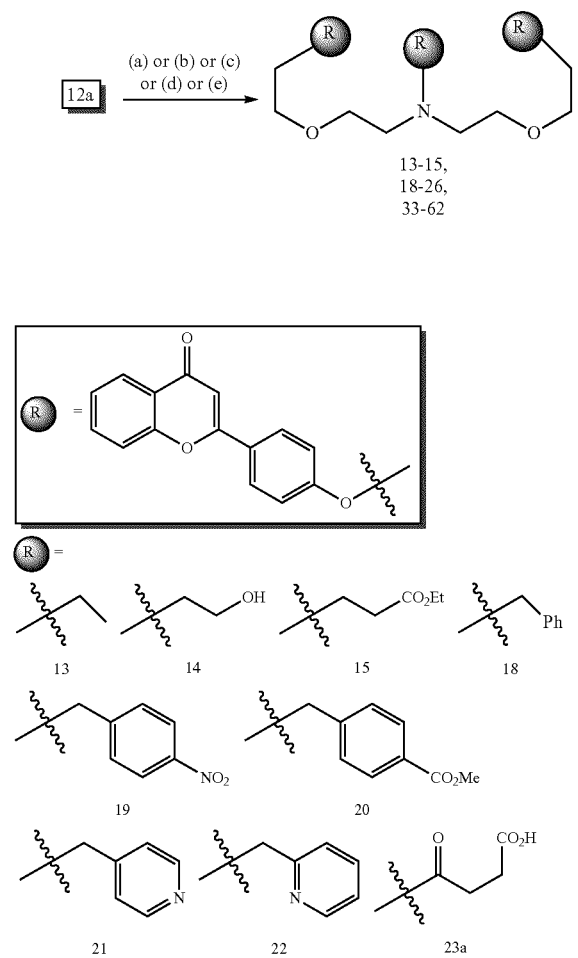
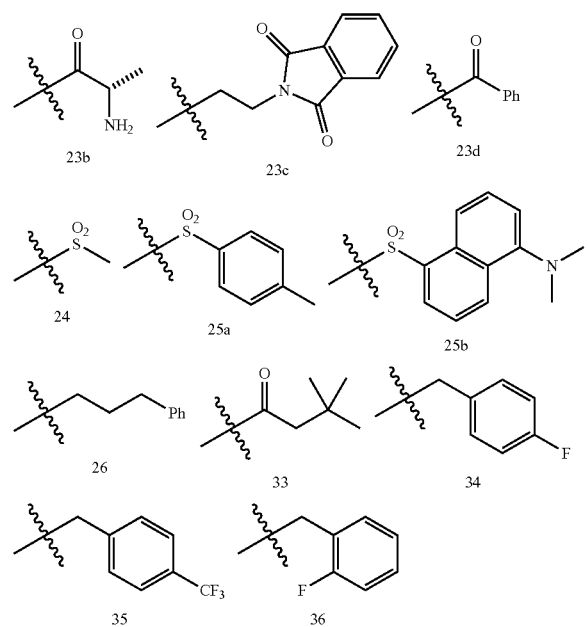
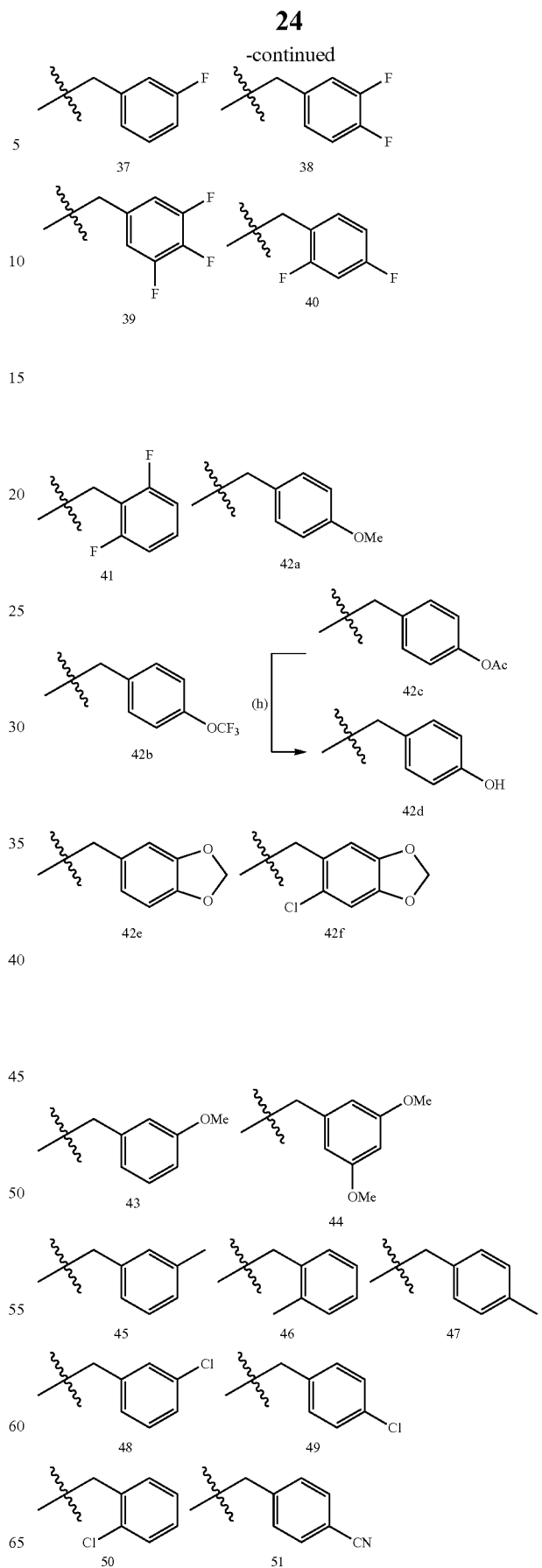

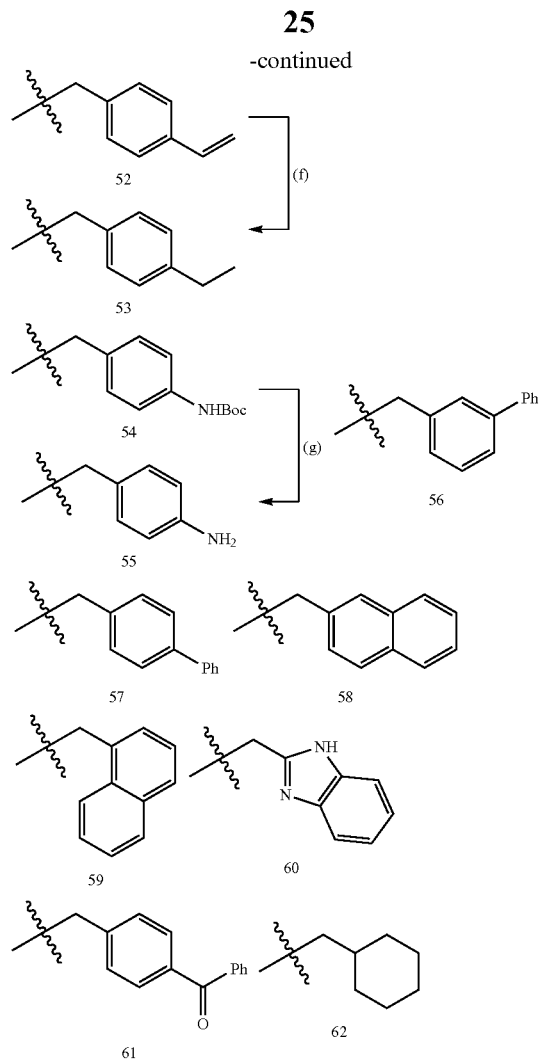

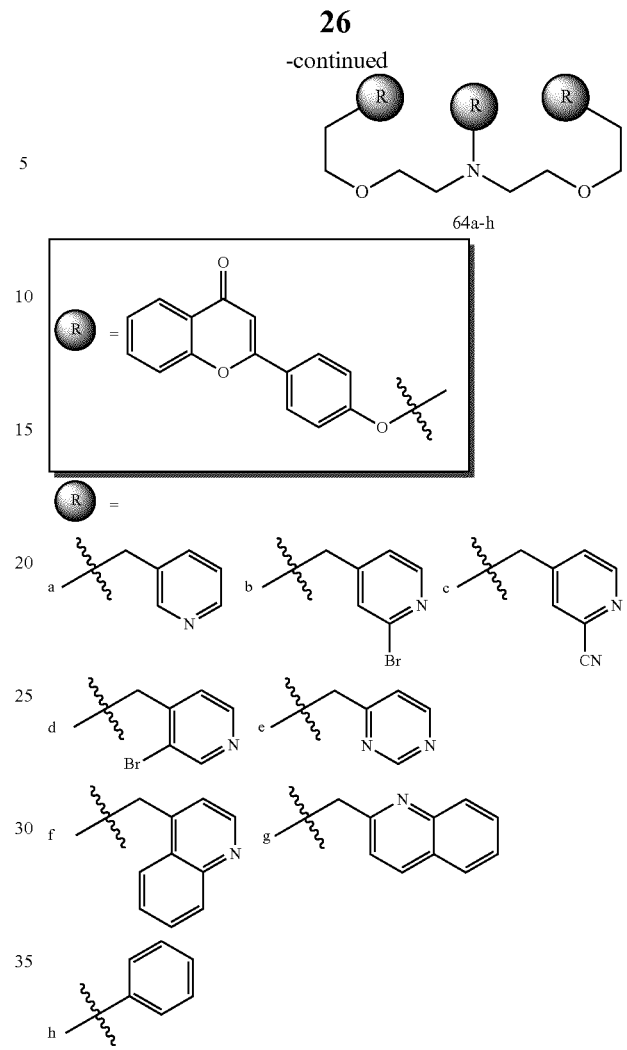

[a]Reagents and conditions: (a) for compounds 13-15, 18-22, 23c, 26, 34-52, 54, 56-62, K₂CO₃, RX, ACN or DMF, reflux, 3 h.; (b) for compound 23a, succinic anhydride, pyridine, r.t., 4 h. (c) for compounds 24, 25a and 25b, RSO₂Cl, pyridine, 0° C. to r.t.; (d) for compound 23b, coupling with t-Boc-alalnine followed by acid hydrolysis, (e) for compounds 23d and 33, RCOCl, pyridine, 0° C. to r.t.; (f) for compounds 53, 52, H₂, 10% Pd/C, CHCl₃, r.t., 4 h; (g) for compound 55, 54, TFA, CH₂Cl₂, r.t.; (h) for compound 42d, 42c, KOH, MeOH, r.t. 2 h.

[a]Reagents and conditions: (a) for compound 63a-g, RX, K₂CO₃, Acetone, reflux, 3 h.; (b) 27a, DIAD, PPh₃, THF, reflux, 12 h.

Scheme 3. Synthesis of compounds 64a-h.[a]

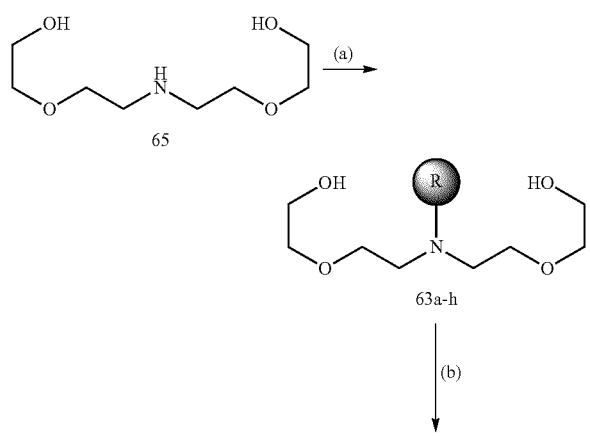

The designed flavonoid dimers were synthesized as summarized in Schemes 1-3. There are two synthetic pathways that can lead to the desired compounds. The first approach (Scheme 1 and 2) involves the attachment of two flavones moieties at the both side of the N-Boc protected amino linker. Then structural modification at the amino group furnishes the desired compounds. The other pathway (Scheme 3) involved the initial structural functionalization at the amino group of the linker. Two flavones moieties were then attached at the both side the linker giving the desired compounds. Both synthetic pathways offer advantages and flexibility to access desired flavonoid dimers for SAR study.

As depicted in Scheme 1, reacting the N-Boc protected ditosylate 28 with corresponding 4'-hydroxyflavones 27, prepared as previously reported, in DMF under basic condition at refluxing temperature, the desired N-Boc protected flavonoid dimers 16 and 17 with various substituents on the flavones rings were obtained in reasonable yield. Their dimeric nature was evident from the high-resolution mass spectrum. Treatment of these compounds (16a-b, d-f, 17c) with trifluoroacetic acid (TFA) in CH₂Cl₂ followed by extraction at basic pH led to the corresponding flavonoid dimers (12a-f) with secondary amino group at the linker region in high yield. It should be mentioned that hydrochloride salt of these compounds, which are water soluble, were obtained simply by treatment with concentrated hydrochloric acid followed by evaporation to dryness.

With the requisite amino flavonoid dimer 12a in hand, we embarked on the structural functionalization at the amino group of the linker to other functional group, namely sulfonamide, amide and tertiary amine (Scheme 2). Treatment of 12a with various sulfonyl chlorides in pyridine at 0° C. afforded sulfonamide derivatives (24,25a-b) in reasonable good yield. Amide derivatives (23d, 33) were also obtained under similar condition in high yield by mixing 12a with corresponding acid chlorides. Amide derivative 23a was furnished by treatment of 12a with succinic anhydride in pyridine at room temperature. Amide derivative 23b was prepared by in two steps from commercially available Boc-Ala-OH followed by acid hydrolysis using TFA. For tertiary amine derivatives 13-15, 18-22, 23c, 26, 34-41,42a-c, 42e-f, 43-52, 54, 56-62, Treatment of 12a with corresponding alkyl halides or aryl halides under basic medium using ACN or DMF at refluxing temperature afforded the desired flavonoid dimers at reasonable yield. Compound 42d was obtained by mixing compound 42c with KOH solution in methanol at room temperature. Treatment of compound 52 with 10% Pd/C catalyst under hydrogen atmosphere at balloon pressure afforded compound 53 in high yield. Compound 55 was also obtained by acid hydrolysis of compound 54 using TFA.

In order to improve the reaction yield, we have also developed another synthetic pathway for making flavonoid dimers. As shown in Scheme 3, treatment of amino diol 65 with various aryl halides under basic medium in refluxing acetone afforded diols 63. Subjecting flavones 27a with corresponding diols 63 under Mitsunobu reaction condition furnished flavonoid dimers 64 in good yield.

EXPERIMENTAL METHODS

General Methods. All NMR spectra were recorded on a Bruker MHz DPX400 spectrometer at 400.13 MHz for $^1$H and 100.62 MHz for $^{13}$C. All NMR measurements were carried out at room temperature and the chemical shifts are reported as parts per million (ppm) in unit relative to the resonance of $CDCl_3$ (7.26 ppm in the $^1$H, 77.0 ppm for the central line of the triplet in the $^{13}$C modes, respectively). Low-resolution and high-resolution mass spectra were obtained on a Micromass Q-TOF-2 by electron spray ionization (ESI) mode or on Finnigan MAT95 ST by electron ionization (EI) mode. Melting points were measured using Electrothermal IA9100 digital melting point apparatus and were uncorrected. All reagents and solvents were reagent grade and were used without further purification unless otherwise stated. The plates used for thin-layer chromatography (TLC) were E. Merck Silica Gel 60F$_{254}$ (0.25-mm thickness) and they were visualized under short (254-nm) and long (365-nm) UV light. Chromatographic purifications were carried out using MN silica gel 60 (230-400 mesh). Substituted 4'-hydroxyflavones 27a-f were prepared as we reported previously. {Chan, K. F.; Zhao, Y.; Chow, T. W.; Yan, C. S.; Ma, D. L.; Burkett, B. A.; Wong, I. L.; Chow, L. M.; Chan, T. H. ChemMedChem 2009, 4, 594.} Ditosylate 28 and dihydroxylamine 63h were prepared according to the literature report. {Bordunov, A. V. H., P. C.; Bradshaw, J. S.; Dailey, N. K.; Kou, X.; Zhang, X. X.; Izatt, R. M. J Organic Chem 1995, 60, 6097; Maeda, H. F., S.; Nakatsuji, Y.; Okahara, M. Tetrahedron 1982, 38, 3359.}

Pentamidine, amphotericin B, paromomycin, luteolin and quercetin were purchased from Sigma. Miltefosine was from Cayman.

Materials for Biological Studies. Dimethyl sulfoxide (DMSO), paclitaxel ($C_{47}H_{51}NO_{14}$), doxorubicin ($C_{27}H_{20}NO_{11}$), vinblastine ($C_{46}H_{55}N_4O_9$), vincristine ($C_{46}H_{56}N_4O_{10}$), verapamil ($C_{27}H_{30}N_2O_4$), mitoxantrone ($C_{22}H_{28}N_4O_6$) and PMS were purchased from Sigma-Aldrich. Dulbecco's Modified Eagle's Medium, Roswell Park Memorial Institute (RPM') 1640 medium, trypsin-ethylenediaminetetraacetic acid (EDTA) and penicillin/streptomycin were purchased from Gibco BRL. The fetal bovine serum (FBS) was purchased from HyClone Laboratories. 3-(4,5-Dimethylthiazol-2-yl)-5-[3-(carboxymethoxy)phenyl]-2-(4-sulfo-phenyl)-2H-tetrazolium (MTS) was purchased from Promega. The human breast cancer cell lines MDA435/LCC6 and MDA435/LCC6MDR were kindly provided by Dr. Robert Clarke (Georgetown University). The human ovarian carcinoma cell lines 2008/P and 2008/MRP1 were generous gifts from Prof. P. Borst (The Netherlands Cancer Institute, Amsterdam, Netherlands). The L929 cell line was purchased from ATCC.

Cell Lines and Cell Culture. Promastigotes of *Leishmania donovani* (wild type LdAG83, pentamidine-resistant LdAG83-PentR50, and SSG-resistant Ld39) and *Leishmania major* [MHOM/IL/67/JERICHO II (Lm50122), from ATCC] were used in this study. Both strains were cultured in Schneider's *Drosophila* Medium (Invitrogen), pH 6.9 supplemented with 10% (v/v) heat inactivated fetal bovine serum (Hyclone) with 4 mM glutamine (Sigma) and 25 μg/mL gentamicin solution (Invitrogen) at 27° C. for 4 days (Chow, L. M.; et al. *Mol Biochem Parasitol* 1993, 60, 195-208).

Promastigotes of LdAG83-PentR50 (pentamidine-resistant, $IC_{50}$ of pentamidine=74.7 μM) were selected by gradually increasing the pentamidine (Sigma) pressure to the wild-type promastigotes (Wong, I. L. et al. *Leishmania. J Antimicrob Chemother* 2009, 63, 1179-1190). Ld39 was sodium stibogluconate resistant strain and the SSG IC50 was 7090 μM. No pentamidine or sodium stibogluconate was added to the *L. donovani* wild type (LdAG83) and *L. major* wild type (Lm50122). The mouse macrophage cell line, Raw264.7, was used for the determination of the relative toxicity of the compounds of the invention. MDA435/LCC6, MDA435/LCC6MDR and L929 cell lines were cultured in supplemented DMEM media with 10% heat inactivated FBS and 100 U/mL penicillin and 100 μg/mL of streptomycin. 2008/P and 2008/MRP1 cells were cultured in RPMI 1640 medium containing heat inactivated 10% FBS and 100 U/mL penicillin and 100 μg/mL of streptomycin. They were maintained at 37° C. in a humidified atmosphere with 5% $CO_2$. The cells were split constantly after a confluent monolayer has been formed. To split cells, the plate was washed briefly with PBS, treated with 0.05% trypsin-EDTA and harvested by centrifugation.

In Vitro Anti-Promastigote Activity. The viability of promastigotes was determined by the Cell Titer 96° Aqueous Assay (Promega) that employs a tetrazolium compound (MTS, 2-(4,5-Dimethylthiazol-2-yl-)-5-[3-(carboxymethoxy)phenyl]-2-(4-sulfophenyl)-2H-tetrazolium) and electron coupling reagent, phenazine methosulfate (PMS).[7] Promastigotes were seeded into 96-well flat bottom microtiter plate at $1\times10^5$ cells per well in a final volume of 100 μL medium and incubated with a series concentration of synthetic flavonoid dimers or known antileishmanials. The parasites were incubated at 27° C. for 72 hrs. Fresh solution of 2 mg/mL MTS and 0.92 mg/mL PMS were prepared in a ratio of 20:1 (MTS:PMS). After 72 hrs incubation, 10 μL of MTS:PMS mixture was added into each well of microtiter plate. The plate was then incubated at 27° C. for 4 hrs for color development. After 4 hrs incubation, the OD values were determined at 490 nm using automatic microtiter plate reader (Bio-Rad). The results were presented as % of survivors (OD value with test compound divided by that of untreated control).

In vitro Anti-amastigote Activity. Peritoneal elicited macrophages (PEM) from mouse were obtained as previously described. A round cover slip (12 mm in diameter) was placed into each well of 24-well culture plate. Mouse macrophages were resuspended in supplemented DMEM media containing 10% heat inactivated fetal bovine serum (v/v), 100 U/mL penicillin and 100 μg/mL streptomycin and seeded into each well at a cell density of $1\times10^5$ cells per 500 μL. Macrophages were allowed to attach overnight and the non-adherent cells were removed by gentle washing twice with unsupplemented DMEM media. The adherent macrophages were infected with late-log promastigotes at a parasite-to-macrophage ratio of 20:1 overnight at 37° C. with 5% $CO_2$. Non-internalized promastigotes were removed by washing with unsupplemented DMEM media for two times. Infected macrophages were further incubated in 500 μL supplemented DMEM media in the presence or absence of flavonoid dimers or known antileishmanials for 72 hrs at 37° C. After incubation, the cover slips were stained with Giemsa and the amastigotes inside each macrophage (100 macrophages per treatment) were counted under microscope. The percentage of macrophages infected and number of amastigotes per 100 macrophages was enumerated.

In vitro Cytotoxicity Assays (a) Mouse Macrophage Raw 264.7 and Primary Mouse PEM Cells. The cytotoxicity assay of reference antileishmanial compounds and the compounds of this invention was performed against mouse macrophage cell line, Raw 264.7 and primary mouse PEM cells in order to calculate the therapeutic index ($IC_{50}$ value for cytotoxicity of the compounds divided by $IC_{50}$ value for antileishmanial activity of the compounds). The cells were grown in supplemented DMEM media in an atmosphere of 95% air with 5% $CO_2$ at 37° C. In brief, Raw264.7 cells and PEM cells were seeded into 96-well flat bottom microtiter plate at $1\times10^4$ cells and $2\times10^4$ cells per well in a final volume of 100 μL media, respectively. A graded dose of flavonoid dimers or antileishmanials was added into wells. The plate was incubated at 37° C. for 72 hrs at the atmosphere 5% $CO_2$ in the air. The % of survivors was determined.

(b) Tumor Cell Line Cytotoxicity. The tumor cytotoxicity assays of flavonoid dimers were performed against LCC6, LCC6MDR and L929 cell lines. The cells were grown in supplemented DMEM media in an atmosphere of 95% air and 5% $CO_2$ at 37° C. In brief, LCC6, LCC6MDR and L929 cells were seeded into 96-well flat bottom microtiter plate at $1\times10^4$ cells per well in a final volume of 100 μL media, respectively. A graded dose of flavonoid dimers was added into wells. The plate was incubated at 37° C. for 72 hrs at the atmosphere 5% $CO_2$ in the air. The % of survivors was determined.

Cell Proliferation Assay. 6,000 cells of LCC6 or LCC6MDR and anticancer drugs (paclitaxel, vinblastine, vincristine, doxorubicin and mitoxantrone) were mixed with or without modulators to a final volume of 200 μL in each well of 96-well plates. 4,000 cells of 2008/P or 2008/MRP1 and doxorubicin were co-incubated with or without 18 to a final volume of 200 μL. The plates were then incubated for 5 days at 37° C. After 5 days, the % of survival or viability was determined by MTS according to procedures reported previously.[37] The results were represented as mean±standard error of mean. $IC_{50}$ values were calculated from the dose-response curves of MTS assays (Prism 4.0).

Doxorubicin accumulation. The Doxorubicin accumulation assay was carried out according to the reported procedures (Wong, I. L.; et al. *J Med Chem* 2009, 52, 5311-5322). Briefly, $1\times10^6$ cells of LCC6 and LCC6MDR cells were added in an Eppendorf and incubated with 20 μM doxorubicin and different concentration of compound 18 or verapamil for 150 min at 37° C. A 0.4% of DMSO was used as a negative control. After incubation, the cells were washed and lysed with olysis buffer (0.75 M HCl, 0.2% Triton-X100 in isopropanol). The fluorescence level of Doxorubycin in the lysate was determined by fluorescence spectrophotometer (BMG Technologies) using an excitation and an emission wavelength pair of 460 nm and 610 nm.

Influx and Efflux Studies. To measure the Doxorubycin cellular influx, LCC6 and LCC6MDR cells were co-incubated with Doxorubycin (8 μM) and compound 18 (1 or 3 μM) in the supplemented DMEM media at 37° C. 0.15% of DMSO acted as a negative control. The cells were harvested after 0, 15, 30, 45, 75 min for determining the intracellular Doxorubycin concentration as described previously. To measure Doxorubycin efflux, LCC6 and LCC6MDR cells were incubated in supplemented DMEM containing 20 μM Doxorubycin for 2 hrs at 37° C. The cells were then washed and further incubated in the presence or absence of compound 18 (1 or 3 μM). At 0, 15, 30, 60, 90, 120, 150 and 180 min, the cells were harvested for measuring the intracellular Doxorubycin concentration.

General Procedure I for the Preparation of Flavonoid Dimers 16a-b, 16d-f and 17c: To a round-bottom flask was charged with corresponding 4'-hydroxyflavones 27a-f (2 equiv.), ditosylate 28 (1 equiv.), $K_2CO_3$ (2.5 equiv.) and DMF. The reaction mixture was stirred at refluxing temperature for 2 hr. When TLC indicated complete consumption of starting material, the reaction mixture was poured into a separating funnel containing water. The mixture was continuously extracted with $CH_2Cl_2$. If the mixture could not be separated into two layers, small amount of 1M HCl was added. The combined organic layers were dried over $MgSO_4$, filtered and evaporated to give a brown crude reaction mixture. Purification of the flavonoid dimers were performed by flash column chromatography on silica gel with 10-20% acetone in $CH_2Cl_2$ as eluent to furnish desired product.

Example 1

1,13-Bis[4'-(4H-chromen-4-on-2-yl)phenyl]-N-(tert-butyloxycarbonyl)-1,4,10,13-tetraoxa-7-azamidecane (16a). The titled compound 16a was obtained from flavone 27a (4.8 g, 20 mmol), ditosylate 28 (6.1 g, 10 mmol), $K_2CO_3$ (3.5 g) and DMF (30 mL) as a white foam (5.2 g, 70%) according to the general procedure described above: $^1$H NMR (CDCl$_3$) δ 1.42 (s, 9H), 3.45 (s, 4H), 3.62 (s, 4H), 3.69 (s, 4H), 4.08 (s, 4H), 6.60 (s, 2H), 6.94 (d, J=8.4 Hz, 4H), 7.30 (d, J=6.4 Hz, 2H), 7.43 (d, J=8.0 Hz, 2H), 7.57 (d, J=6.4 Hz, 2H), 7.75 (d, J=8.4 Hz, 4H), 8.12 (d, J=7.2 Hz, 2H); $^{13}$C NMR (CDCl$_3$) δ 28.4, 47.6, 47.9, 67.5, 69.1, 69.2, 69.9, 70.1, 79.6, 106.0, 114.9, 117.9, 123.8, 123.9, 125.0, 125.4, 127.8, 133.5, 155.4, 156.0, 161.5, 163.1, 178.1; LRMS (ESI) m/z 734 (M$^+$+H, 77), 756 (M$^+$+Na, 100); HRMS (ESI) Calcd for $C_{43}H_{44}NO_{10}$ (M$^+$+H) 734.2965, found 734.2979.

Example 2

1,13-Bis[4'-((4H-chromen-4-on-2-yl)-3'-methoxyphenyl)]-7-(tert-butylformyl)-1,4,10,13-tetraoxa-7-azamidecane (16b). The titled compound 16b was obtained from 4'-hydroxyflavone 27b (0.18 g, 0.67 mmol), ditosylate 28 (0.20 g, 0.33 mmol), $K_2CO_3$ (0.12 g) and DMF (6 mL) as a white foam (0.14 g, 53%) according to the general procedure I described above: $^1$H NMR (CDCl$_3$) δ 1.40 (s, 9H), 3.45 (s, 4H), 3.61 (s, 4H), 3.79 (s, 4H), 3.87 (s, 6H), 4.13 (s, 4H), 6.63 (s, 2H), 6.89 (d, J=6.4 Hz, 2H), 7.30 (d, J=6.4 Hz, 2H), 7.43 (d, J=8.0 Hz, 2H), 7.57 (d, J=6.4 Hz, 2H), 7.75 (d, J=8.4 Hz, 4H), 8.12 (d, J=7.2 Hz, 2H); $^{13}$C NMR (CDCl$_3$) δ 28.4, 47.6, 47.9, 56.0, 68.4, 69.0, 69.2, 69.9, 70.2, 79.5, 106.3, 109.1, 112.8, 117.9, 119.7, 123.7, 124.3, 125.0, 125.4, 133.5, 149.5, 151.4, 155.4, 156.0, 163.1, 178.1; LRMS (ESI) m/z 794 (M$^+$+H, 27), 816 (M$^+$+Na, 100); HRMS (ESI) Calcd for C$_{45}$H$_{48}$NO$_{12}$(M$^+$+H) 794.3177, found 794.3170.

Example 3

1,13-Bis[4'-((5-methoxy)-4H-chromen-4-on-2-yl)phenyl]-7-(tert-butyloxycarbonyl)-1,4,10,13-tetraoxa-7-azamidecane (16d). The titled compound 16d was obtained from 4'-hydroxyflavone 27d (80 mg, 0.30 mmol), ditosylate 28 (90 mg, 0.15 mmol), K$_2$CO$_3$ (60 mg) and DMF (5 mL) as a white foam (69 mg, 58%) according to the general procedure I described above: $^1$H NMR (CDCl$_3$) δ 1.41 (s, 9H), 3.45 (t, J=6.8 Hz, 4H), 3.63 (s, 4H), 3.71 (s, 4H), 3.92 (s, 6H), 4.09 (s, 4H), 6.55 (s, 2H), 7.73 (d, J=7.6 Hz, 2H), 6.93 (d, J=8.0 Hz, 4H), 7.02 (d, J=8.0 Hz, 2H), 7.47 (dd, J=7.6, 8.0 Hz, 2H), 7.74 (d, J=8.0 Hz, 4H); LRMS (ESI) m/z 794 (M$^+$+H, 35), 816 (M$^+$+Na, 100); HRMS (ESI) Calcd for C$_{45}$H$_{48}$NO$_{12}$(M$^+$+H) 794.3177, found 794.3175.

Example 4

1,13-Bis[4'-((5-benzyloxy)-4H-chromen-4-on-2-yl)phenyl]-7-(tert-butyloxycarbonyl)-1,4,10,13-tetraoxa-7-azamidecane (16e).

The titled compound 16e was obtained from 4'-hydroxyflavone 27e (0.19 g, 0.55 mmol), ditosylate 28 (0.17 g, 0.28 mmol), K$_2$CO$_3$ (0.10 g) and DMF (6 mL) as a white foam (0.13 g, 49%) according to the general procedure I described above: $^1$H NMR (CDCl$_3$) δ 1.45 (s, 9H), 3.50 (t, J=6.8 Hz, 4H), 3.60 (s, 4H), 3.79 (s, 4H), 4.10 (s, 4H), 5.07 (s, 4H), 6.91 (d, J=8.8 Hz, 4H), 7.22-7.41 (m, 14H), 7.55 (dd, J=8.0, 8.4 Hz, 2H), 7.98 (d, J=8.8 Hz, 4H), 8.20 (d, J=8.0 Hz, 2H); $^{13}$C NMR (CDCl$_3$) δ 28.4, 47.7, 47.9, 67.5, 69.1, 69.3, 69.9, 70.1, 73.8, 79.6, 114.4, 117.9, 123.3, 124.0, 124.5, 125.5, 128.0, 128.2, 128.7, 129.0, 130.4, 133.2, 136.7, 139.2, 155.0, 155.4, 156.0, 160.6, 174.8; LRMS (ESI) m/z 946 (M$^+$+H, 25), 968 (M$^+$+Na, 100); HRMS (ESI) Calcd for C$_{57}$H$_{56}$NO$_{12}$(M$^+$+H) 946.3803, found 946.3838.

Example 5

1,13-Bis[4'-((5-hydroxy)-4H-chromen-4-on-2-yl)phenyl]-7-(tert-butyloxycarbonyl)-1,4,10,13-tetraoxa-7-azamidecane (16f).

The titled compound 16f was obtained from 4'-hydroxyflavone 27f (3.09 g, 12.1 mmol), ditosylate 28 (3.60 g, 5.98 mmol), K$_2$CO$_3$ (1.74 g) and DMF (20 mL) as a white foam (2.41 g, 52%) according to the general procedure I described above: $^1$H NMR (CDCl$_3$) δ 1.47 (s, 9H), 3.51 (s, 4H), 3.69 (s, 4H), 3.84 (s, 4H), 4.17 (s, 4H), 6.68 9s, 2H), 7.00 (d, J=8.8 Hz, 4H), 7.39 (ddd, J=2.0, 8.4, 8.4 Hz, 2H), 7.50 (dd, J=4.4, 9.2 Hz, 2 H), 7.79 (d, J=8.8 Hz, 4H), 7.81 (dd, J=4.4, 8.8 Hz, 2H); $^{13}$C NMR (CDCl$_3$) δ 28.4, 47.7, 47.9, 67.5, 69.1, 69.3, 69.9, 70.1, 73.8, 79.6, 105.4, 110.6 (d, J=23.6 Hz, C5), 115.1, 119.9 (d, J=7.8 Hz, 010), 121.7 (d, J=25.2 Hz, C7), 123.8, 125.0 (d, J=7.8 Hz, C8), 127.9, 152.2 (d, J=1.5 Hz, C9), 159.5 (d, J=245.3 Hz, C6), 161.7, 163.5, 177.4; LRMS (ESI) m/z 770 (M$^+$+H, 100), 792 (M$^+$+Na, 68); HRMS (ESI) Calcd for C$_{43}$H$_{42}$NO$_{10}$F$_2$(M$^+$+H) 770.2777, found 770.2807.

Example 6

1,13-Bis[4'-((3-benzyloxy)-4H-chromen-4-on-2-yl)phenyl]-7-(tert-butyloxycarbonyl)-1,4,10,13-tetraoxa-7-azamidecane (16g). The titled compound 16g was obtained from 4'-hydroxyflavone 27g (0.19 g, 0.55 mmol), ditosylate 28 (0.17 g, 0.28 mmol), K$_2$CO$_3$ (0.10 g) and DMF (6 mL) as a white foam (0.13 g, 49%) according to the general procedure I described above: $^1$H NMR (CDCl$_3$) δ 1.45 (s, 9H), 3.50 (t, J=6.8 Hz, 4H), 3.60 (s, 4H), 3.79 (s, 4H), 4.10 (s, 4H), 5.07 (s, 4H), 6.91 (d, J=8.8 Hz, 4H), 7.22-7.41 (m, 14H), 7.55 (dd, J=8.0, 8.4 Hz, 2H), 7.98 (d, J=8.8 Hz, 4H), 8.20 (d, J=8.0 Hz, 2H); $^{13}$C NMR (CDCl$_3$) δ 28.4, 47.7, 47.9, 67.5, 69.1, 69.3, 69.9, 70.1, 73.8, 79.6, 114.3, 117.9, 123.3, 124.0, 124.5, 125.5, 128.0, 128.2, 128.7, 129.0, 130.4, 133.2, 136.7, 139.2, 155.0, 155.4, 156.0, 160.6, 174.8; LRMS (ESI) m/z 946 (M$^+$+H, 25), 968 (M$^+$+Na, 100); HRMS (ESI) Calcd for C$_{57}$H$_{56}$NO$_{12}$(M$^+$+H) 946.3803, found 946.3838.

Example 7

1,13-Bis[4'-((6-methyl)-4H-chromen-4-on-2-yl)phenyl]-N-(tert-butyloxycarbonyl)-1,4,10,13-tetraoxa-7-azamidecane (17c). The titled compound 17c was obtained from flavone 27c (0.12 g, 0.48 mmol), ditosylate 28 (0.15 g, 0.25 mmol), K$_2$CO$_3$ (0.09 g) and DMF (6 mL) as a white foam (90 mg, 47%) according to the general procedure described above: $^1$H NMR (CDCl$_3$) δ 1.42 (s, 9H), 2.36 (s, 6H), 3.46 (t, J=6.8 Hz, 4H), 3.64 (t, J=3.6 Hz, 4H), 3.78 (s, 4H), 4.091 (s, 4H), 6.62 (s, 2H), 6.93 (d, J=8.4 Hz, 4H), 7.31-7.39 (m, 4H), 7.75 (d, J=8.4 Hz, 4H), 7.89 (s, 2H); $^{13}$C NMR (CDCl$_3$) δ 20.9, 28.5, 31.4, 47.8, 48.0, 67.6, 69.1, 70.0, 70.2, 79.7, 105.8, 115.0, 117.7, 123.3, 124.1, 124.9, 128.0, 134.9, 135.1, 154.4, 155.5, 161.7, 162.5, 163.3, 178.3; LRMS (ESI) m/z 762 (M$^+$+H, 95), 784 (M$^+$+Na, 100); HRMS (ESI) Calcd for C$_{45}$H$_{48}$NO$_{10}$(M$^+$+H) 762.3278, found 762.3289.

General Procedure II for the Preparation of Flavonoid Dimers 12a-f: To a round-bottom was charged with N-Boc protected flavonoid dimers 16 or 17 and CH$_2$Cl$_2$, the solution was cooled to 0° C. using an ice bath. Equal volume of TFA was then added dropwise and the reaction mixture was stirred vigorously at 0° C. for 1 hr and r.t. for another 1 hr. After stirring, the reaction was quenched by pouring into a conical flask containing water. The resultant mixture was basified to pH 10 by using potassium hydroxide solution. The mixture was continuously extracted with CH$_2$Cl$_2$. The combined organic layers were dried over MgSO$_4$, filtered and evaporated to give the desired product.

Example 8

1,13-Bis[4'-(4H-chromen-4-on-2-yl)phenyl]-1,4,10,13-tetraoxa-7-azamidecane (12a). To a round-bottom was charged with 16a (5.10 g, 6.95 mmol), TFA (20 mL) and CH$_2$Cl$_2$ (20 mL). The solution was cooled to 0° C. using an ice bath. Equal volume of TFA was then added dropwise and the reaction mixture was stirred vigorously at 0° C. for 1 hr and r.t. for another 1 hr. After stirring, the reaction was quenched by pouring into a conical flask containing water. The resultant mixture was basified to pH 10 by using potassium hydroxide solution. The mixture was continuously extracted with CH$_2$Cl$_2$. The combined organic layers were dried over MgSO$_4$, filtered and evaporated to give the desired product as a pale brown oil (4.30 g, 98%). $^1$H NMR (CDCl$_3$)

δ 1.95 (br, 1H), 2.83-2.87 (m, 4H), 3.65-3.69 (m, 4H), 3.82 (t, J=4.8 Hz, 4H), 4.14 (t, J=4.8 Hz, 4H), 6.66 (s, 2H), 6.97 (d, J=8.6 Hz, 4H), 7.34 (dd, J=7.2, 8.0 Hz, 2H), 7.47 (d, J=8.4 Hz, 2H), 7.61 (dd, J=7.2, 8.0 Hz, 2H), 7.80 (d, J=8.6 Hz, 4H), 8.15 (dd, J=1.2, 8.0 Hz, 2H); $^{13}$C NMR (CDCl$_3$) δ 49.2, 67.5, 69.3, 70.9, 106.1, 114.9, 117.9, 123.8, 124.0, 125.0, 125.5, 127.8, 133.5, 156.0, 161.5, 163.1, 178.2; LRMS (ESI) m/z 634 (M$^+$+H, 100); HRMS (ESI) Calcd for $C_{38}H_{36}NO_8$(M$^+$+H) 634.2441, found 634.2418.

Example 9

1,13-Bis[4'-((4H-chromen-4-on-2-yl)-3'-methoxyphenyl)]-1,4,10,13-tetraoxa-7-azamidecane (12b). The titled compound 12b was obtained from 16b (0.12 g, 0.15 mmol), TFA (4 mL) and CH$_2$Cl$_2$ (4 mL) as a pale brown oil (95 mg, 91%) according to the general procedure II described above: $^1$H NMR (CDCl$_3$) δ 2.13 (br, 1H), 2.79-2.82 (m, 4H), 3.63-3.65 (m, 4H), 3.83-3.84 (m, 4H), 3.89 (s, 6H), 4.16-4.19 (m, 4H), 6.65 (s, 1H), 6.66 (s, 1H), 6.91-6.94 (m, 2H), 7.29-7.33 (m, 4H), 7.42-7.48 (m, 4H), 7.52-7.58 (m, 2H), 8.11-8.13 (m, 2H); $^{13}$C NMR (CDCl$_3$) δ 49.1, 56.0, 68.3, 69.2, 70.9, 79.6, 106.3, 109.2, 112.8, 117.9, 119.7, 123.8, 124.3, 125.0, 125.5, 133.5, 149.5, 151.3, 156.0, 163.1, 178.2; LRMS (ESI) m/z 694 (M$^+$+H, 100), 716 (M$^+$+Na, 19); HRMS (ESI) Calcd for $C_{40}H_{40}NO_{10}$(M$^+$+H) 694.2652, found 694.2640.

Example 10

1,13-Bis[4'-((6-methyl)-4H-chromen-4-on-2-yl)phenyl]-1,4,10,13-tetraoxa-7-azamidecane (12c). The titled compound 12c was obtained from 17c (72 mg, 0.09 mmol), TFA (4 mL) and CH$_2$Cl$_2$ (4 mL) as a pale brown oil (56 mg, 90%) according to the general procedure II described above: $^1$H NMR (CDCl$_3$) δ 2.03 (br, 1H), 2.41 (s, 6h), 2.85 (t, J=4.6 Hz, 4H), 3.68 (t, J=4.2 Hz, 4H), 3.83 (t, J=4.6 Hz, 4H), 4.14 (t, J=4.6 Hz, 4H), 6.66 (s, 2H), 6.97 (d, J=8.8 Hz, 4H), 7.36 (d, J=8.4 Hz, 2H), 7.43 (dd, J=2.0, 8.0 Hz, 2H), 7.81 (d, J=8.4 Hz, 4H), 7.93 (s, 2H); LRMS (ESI) m/z 662 (M$^+$+H, 100), 684 (M$^+$+Na, 5); HRMS (ESI) Calcd for $C_{40}H_{40}NO_8$(M$^+$+H) 662.2754, found 662.2758.

Example 11

1,13-Bis[4'-((5-methoxy)-4H-chromen-4-on-2-yl)phenyl]-1,4,10,13-tetraoxa-7-azamidecane (12d). The titled compound 12d was obtained from 16d (62 mg, 0.08 mmol), TFA (4 mL) and CH$_2$Cl$_2$ (4 mL) as a pale brown oil (47 mg, 87%) according to the general procedure II described above: $^1$H NMR (CDCl$_3$) δ 2.19 (br, 1H), 2.80 (t, J=4.6 Hz, 4H), 3.62 (t, J=4.6 Hz, 4H), 3.77 (t, J=4.2 Hz, 4H), 3.91 (s, 6H), 4.08 (t, J=4.6 Hz, 4H), 6.53 (s, 2H), 6.71 (d, J=8.0 Hz, 2H), 6.91 (d, J=8.8 Hz, 4H), 6.99 (d, J=8.4 Hz, 2H), 7.45 (dd, J=8.0, 8.4 Hz, 2H), 7.70 (d, J=8.8 Hz, 4H); $^{13}$C NMR (CDCl$_3$) δ 48.9, 56.5, 67.5, 69.4, 70.2, 106.4, 107.7, 110.1, 114.5, 115.0, 123.9, 127.7, 133.6, 158.2, 159.7, 161.0, 161.3, 178.3; LRMS (ESI) m/z 694 (M$^+$+H, 100), 716 (M$^+$+Na, 20); HRMS (ESI) Calcd for $C_{40}H_{40}NO_{10}$(M$^+$+H) 694.2652, found 694.2653.

Example 12

1,13-Bis[4'-((3-benzyloxy)-4H-chromen-4-on-2-yl)phenyl]-1,4,10,13-tetraoxa-7-azamidecane (12e). The titled compound 12e was obtained from 16e (90 mg, 0.10 mmol), TFA (4 mL) and CH$_2$Cl$_2$ (4 mL) as a pale brown oil (75 mg, 93%) according to the general procedure II described above: $^1$H NMR (CDCl$_3$) δ 2.19 (br, 1H), 2.86 (t, J=4.6 Hz, 4H), 3.67 (t, J=4.2 Hz, 4H), 3.82 (t, J=4.6 Hz, 4H), 4.13 (t, J=4.6 Hz, 4H), 5.08 (s, 4H), 6.92 (d, J=9.2 Hz, 4H), 7.22-7.36 (m, 12H), 7.42 (d, J=8.4 Hz, 2H), 7.58 (dd, J=8.0, 8.4 Hz, 2H), 7.98 (d, J=8.8 Hz, 4H), 8.22 (d, J=8.0 Hz, 2H); $^{13}$C NMR (CDCl$_3$) δ 49.2, 67.4, 69.3, 70.9, 73.8, 114.3, 117.9, 123.4, 124.1, 124.5, 125.6, 128.0, 128.2, 128.8, 130.4, 133.2, 136.7, 139.2, 155.0, 156.1, 160.6, 174.8; LRMS (ESI) m/z 846 (M$^+$+H, 100), 868 (M$^+$+Na, 8); HRMS (ESI) Calcd for $C_{52}H_{48}NO_{10}$(M$^+$+H) 846.3278, found 846.3268.

Example 13

1,13-Bis[4'-((6-fluoro)-4H-chromen-4-on-2-yl)phenyl]-1,4,10,13-tetraoxa-7-azamidecane (12f). The titled compound 12f was obtained from 16f (2.30 g, 2.99 mmol), TFA (10 mL) and CH$_2$Cl$_2$ (10 mL) as a pale brown oil (1.99 g, 99%) according to the general procedure II described above: $^1$H NMR (CDCl$_3$) δ 2.48 (br, 1H), 2.91 (t, J=4.6 Hz, 4H), 3.72 (t, J=4.6 Hz, 4H), 3.87 (t, J=4.6 Hz, 4H), 4.18 (t, J=4.6 Hz, 4H), 6.68 (s, 2H), 7.00 (d, J=8.8 Hz, 4H), 7.39 (ddd, J=2.0, 8.4, 8.4 Hz, 2H), 7.50 (dd, J=4.4, 9.2 Hz, 2H), 7.79 (d, J=8.8 Hz, 4H), 7.81 (dd, J=4.4, 8.8 Hz, 2H); $^{13}$C NMR (CDCl$_3$) δ 49.3, 67.6, 69.3, 70.7, 105.4, 110.6 (d, J=23.6 Hz, C5), 115.1, 119.9 (d, J=7.8 Hz, C10), 121.7 (d, J=25.2 Hz, C7), 123.8, 125.0 (d, J=7.8 Hz, C8), 127.9, 152.2 (d, J=1.5 Hz, C9), 159.5 (d, J=245.3 Hz, C6), 161.7, 163.5, 177.4; LRMS (ESI) m/z 670 (M$^+$+H, 100), 692 (M$^+$+Na, 13); HRMS (ESI) Calcd for $C_{38}H_{34}NO_8F_2$(M$^+$+H) 670.2252, found 670.2232.

Example 14

1,13-Bis[4'-((3-benzyloxy)-4H-chromen-4-on-2-yl)phenyl]-1,4,10,13-tetraoxa-7-azamidecane (12g). The titled compound 12g was obtained from 16g (90 mg, 0.10 mmol), TFA (4 mL) and CH$_2$Cl$_2$ (4 mL) as a pale brown oil (75 mg, 93%) according to the general procedure II described above: $^1$H NMR (CDCl$_3$) δ 2.19 (br, 1H), 2.86 (t, J=4.6 Hz, 4H), 3.67 (t, J=4.2 Hz, 4H), 3.82 (t, J=4.6 Hz, 4H), 4.13 (t, J=4.6 Hz, 4H), 5.08 (s, 4H), 6.92 (d, J=9.2 Hz, 4H), 7.22-7.36 (m, 12H), 7.42 (d, J=8.4 Hz, 2H), 7.58 (dd, J=8.0, 8.4 Hz, 2H), 7.98 (d, J=8.8 Hz, 4H), 8.22 (d, J=8.0 Hz, 2H); $^{13}$C NMR (CDCl$_3$) δ 49.2, 67.4, 69.3, 70.9, 73.8, 114.3, 117.9, 123.4, 124.1, 124.5, 125.6, 128.0, 128.2, 128.8, 130.4, 133.2, 136.7, 139.2, 155.0, 156.1, 160.6, 174.8; LRMS (ESI) m/z 846 (M$^+$+H, 100), 868 (M$^+$+Na, 8); HRMS (ESI) Calcd for $C_{52}H_{48}NO_{10}$(M$^+$+H) 846.3278, found 846.3268.

Example 15

1,13-Bis[4'-(4H-chromen-4-on-2-yl)phenyl]-N-(ethyl)-1,4,10,13-tetraoxa-7-azamidecane (13). To a round-bottom flask was charged with compound 12a (80 mg, 0.13 mmol), bromoethane (25 mg, 0.23 mmol), K$_2$CO$_3$ (40 mg) and ACN (10 mL). The reaction mixture was stirred at refluxing temperature for 3 hr. When TLC indicated complete consumption of starting material, the reaction mixture was poured into a separating funnel containing water. The mixture was continuously extracted with CH$_2$Cl$_2$. The combined organic layers were dried over MgSO$_4$, filtered and evaporated to give a crude reaction mixture, which was subjected to purification by flash column chromatography on silica gel with 10-20% acetone in CH$_2$Cl$_2$ as eluent to furnish the titled compound 13 as pale brown oil (56 mg, 67%): $^1$H NMR (CDCl$_3$) δ 1.08 (t, J=7.2 Hz, 3H), 2.77 (q, J=5.2 Hz, 2H), 2.84 (t, J=5.2 Hz, 4H), 3.65 (t, J=4.8 Hz, 4H), 3.82 (t, J=4.8 Hz, 4H), 4.15 (t, J=4.8 Hz, 4H), 6.68 (s, 2H), 6.99 (d, J=8.8 Hz, 4H), 7.36 (dd, J=7.6, 7.6 Hz, 2H), 7.49 (d, J=8.4 Hz, 2H), 7.65 (dd, J=8.0, 8.4 Hz, 2H), 7.82 (d, J=8.8 Hz, 4H), 8.17 (d, J=8.0 Hz, 2H); $^{13}$C NMR (CDCl$_3$) δ 49.2, 53.3, 67.6, 69.3, 69.5, 106.1, 114.9, 117.9, 123.8, 124.1, 125.0, 125.5, 127.9, 133.5, 156.1, 161.5, 163.2, 178.3; LRMS (ESI) m/z 661 (M$^+$+H, 100); HRMS (ESI) Calcd for C$_{40}$H$_{40}$NO$_8$(M$^+$+H) 661.7396, found 661.7386.

Example 16

1,13-Bis[4'-(4H-chromen-4-on-2-yl)phenyl]-N-(2-hydroxyethyl)-1,4,10,13-tetraoxa-7-azamidecane (14). To a round-bottom flask was charged with compound 12a (70 mg, 0.11 mmol), bromoethanol (25 mg, 0.20 mmol), K$_2$CO$_3$ (35 mg) and ACN (15 mL). The reaction mixture was stirred at refluxing temperature for 3 hr. When TLC indicated complete consumption of starting material, the reaction mixture was poured into a separating funnel containing water. The mixture was continuously extracted with CH$_2$Cl$_2$. The combined organic layers were dried over MgSO$_4$, filtered and evaporated to give a crude reaction mixture, which was subjected to purification by flash column chromatography on silica gel with 10-20% acetone in CH$_2$Cl$_2$ as eluent to furnish the titled compound 14 as pale brown oil (45 mg, 56%): $^1$H NMR (CDCl$_3$) δ 2.17 (br, OH), 2.75 (t, J=5.2 Hz, 2H), 2.84 (t, J=5.2 Hz, 4H), 3.58 (t, J=5.2 Hz, 2H), 3.65 (t, J=4.8 Hz, 4H), 3.84 (t, J=4.8 Hz, 4H), 4.15 (t, J=4.8 Hz, 4H), 6.66 (s, 2H), 7.02 (d, J=8.8 Hz, 4H), 7.39 (dd, J=7.6, 7.6 Hz, 2H), 7.51 (d, J=8.4 Hz, 2H), 7.65 (dd, J=8.0, 8.4 Hz, 2H), 7.84 (d, J=8.8 Hz, 4H), 8.19 (d, J=8.0 Hz, 2H); $^{13}$C NMR (CDCl$_3$) δ 54.3, 56.7, 59.3, 67.5, 69.2, 69.8, 105.9, 114.9, 117.9, 123.7, 123.9, 125.0, 125.4, 127.8, 133.5, 156.0, 161.5, 163.1, 178.1; LRMS (ESI) m/z 677 (M$^+$+H, 100); HRMS (ESI) Calcd for C$_{40}$H$_{40}$NO$_9$(M$^+$+H) 677.7390, found 677.7382.

Example 17

1,13-Bis[4'-(4H-chromen-4-on-2-yl)phenyl]-N-(3-ethoxy-3-oxopropyl)-1,4,10,13-tetraoxa-7-azamidecane (15). To a round-bottom flask was charged with compound 12a (90 mg, 0.14 mmol), ethyl 3-bromopropionate (40 mg, 0.22 mmol), K$_2$CO$_3$ (40 mg) and ACN (15 mL). The reaction mixture was stirred at refluxing temperature for 3 hr. When TLC indicated complete consumption of starting material, the reaction mixture was poured into a separating funnel containing water. The mixture was continuously extracted with CH$_2$Cl$_2$. The combined organic layers were dried over MgSO$_4$, filtered and evaporated to give a crude reaction mixture, which was subjected to purification by flash column chromatography on silica gel with 10-20% acetone in CH$_2$Cl$_2$ as eluent to furnish the titled compound 15 as pale brown oil (65 mg, 62%): $^1$H NMR (CDCl$_3$) δ 1.23 (t, J=6.8 Hz, 3H), 2.48 (t, J=6.8 Hz, 2H), 2.79 (t, J=6.0 Hz, 4H), 2.94 (t, J=7.2 Hz, 2H), 3.64 (t, J=6.0 Hz, 4H), 3.83 (t, J=4.8 Hz, 4H), 4.08-4.17 (m, 6H), 6.71 (s, 2H), 7.01 (d, J=8.8 Hz, 4H), 7.38 (dd, J=7.6, 7.6 Hz, 2H), 7.51 (d, J=8.4 Hz, 2H), 7.65 (dd, J=8.0, 8.4 Hz, 2H), 7.84 (d, J=8.8 Hz, 4H), 8.19 (d, J=8.0 Hz, 2H); $^{13}$C NMR (CDCl$_3$) δ 14.2, 50.7, 54.0, 60.4, 67.6, 69.4, 106.2, 115.0, 117.9, 123.9, 124.2, 125.1, 125.6, 128.0, 133.6, 156.1, 161.6, 163.3, 178.3; LRMS (ESI) m/z 733 (M$^+$+H, 100); HRMS (ESI) Calcd for C$_{43}$H$_{44}$NO$_{10}$(M$^+$+H) 733.8023, found 733.8016.

Example 18

1,13-Bis[4'-(4H-chromen-4-on-2-yl)phenyl]-N-(benzyl)-1,4,10,13-tetraoxa-7-azamidecane (18). To a round-bottom flask was charged with compound 12a (1.30 g, 2.05 mmol), benzyl bromide (0.45 g, 2.63 mmol), K$_2$CO$_3$ (0.40 g) and ACN (40 mL). The reaction mixture was stirred at refluxing temperature for 3 hr. When TLC indicated complete consumption of starting material, the hot reaction mixture was filtered to remove solid K$_2$CO$_3$. The filtrate was cooled in an ice bath and numerous white precipitate was formed. The titled compound 18 was obtained after suction filtration as a white solid (1.05 g, 71%): m.p.: 112-114° C.; $^1$H NMR (CDCl$_3$) δ 2.80 (t, J=6.0 Hz, 4H), 3.64 (t, J=6.0 Hz, 4H), 3.72 (s, 2H), 3.78 (t, J=4.8 Hz, 4H), 4.11 (t, J=4.8 Hz, 4H), 6.67 (s, 2H), 6.97 (d, J=8.8 Hz, 4H), 7.25-7.36 (m, 7H), 7.48 (d, J=8.4 Hz, 2H), 7.62 (dd, J=8.0, 8.4 Hz, 2H), 7.79 (d, J=8.8 Hz, 4H), 8.17 (d, J=8.0 Hz, 2H); $^{13}$C NMR (CDCl$_3$) δ 53.9, 59.8, 67.6, 69.2, 70.2, 106.1, 115.0, 117.9, 123.8, 124.0, 125.0, 125.5, 126.9, 127.8, 128.1, 128.7, 133.5, 139.6, 156.0, 161.6, 163.2, 178.2; LRMS (ESI) m/z 724 (M$^+$+H, 100), 746 (M$^+$+Na, 14); HRMS (ESI) Calcd for C$_{45}$H$_{42}$NO$_8$(M$^+$+H) 724.2910, found 724.2917.

Example 19

1,13-Bis[4'-(4H-chromen-4-on-2-yl)phenyl]-N-(4-nitrobenzyl)-1,4,10,13-tetraoxa-7-azamidecane (19). To a round-bottom flask was charged with compound 12a (100 mg, 0.16 mmol), 4-nitrobenzyl bromide (52 mg, 0.24 mmol), K$_2$CO$_3$ (45 mg) and ACN (15 mL). The reaction mixture was stirred at refluxing temperature for 3 hr. When TLC indicated complete consumption of starting material, the reaction mixture was poured into a separating funnel containing water. The mixture was continuously extracted with CH$_2$Cl$_2$. The combined organic layers were dried over MgSO$_4$, filtered and evaporated to give a crude reaction mixture, which was subjected to purification by flash column chromatography on silica gel with 10-20% acetone in CH$_2$Cl$_2$ as eluent to furnish the titled compound 19 as pale brown solid (85 mg, 70%): m.p.: 95-97° C.; $^1$H NMR (CDCl$_3$) δ 2.82 (t, J=5.6 Hz, 4H), 3.64 (t, J=6.0 Hz, 4H), 3.78 (t, J=4.8 Hz, 4H), 3.85 (s, 2H), 4.14 (t, J=4.8 Hz, 4H), 6.70 (s, 2H), 6.99 (d, J=8.8 Hz, 4H), 7.35 (d, J=5.2 Hz, 2H), 7.49 (dd, J=8.0, 8.4 Hz, 4H), 7.65 (d, J=8.4 Hz, 2H), 7.83 (d, J=8.8 Hz, 4H), 8.11 (d, J=8.0 Hz, 2H), 8.18 (d, J=7.6 Hz, 2H); $^{13}$C NMR (CDCl$_3$) δ 54.1, 59.1, 67.6, 69.3, 70.1, 106.1, 114.9, 117.9, 123.4, 123.8, 124.2, 125.0, 125.6, 127.9, 129.0, 133.6, 146.9, 148.2, 156.1, 161.5, 163.2, 178.3; LRMS (ESI) m/z 769 (M$^+$+H, 100), 791 (M$^+$+Na, 13); HRMS (ESI) Calcd for C$_{45}$H$_{41}$N$_2$O$_{10}$(M$^+$+H) 769.2761, found 769.2762.

Example 20

1,13-Bis[4'-(4H-chromen-4-on-2-yl)phenyl]-N-(4-methoxycarbonylbenzyl)-1,4,10,13-tetraoxa-7-azamidecane (20). To a round-bottom flask was charged with compound 12a (120 mg, 0.19 mmol), methyl 4-(bromomethyl)-benzoate (60 mg, 0.26 mmol), K$_2$CO$_3$ (50 mg) and ACN (15 mL). The reaction mixture was stirred at refluxing temperature for 3 hr. When TLC indicated complete consumption of starting material, the reaction mixture was poured into a separating funnel containing water. The mixture was continuously extracted with CH$_2$Cl$_2$. The combined organic layers were dried over MgSO$_4$, filtered and evaporated to give a crude reaction mixture, which was subjected to purification by flash column chromatography on silica gel with 10-20% acetone in CH$_2$Cl$_2$ as eluent to furnish the titled compound 20 as pale brown oil (98 mg, 66%): $^1$H NMR (CDCl$_3$) δ 2.90 (t, J=5.6 Hz, 4H), 3.67 (t, J=6.0 Hz, 4H), 3.78 (t, J=4.8 Hz, 4H), 3.82 (s, 2H), 3.87 (s, 3H), 4.14 (t, J=4.8 Hz, 4H), 6.70 (s, 2H), 6.99 (d, J=8.8 Hz, 4H), 7.37 (dd, J=8.0, 8.4 Hz, 2H), 7.49 (d, J=8.4 Hz, 2H), 7.52 (d, J=8.4 Hz, 2H), 7.65 (dd, J=8.0, 8.4 Hz, 2H), 7.83

(d, J=8.8 Hz, 4H), 7.95 (d, J=8.0 Hz, 2H), 8.18 (d, J=7.6 Hz, 2H); $^{13}$C NMR (CDCl$_3$) δ 54.0, 67.6, 69.2, 106.1, 115.0, 117.9, 123.8, 124.1, 125.0, 125.6, 127.9, 128.6, 129.5, 133.5, 156.1, 161.5, 163.2, 178.3; LRMS (ESI) m/z 782 (M$^+$+H, 100), 804 (M$^+$+Na, 8); HRMS (ESI) Calcd for C$_{47}$H$_{44}$NO$_{10}$ (M$^+$+H) 782.2965, found 782.2959.

Example 21

1,13-Bis[4'-(4H-chromen-4-on-2-yl)phenyl]-N-(4-pyridylmethyl)-1,4,10,13-tetraoxa-7-azamidecane (21). To a round-bottom flask was charged with compound 12a (210 mg, 0.33 mmol), 4-(bromomethyl)-pyridine hydrobromide salt (85 mg, 0.34 mmol), K$_2$CO$_3$ (110 mg) and ACN (15 mL). The reaction mixture was stirred at refluxing temperature for 3 hr. When TLC indicated complete consumption of starting material, the reaction mixture was poured into a separating funnel containing water. The mixture was continuously extracted with CH$_2$Cl$_2$. The combined organic layers were dried over MgSO$_4$, filtered and evaporated to give a crude reaction mixture, which was subjected to purification by flash column chromatography on silica gel with 10-20% acetone in CH$_2$Cl$_2$ as eluent to furnish the titled compound 21 as pale brown oil (130 mg, 54%): $^1$H NMR (CDCl$_3$) δ 2.81 (t, J=5.6 Hz, 4H), 3.63 (t, J=6.0 Hz, 4H), 3.78 (t, J=4.8 Hz, 4H), 3.84 (s, 2H), 4.14 (t, J=4.8 Hz, 4H), 6.70 (s, 2H), 6.99 (d, J=8.8 Hz, 4H), 7.30 (d, J=5.2 Hz, 2H), 7.37 (dd, J=8.0, 8.4 Hz, 2H), 7.51 (d, J=8.4 Hz, 2H), 7.62 (dd, J=8.0, 8.4 Hz, 2H), 7.83 (d, J=8.8 Hz, 4H), 8.17 (d, J=8.0 Hz, 2H), 8.49 (d, J=5.2 Hz, 2H); $^{13}$C NMR (CDCl$_3$) δ 54.2, 58.7, 67.6, 69.3, 70.0, 106.2, 115.0, 117.9, 123.7, 123.9, 124.2, 125.1, 125.6, 127.9, 133.6, 149.6, 156.1, 161.5, 163.2, 178.3; LRMS (ESI) m/z 725 (M$^+$+H, 25); HRMS (ESI) Calcd for C$_{44}$H$_{41}$N$_2$O$_8$(M$^+$+H) 725.2863, found 725.2859.

Example 22

1,13-Bis[4'-(4H-chromen-4-on-2-yl)phenyl]-N-(2-pyridylmethyl)-1,4,10,13-tetraoxa-7-azamidecane (22). To a round-bottom flask was charged with compound 12a (110 mg, 0.17 mmol), 2-(bromomethyl)-pyridine hydrobromide salt (49 mg, 0.19 mmol), K$_2$CO$_3$ (60 mg) and ACN (10 mL). The reaction mixture was stirred at refluxing temperature for 3 hr. When TLC indicated complete consumption of starting material, the reaction mixture was poured into a separating funnel containing water. The mixture was continuously extracted with CH$_2$Cl$_2$. The combined organic layers were dried over MgSO$_4$, filtered and evaporated to give a crude reaction mixture, which was subjected to purification by flash column chromatography on silica gel with 10-20% acetone in CH$_2$Cl$_2$ as eluent to furnish the titled compound 22 as an off white solid (73 mg, 58%): m.p.: 107-109° C.; $^1$H NMR (CDCl$_3$) δ 2.87 (t, J=5.6 Hz, 4H), 3.66 (t, J=6.0 Hz, 4H), 3.78 (t, J=4.8 Hz, 4H), 3.89 (s, 2H), 4.14 (t, J=4.8 Hz, 4H), 6.68 (s, 2H), 6.98 (d, J=8.8 Hz, 4H), 7.13 (dd, J=8.0, 8.4 Hz, 1H), 7.47 (dd, J=8.0, 8.4 Hz, 2H), 7.48-7.63 (m, 6H), 7.81 (d, J=8.8 Hz, 4H), 8.17 (d, J=8.8 Hz, 2H), 8.49 (d, J=8.4 Hz, 1H); $^{13}$C NMR (CDCl$_3$) δ 54.2, 61.3, 67.6, 69.2, 70.0, 106.1, 115.0, 117.9, 121.9, 123.0, 123.8, 124.0, 125.0, 125.5, 127.9, 133.5, 136.3, 148.9, 156.1, 160.0, 161.6, 163.2, 178.3; LRMS (ESI) m/z 725 (M$^+$+H, 23), 747 (M$^+$+Na, 8); HRMS (ESI) Calcd for C$_{44}$H$_{41}$N$_2$O$_8$(M$^+$+H) 725.2863, found 725.2849.

Example 23

1,13-Bis[4'-(4H-chromen-4-on-2-yl)phenyl]-N-(4-hydroxy-1,4-dioxobutyl)-1,4,10,13-tetraoxa-7-azamidecane (23a). To a round-bottom flask was charged with compound 12a (70 mg, 0.11 mmol), succinic anhydride (22 mg, 0.22 mmol) and pyridine (10 mL). The reaction mixture was stirred at room temperature for 14 hrs. When TLC indicated complete consumption of starting material, the reaction mixture was poured into a separating funnel containing 1M hydrochloric acid solution. The mixture was continuously extracted with CH$_2$Cl$_2$. The combined organic layers were dried over MgSO$_4$, filtered and evaporated to give a crude reaction mixture, which was subjected to purification by flash column chromatography on silica gel with 20-40% acetone in CH$_2$Cl$_2$ as eluent to furnish the titled compound 23a as pale brown oil (48 mg, 59%): $^1$H NMR (CDCl$_3$) δ 2.61-2.77 (m, 4H), 3.62 (t, J=5.2 Hz, 4H), 3.69 (t, J=4.8 Hz, 4H), 3.78 (s, 4H), 4.13 (t, J=4.8 Hz, 4H), 6.70 (s, 1H), 6.72 (s, 1H), 6.99 (d, J=8.8 Hz, 4H), 7.36 (dd, J=7.6, 7.6 Hz, 2H), 7.49 (d, J=8.4 Hz, 2H), 7.65 (dd, J=8.0, 8.4 Hz, 2H), 7.81 (d, J=8.8 Hz, 4H), 8.16 (d, J=8.0 Hz, 2H); $^{13}$C NMR (CDCl$_3$) δ 28.1, 29.7, 46.7, 49.0, 67.5, 69.2, 69.3, 69.6, 105.9, 114.9, 117.9, 123.7, 124.0, 124.1, 125.1, 125.5, 127.9, 133.6, 156.1, 161.4, 161.6, 163.3, 172.8, 175.9, 178.5; LRMS (ESI) m/z 734 (M$^+$+H, 100), 756 (M$^+$+Na, 65); HRMS (ESI) Calcd for C$_{42}$H$_{40}$NO$_{11}$(M$^+$+H) 734.2601, found 734.2602.

Example 24

1,13-Bis[4'-(4H-chromen-4-on-2-yl)phenyl]-7-[(S)-2-amino-1-oxopropyl]-1,4,10,13-tetraoxa-7-azamidecane (23b). To a stirred solution of the compound 12a (190 mg, 0.30 mmol) in CH$_2$Cl$_2$ (15 mL) at 0° C. was treated successively with 1-hydroxybenzotriazole (60 mg, 0.44 mmol), Boc-Ala-OH (68 mg, 0.36 mmol) and dicyclohexylcarbodiimide (82 mg, 0.40 mmol). The mixture was allowed to warm to r.t. and stirring was continued for 14 hrs. The reaction mixture was then evaporated to give a crude reaction mixture, which was subjected to purification by flash column chromatography on silica gel with 10-20% acetone in CH$_2$Cl$_2$ as eluent to furnish the compound of 1,13-bis[4'-(4H-chromen-4-on-2-yl)phenyl]-7-[(S)-2-(tert-butyloxycarbonylamino)-1-oxopropyl]-1,4,10,13-tetraoxa-7-azamidecane as a white foam (170 mg, 70%): $^1$H NMR (CDCl$_3$) δ 1.23 (d, J=6.8 Hz, 3H), 1.35 (s, 9H), 3.45-3.75 (m, 12H), 4.06 (s, 4H), 4.67 (m, 1H), 5.39 (d, J=8.0 Hz, 1H), 6.62 (s, 1H), 6.63 (s, 1H), 6.92 (dd, J=8.0, 8.4 Hz, 4H), 7.30 (d, J=8.0 Hz, 2H), 7.44 (d, J=8.0 Hz, 2H), 7.51 (d, J=8.0 Hz, 2H), 7.75 (d, J=8.0, 8.4 Hz, 4H), 8.09 (d, J=8.0 Hz, 2H); $^{13}$C NMR (CDCl$_3$) δ 19.3, 28.3, 46.1, 46.7, 48.6, 67.4, 67.5, 69.3, 69.4, 69.5, 79.4, 105.8, 110.4, 114.9, 117.9, 118.2, 123.6, 123.8, 125.0, 125.2, 125.4, 126.7, 127.9, 128.5, 133.6, 155.0, 155.9, 161.5, 161.5, 163.3, 163.4, 173.7, 178.4; LRMS (ESI) m/z 805 (M$^+$+H, 100), 827 (M$^+$+Na, 46); HRMS (ESI) Calcd for C$_{46}$H$_{49}$N$_2$O$_{11}$(M$^+$+H) 805.3336, found 805.3340. The titled compound 23b was then obtained from the compound of 1,13-bis[4'-(4H-chromen-4-on-2-yl)phenyl]-7-[(S)-2-(tert-butyloxycarboby-lamino)-1-oxopropyl]-1,4,10,13-tetraoxa-7-azamidecane (170 mg, 0.21 mmol), TFA (5 mL) and CH$_2$Cl$_2$ (5 mL) as a pale brown oil (130 mg, 87%) according to the general procedure II described above: $^1$H NMR (CDCl$_3$) δ 1.22 (d, J=6.8 Hz, 3H), 2.01 (s, NH$_2$), 3.44-3.81 (m, 12H), 3.93 (d, J=6.8 Hz, 1H), 4.14 (t, J=4.8 Hz, 4H), 6.67 (s, 1H), 6.68 (s, 1H), 6.98 (dd, J=8.0, 8.4 Hz, 4H), 7.34 (m, 2H), 7.49 (d, J=8.0 Hz, 2H), 7.63 (m, 2H), 7.79-7.82 (m, 4H), 8.15 (d, J=8.0 Hz, 2H); $^{13}$C NMR (CDCl$_3$) δ 21.3, 46.5, 48.4, 67.5, 69.3, 69.4, 69.6, 69.7, 106.1, 114.9, 117.9, 123.8, 124.1, 124.2, 125.0, 125.5, 127.9, 133.5, 156.0, 161.3, 161.5, 163.1, 177.1, 178.2; LRMS (ESI) m/z 705 (M$^+$+H, 100), 727 (M$^+$+Na, 3); HRMS (ESI) Calcd for C$_{41}$H$_{41}$N$_2$O$_9$(M$^+$+H) 705.2812, found 705.2815.

Example 25

1,13-Bis[4'-(4H-chromen-4-on-2-yl)phenyl]-7-[2-(1,3-dioxo-1,3-dihydro-2H-isoindol-2-yl)ethyl]-1,4,10,13-tetraoxa-7-azamidecane (23c). To a round-bottom flask was charged with compound 12a (90 mg, 0.14 mmol), 1-bromo-2-(1,3-dioxo-1,3-dihydro-2H-isoindol-2-yl)ethane (65 mg, 0.26 mmol), K$_2$CO$_3$ (50 mg) and ACN (10 mL). The reaction mixture was stirred at refluxing temperature for 3 hr. When TLC indicated complete consumption of starting material, the reaction mixture was poured into a separating funnel containing water. The mixture was continuously extracted with CH$_2$Cl$_2$. The combined organic layers were dried over MgSO$_4$, filtered and evaporated to give a crude reaction mixture, which was subjected to purification by flash column chromatography on silica gel with 10-20% acetone in CH$_2$Cl$_2$ as eluent to furnish the titled compound 23c as pale brown oil (72 mg, 63%): $^1$H NMR (CDCl$_3$) δ 2.88 (s, 6H), 3.63 (t, J=5.2 Hz, 4H), 3.78 (t, J=4.8 Hz, 6H), 4.11 (t, J=4.4 Hz, 4H), 6.68 (s, 2H), 6.99 (d, J=8.8 Hz, 4H), 7.37 (dd, J=8.0, 8.4 Hz, 2H), 7.51 (d, J=8.4 Hz, 2H), 7.63-7.67 (m, 4H), 7.77-7.81 (m, 6H), 8.19 (dd, J=1.2, 8.4 Hz, 2H); $^{13}$C NMR (CDCl$_3$) δ 52.5, 54.2, 67.6, 69.3, 70.1, 106.1, 115.0, 117.9, 123.1, 123.9, 124.0, 125.0, 125.6, 127.9, 132.1, 133.5, 133.8, 156.1, 161.6, 163.2, 168.3, 178.3; LRMS (ESI) m/z 807 (M$^+$+H, 20), 829 (M$^+$+Na, 4); HRMS (ESI) Calcd for C$_{48}$H$_{43}$N$_2$O$_{10}$(M$^+$+H) 807.2918, found 807.2920.

Example 26

1,13-Bis[4'-(4H-chromen-4-on-2-yl)phenyl]-7-(benzoyl)-1,4,10,13-tetraoxa-7-azamidecane (23d). To a round-bottom flask was charged with compound 12a (90 mg, 0.14 mmol), benzoyl chloride (42 mg, 0.30 mmol) and pyridine (10 mL). The reaction mixture was stirred at room temperature for 2 hrs. When TLC indicated complete consumption of starting material, the reaction mixture was poured into a separating funnel containing 1M hydrochloric acid solution. The mixture was continuously extracted with CH$_2$Cl$_2$. The combined organic layers were dried over MgSO$_4$, filtered and evaporated to give a crude reaction mixture, which was subjected to purification by flash column chromatography on silica gel with 10-20% acetone in CH$_2$Cl$_2$ as eluent to furnish the titled compound 23d as pale brown oil (76 mg, 73%): $^1$H NMR (CDCl$_3$) δ 3.61 (s, 4H), 3.73 (s, 4H), 3.88 (s, 4H), 4.18 (s, 4H), 6.74 (s, 2H), 7.01 (d, J=8.8 Hz, 4H), 7.31-7.41 (m, 7H), 7.52 (d, J=8.4 Hz, 2H), 7.66 (dd, J=8.0, 8.4 Hz, 2H), 7.84 (d, J=8.8 Hz, 4H), 8.19 (d, J=8.4 Hz, 2H); $^{13}$C NMR (CDCl$_3$) δ 67.6, 69.4, 69.5, 106.1, 115.0, 118.0, 123.8, 124.1, 125.1, 125.6, 126.8, 128.0, 128.3, 129.3, 133.6, 136.7, 156.1, 161.6, 163.3, 172.4, 178.2; LRMS (ESI) m/z 738 (M$^+$+H, 100), 760 (M$^+$+Na, 91); HRMS (ESI) Calcd for C$_{45}$H$_{40}$NO$_9$(M$^+$+H) 738.2703, found 738.2681.

Example 27

1,13-Bis[4'-(4H-chromen-4-on-2-yl)phenyl]-N-(methanesulfonyl)-1,4,10,13-tetraoxa-7-azamidecane (24). To a round-bottom flask was charged with compound 12a (80 mg, 0.13 mmol), methanesulfonyl chloride (30 mg, 0.26 mmol) and pyridine (10 mL). The reaction mixture was stirred at room temperature for 14 hr. When TLC indicated complete consumption of starting material, the reaction mixture was poured into a separating funnel containing 1M hydrochloric acid solution. The mixture was continuously extracted with CH$_2$Cl$_2$. The combined organic layers were dried over MgSO$_4$, filtered and evaporated to give a crude reaction mixture, which was subjected to purification by flash column chromatography on silica gel with 10-20% acetone in CH$_2$Cl$_2$ as eluent to furnish the titled compound 24 as pale brown oil (56 mg, 60%): $^1$H NMR (CDCl$_3$) δ 2.93 (s, 3H), 3.53 (t, J=5.2 Hz, 4H), 3.72 (t, J=4.8 Hz, 4H), 3.81 (t, J=4.8 Hz, 4H), 4.13 (t, J=4.8 Hz, 4H), 6.68 (s, 2H), 6.97 (d, J=8.8 Hz, 4H), 7.35 (dd, J=7.6, 7.6 Hz, 2H), 7.49 (d, J=8.4 Hz, 2H), 7.63 (dd, J=8.0, 8.4 Hz, 2H), 7.82 (d, J=8.8 Hz, 4H), 8.19 (d, J=8.0 Hz, 2H); $^{13}$C NMR (CDCl$_3$) δ 38.8, 47.5, 67.4, 69.3, 70.0, 106.1, 114.8, 117.9, 123.8, 124.2, 125.1, 125.5, 128.0, 133.6, 156.1, 161.4, 163.1, 178.2; LRMS (ESI) m/z 712 (M$^+$+H, 62), 734 (M$^+$+Na, 90); HRMS (ESI) Calcd for C$_{39}$H$_{38}$NO$_{10}$S(M$^+$+H) 712.2216, found 712.2224.

Example 28

1,13-Bis[4'-(4H-chromen-4-on-2-yl)phenyl]-N-(4-methylbenzenesulfonyl)-1,4,10,13-tetraoxa-7-azamidecane (25a). To a round-bottom flask was charged with compound 12a (80 mg, 0.13 mmol), p-toluenesulfonyl chloride (40 mg, 0.21 mmol) and pyridine (10 mL). The reaction mixture was stirred at room temperature for 14 hr. When TLC indicated complete consumption of starting material, the reaction mixture was poured into a separating funnel containing 1M hydrochloric acid solution. The mixture was continuously extracted with CH$_2$Cl$_2$. The combined organic layers were dried over MgSO$_4$, filtered and evaporated to give a crude reaction mixture, which was subjected to purification by flash column chromatography on silica gel with 10-20% acetone in CH$_2$Cl$_2$ as eluent to furnish the titled compound 25a as pale brown oil (61 mg, 66%): $^1$H NMR (CDCl$_3$) δ 2.38 (s, 3H), 3.42 (t, J=5.2 Hz, 4H), 3.72 (t, J=4.8 Hz, 4H), 3.77 (t, J=4.8 Hz, 4H), 4.08 (t, J=4.8 Hz, 4H), 6.68 (s, 2H), 6.98 (d, J=8.8 Hz, 4H), 7.25 (d, J=7.6 Hz, 2H), 7.35 (dd, J=7.6, 7.6 Hz, 2H), 7.49 (d, J=8.4 Hz, 2H), 7.63 (dd, J=8.0, 8.4 Hz, 2H), 7.71 (d, J=7.6 Hz, 2H), 7.82 (d, J=8.8 Hz, 4H), 8.17 (d, J=8.0 Hz, 2H); $^{13}$C NMR (CDCl$_3$) δ 21.5, 49.0, 67.5, 69.3, 70.5, 106.1, 114.9, 117.9, 123.8, 124.1, 125.0, 125.5, 127.1, 129.6, 133.6, 136.6, 143.3, 156.0, 161.5, 163.1, 178.3; LRMS (ESI) m/z 788 (M$^+$+H, 55), 810 (M$^+$+Na, 67); HRMS (ESI) Calcd for C$_{45}$H$_{42}$NO$_{10}$S(M$^+$+H) 788.2529, found 788.2540.

Example 29

1,13-Bis[4'-(4H-chromen-4-on-2-yl)phenyl]-7-(dansyl)-1,4,10,13-tetraoxa-7-azamidecane (25b). To a round-bottom flask was charged with compound 12a (120 mg, 0.19 mmol), dansyl chloride (80 mg, 0.30 mmol) and pyridine (10 mL). The reaction mixture was stirred at room temperature for 14 hrs. When TLC indicated complete consumption of starting material, the reaction mixture was poured into a separating funnel containing 1M hydrochloric acid solution. The mixture was continuously extracted with CH$_2$Cl$_2$. The combined organic layers were dried over MgSO$_4$, filtered and evaporated to give a crude reaction mixture, which was subjected to purification by flash column chromatography on silica gel with 10-20% acetone in CH$_2$Cl$_2$ as eluent to furnish the titled compound 25b as pale yellow solid (120 mg, 73%): m.p.: 72-74° C.; $^1$H NMR (CDCl$_3$) δ 2.81 (s, 6H), 3.64-3.67 (m, 12H), 3.98 (t, J=4.8 Hz, 4H), 6.63 (s, 2H), 6.90 (d, J=8.8 Hz, 4H), 7.12 (d, J=7.6 Hz, 1H), 7.32 (dd, J=7.6, 8.0 Hz, 2H), 7.41-7.50 (m, 4H), 7.56 (dd, J=7.6, 8.0 Hz, 2H), 7.74 (d, J=8.8 Hz, 4H), 8.10 (d, J=8.0 Hz, 2H), 8.12 (d, J=8.0 Hz, 1H), 8.15 (d, J=8.0 Hz, 1H), 8.28 (d, J=8.0 Hz, 1H); $^{13}$C NMR (CDCl$_3$)

δ 45.3, 48.1, 67.4, 69.2, 70.2, 106.0, 114.9, 115.1, 117.9, 119.5, 123.1, 123.7, 123.9, 125.0, 125.4, 127.8, 128.0, 128.6, 130.0, 130.0, 130.2, 133.5, 135.6, 151.7, 156.0, 161.4, 163.1, 178.2; LRMS (ESI) m/z 867 (M$^+$+H, 85), 889 (M$^+$+Na, 18); HRMS (ESI) Calcd for $C_{50}H_{47}N_2O_{10}S$(M$^+$+H) 867.2951, found 867.2927.

Example 30

1,13-Bis[4'-(4H-chromen-4-on-2-yl)phenyl]-N-(3-phenylpropyl)-1,4,10,13-tetraoxa-7-azamidecane (26). To a round-bottom flask was charged with compound 12a (110 mg, 0.17 mmol), 3-bromo-1-phenylpropane (60 mg, 0.30 mmol), $K_2CO_3$ (50 mg) and ACN (15 mL). The reaction mixture was stirred at refluxing temperature for 3 hr. When TLC indicated complete consumption of starting material, the reaction mixture was poured into a separating funnel containing water. The mixture was continuously extracted with $CH_2Cl_2$. The combined organic layers were dried over $MgSO_4$, filtered and evaporated to give a crude reaction mixture, which was subjected to purification by flash column chromatography on silica gel with 10-20% acetone in $CH_2Cl_2$ as eluent to furnish the titled compound 26 as pale brown oil (86 mg, 66%): $^1$H NMR (CDCl$_3$) δ 1.81 (m, 2H), 2.58-2.62 (m, 4H), 2.79 (t, J=5.2 Hz, 4H), 3.63 (t, J=4.8 Hz, 4H), 3.81 (t, J=4.8 Hz, 4H), 4.14 (t, J=4.8 Hz, 4H), 6.70 (s, 2H), 7.00 (d, J=8.8 Hz, 4H), 7.15-7.26 (m, 5H), 7.37 (dd, J=7.6, 7.6 Hz, 2H), 7.51 (d, J=8.4 Hz, 2H), 7.65 (dd, J=8.0, 8.4 Hz, 2H), 7.83 (d, J=8.8 Hz, 4H), 8.19 (d, J=8.0 Hz, 2H); $^{13}$C NMR (CDCl$_3$) δ28.8, 33.4, 33.5, 54.1, 54.9, 67.7, 69.3, 70.1, 106.1, 115.0, 117.9, 123.9, 124.1, 125.1, 125.6, 125.8, 127.9, 128.3, 128.4, 133.6, 142.2, 156.1, 161.6, 163.3, 178.3; LRMS (ESI) m/z 752 (M$^+$+H, 55); HRMS (ESI) Calcd for $C_{47}H_{46}NO_8$(M$^+$+H) 751.8621, found 751.8612.

Example 31

1,13-Bis[4'-(4H-chromen-4-on-2-yl)phenyl]-7-(tert-butylacetyl)-1,4,10,13-tetraoxa-7-azamidecane (33). To a round-bottom flask was charged with compound 12a (100 mg, 0.16 mmol), tert-butylacetyl chloride (40 mg, 0.30 mmol) and pyridine (10 mL). The reaction mixture was stirred at room temperature for 2 hrs. When TLC indicated complete consumption of starting material, the reaction mixture was poured into a separating funnel containing 1M hydrochloric acid solution. The mixture was continuously extracted with $CH_2Cl_2$. The combined organic layers were dried over $MgSO_4$, filtered and evaporated to give a crude reaction mixture, which was subjected to purification by flash column chromatography on silica gel with 10-20% acetone in $CH_2Cl_2$ as eluent to furnish the titled compound 33 as pale brown oil (81 mg, 70%): $^1$H NMR (CDCl$_3$) δ 1.01 (s, 9H), 3.59 (s, 2H), 3.59-3.71 (m, 8H), 3.79 (t, J=4.8 Hz, 4H), 4.14 (t, J=4.8 Hz, 4H), 6.71 (s, 1H), 6.72 (s, 1H), 6.98 (dd, J=8.0, 8.4 Hz, 4H), 7.34 (dd, J=7.2, 8.0 Hz, 2H), 7.51 (dd, J=8.0, 8.4 Hz, 2H), 7.63 (dd, J=7.2, 8.0 Hz, 2H), 7.82 (d, J=8.6 Hz, 4H), 8.17 (dd, J=8.0, 8.4 Hz, 2H); $^{13}$C NMR (CDCl$_3$) δ 29.9, 31.4, 44.6, 46.4, 49.5, 67.6, 69.3, 69.6, 69.8, 69.9, 106.1, 106.1, 114.9, 117.9, 117.9, 123.8, 124.1, 124.1, 125.1, 125.6, 127.9, 133.6, 156.1, 161.5, 161.6, 163.2, 163.3, 172.4, 178.2; LRMS (ESI) m/z 732 (M$^+$+H, 100), 754 (M$^+$+Na, 90); HRMS (ESI) Calcd for $C_{44}H_{46}NO_9$(M$^+$+H) 732.3173, found 732.3147.

Example 32

1,13-Bis[4'-(4H-chromen-4-on-2-yl)phenyl]-7-(4-fluorobenzyl)-1,4,10,13-tetraoxa-7-azamidecane (34). To a round-bottom flask was charged with compound 12a (0.31 g, 0.49 mmol), 4-fluorobenzyl methanesulfonate (0.12 g, 0.59 mmol), $K_2CO_3$ (90 mg) and ACN (20 mL). The reaction mixture was stirred at refluxing temperature for 3 hr. When TLC indicated complete consumption of starting material, the hot reaction mixture was filtered to remove solid $K_2CO_3$. The filtrate was cooled in an ice bath and numerous white precipitate was formed. The titled compound 34 was obtained after suction filtration as a white solid (0.25 g, 69%): m.p.: 119-122° C.; $^1$H NMR (CDCl$_3$) δ 2.83 (s, 4H), 3.67 (t, J=4.6 Hz, 4H), 3.79 (t, J=4.6 Hz, 4H), 3.81 (s, 2H), 4.14 (t, J=4.6 Hz, 4H), 6.69 (s, 2H), 6.98 (d, J=8.6 Hz, 4H), 7.36 (dd, J=7.2, 8.0 Hz, 2H), 7.47-7.54 (m, 6H), 7.64 (dd, J=7.2, 8.0 Hz, 2H), 7.82 (d, J=8.6 Hz, 4H), 8.16 (d, J=8.0 Hz, 2H); $^{13}$C NMR (CDCl$_3$) δ 54.0, 59.3, 67.7, 69.3, 70.2, 106.1, 115.0, 117.9, 123.9, 124.1, 125.0, 125.1, 125.6, 127.9, 128.8, 133.5, 144.3, 156.1, 161.6, 163.2, 178.2; LRMS (ESI) m/z 742 (M$^+$+H, 100); HRMS (ESI) Calcd for $C_{45}H_{41}NO_8F$(M$^+$+H) 742.2816, found 742.2787.

Example 33

1,13-Bis[4'-(4H-chromen-4-on-2-yl)phenyl]-7-(4-trifluoromethylbenzyl)-1,4,10,13-tetraoxa-7-azamidecane (35). To a round-bottom flask was charged with compound 12a (210 mg, 0.33 mmol), 4-trifluoromethylbenzyl chloride (90 mg, 0.46 mmol), $K_2CO_3$ (70 mg) and ACN (15 mL). The reaction mixture was stirred at refluxing temperature for 3 hr. When TLC indicated complete consumption of starting material, the reaction mixture was poured into a separating funnel containing water. The mixture was continuously extracted with $CH_2Cl_2$. The combined organic layers were dried over $MgSO_4$, filtered and evaporated to give a crude reaction mixture, which was subjected to purification by flash column chromatography on silica gel with 10-20% acetone in $CH_2Cl_2$ as eluent to furnish the titled compound 35 as pale brown oil (190 mg, 72%): $^1$H NMR (CDCl$_3$) δ 2.83 (s, 4H), 3.68 (s, 4H), 3.79 (s, 4H), 3.83 (s, 2H), 4.17 (s, 4H), 6.73 (s, 2H), 6.96-7.03 (m, 6H), 7.34-7.42 (m, 4H), 7.55 (d, J=8.0 Hz, 2H), 7.68 (dd, J=8.0, 8.4 Hz, 2H), 7.87 (d, J=8.4 Hz, 4H), 8.22 (d, J=8.0 Hz, 2H); $^{13}$C NMR (CDCl$_3$) δ 67.7, 69.3, 106.2, 115.0, 117.9, 123.9, 124.2, 125.1, 125.7, 128.0, 133.6, 156.2, 161.6, 163.3, 178.3; LRMS (ESI) m/z 792 (M$^+$+H, 100); HRMS (ESI) Calcd for $C_{46}H_{41}NO_8F_3$(M$^+$+H) 792.2784, found 792.2764.

Example 34

1,13-Bis[4'-(4H-chromen-4-on-2-yl)phenyl]-7-(3,4-difluorobenzyl)-1,4,10,13-tetraoxa-7-azamidecane (38). To a round-bottom flask was charged with compound 12a (210 mg, 0.33 mmol), 3,4-difluorobenzyl bromide (90 mg, 0.43 mmol), $K_2CO_3$ (70 mg) and ACN (20 mL). The reaction mixture was stirred at refluxing temperature for 3 hr. When TLC indicated complete consumption of starting material, the hot reaction mixture was filtered to remove solid $K_2CO_3$. The filtrate was cooled in an ice bath and numerous white precipitate was formed. The titled compound 38 was obtained after suction filtration as a white solid (160 mg, 64%): m.p.: 96-98° C.; $^1$H NMR (CDCl$_3$) δ 2.83 (s, 4H), 3.67 (s, 4H), 3.72 (s, 2H), 3.82 (t, J=4.6 Hz, 4H), 4.16 (t, J=4.6 Hz, 4H), 6.72 (s, 2H), 6.98-7.06 (m, 6H), 7.28 (m, 1H), 7.39 (dd, J=8.0, 8.4 Hz, 2H), 7.53 (d, J=8.4 Hz, 2H), 7.67 (dd, J=8.0, 8.4 Hz, 2H), 7.85 (d, J=8.8 Hz, 4H), 8.21 (d, J=8.4 Hz, 2H); $^{13}$C NMR (CDCl$_3$) δ 53.8, 58.7, 67.7, 69.3, 70.2, 106.2, 115.0, 116.6, 116.8, 117.9, 123.9, 124.2, 125.1, 125.6, 127.9, 133.6, 156.1, 161.6, 163.2, 178.3; LRMS (ESI) m/z 760 (M$^+$+H, 100); HRMS (ESI) Calcd for C$_{45}$H$_{40}$NO$_8$F$_2$(M$^+$+H) 760.2722, found 760.2757.

Example 45

1,13-Bis[4'-(4H-chromen-4-on-2-yl)phenyl]-7-(3,4,5-trifluorobenzyl)-1,4,10,13-tetraoxa-7-azamidecane (39). To a round-bottom flask was charged with compound 12a (210 mg, 0.33 mmol), 3,4,5-trifluorobenzyl bromide (100 mg, 0.42 mmol), K$_2$CO$_3$ (75 mg) and ACN (20 mL). The reaction mixture was stirred at refluxing temperature for 3 hr. When TLC indicated complete consumption of starting material, the hot reaction mixture was filtered to remove solid K$_2$CO$_3$. The filtrate was cooled in an ice bath and numerous white precipitate was formed. The titled compound 39 was obtained after suction filtration as a white solid (145 mg, 56%): m.p.: 78-80° C.; $^1$H NMR (CDCl$_3$) δ 2.83 (s, 4H), 3.68 (s, 4H), 3.73 (s, 2H), 3.83 (s, 4H), 4.17 (s, 4H), 6.72 (s, 2H), 7.01 (d, J=8.4 Hz, 4H), 7.04 (s, 2H), 7.39 (dd, J=8.0, 8.4 Hz, 2H), 7.53 (d, J=8.0 Hz, 2H), 7.67 (dd, J=8.0, 8.4 Hz, 2H), 7.85 (d, J=8.4 Hz, 4H), 8.21 (d, J=8.4 Hz, 2H); $^{13}$C NMR (CDCl$_3$) δ 53.9, 58.6, 67.6, 69.4, 70.2, 106.2, 115.0, 117.9, 123.9, 124.2, 125.1, 125.6, 127.9, 133.6, 156.1, 161.6, 163.2, 178.3; LRMS (ESI) m/z 778 (M$^+$+H, 100); HRMS (ESI) Calcd for C$_{45}$H$_{39}$NO$_8$F$_3$ (M$^+$+H) 778.2628, found 778.2657.

Example 36

1,13-Bis[4'-(4H-chromen-4-on-2-yl)phenyl]-7-(3-fluorobenzyl)-1,4,10,13-tetraoxa-7-azamidecane (37). To a round-bottom flask was charged with compound 12a (190 mg, 0.30 mmol), 3-fluorobenzyl bromide (90 mg, 0.48 mmol), K$_2$CO$_3$ (70 mg) and ACN (20 mL). The reaction mixture was stirred at refluxing temperature for 3 hr. When TLC indicated complete consumption of starting material, the hot reaction mixture was filtered to remove solid K$_2$CO$_3$. The filtrate was cooled in an ice bath and numerous white precipitate was formed. The titled compound 37 was obtained after suction filtration as a white solid (160 mg, 72%): m.p.: 91-93° C.; $^1$H NMR (CDCl$_3$) δ 2.85 (s, 4H), 3.69 (s, 4H), 3.78 (s, 2H), 3.83 (t, J=4.6 Hz, 4H), 4.17 (t, J=4.6 Hz, 4H), 6.72 (s, 2H), 6.94 (dd, J=8.0, 8.4 Hz, 1H), 7.02 (J=8.8 Hz, 4H), 7.13-7.24 (m, 3H), 7.39 (dd, J=8.0, 8.4 Hz, 2H), 7.53 (d, J=8.0 Hz, 2H), 7.67 (dd, J=8.0, 8.4 Hz, 2H), 7.85 (d, J=8A Hz, 4H), 8.21 (d, J=8.4 Hz, 2H); $^{13}$C NMR (CDCl$_3$) δ 54.0, 59.3, 67.6, 69.3, 70.2, 106.2, 115.0, 117.9, 123.9, 124.2, 125.1, 125.6, 127.9, 129.6, 133.6, 156.1, 161.6, 161.8, 163.3, 164.2, 178.3; LRMS (ESI) m/z 742 (M$^+$+H, 100), 764 (M$^+$+Na, 5); HRMS (ESI) Calcd for C$_{45}$H$_{41}$NO$_8$F(M$^+$+H) 742.2816, found 742.2828.

Example 37

1,13-Bis[4'-(4H-chromen-4-on-2-yl)phenyl]-7-(2-fluorobenzyl)-1,4,10,13-tetraoxa-7-azamidecane (36). To a round-bottom flask was charged with compound 12a (190 mg, 0.30 mmol), 2-fluorobenzyl bromide (90 mg, 0.48 mmol), K$_2$CO$_3$ (70 mg) and ACN (20 mL). The reaction mixture was stirred at refluxing temperature for 3 hr. When TLC indicated complete consumption of starting material, the hot reaction mixture was filtered to remove solid K$_2$CO$_3$. The filtrate was cooled in an ice bath and numerous white precipitate was formed. The titled compound 36 was obtained after suction filtration as a white solid (153 mg, 69%): m.p.: 82-84° C.; $^1$H NMR (CDCl$_3$) δ 2.87 (s, 4H), 3.71 (s, 4H), 3.82 (s, 4H), 3.84 (s, 2H), 4.15 (t, J=4.6 Hz, 4H), 6.72 (s, 2H), 7.01-7.23 (m, 7H), 7.39 (dd, J=8.0, 8.4 Hz, 2H), 7.49 (m, 1H), 7.53 (d, J=8.0 Hz, 2H), 7.67 (dd, J=8.0, 8.4 Hz, 2H), 7.82 (d, J=8.4 Hz, 4H), 8.18 (d, J=8.4 Hz, 2H); $^{13}$C NMR (CDCl$_3$) δ 52.1, 53.9, 67.7, 69.3, 70.0, 106.1, 115.0, 115.3, 117.9, 123.9, 124.1, 125.1, 125.6, 127.9, 131.4, 133.6, 156.1, 160.1, 161.6, 162.5, 163.3, 178.3; LRMS (ESI) m/z 742 (M$^+$+H, 100), 764 (M$^+$+Na, 4); HRMS (ESI) Calcd for C$_{45}$H$_{41}$NO$_8$F(M$^+$+H) 742.2816, found 742.2852.

Example 38

1,13-Bis[4'-(4H-chromen-4-on-2-yl)phenyl]-7-(2,4-difluorobenzyl)-1,4,10,13-tetraoxa-7-azamidecane (40). To a round-bottom flask was charged with compound 12a (240 mg, 0.38 mmol), 2,4-difluorobenzyl bromide (90 mg, 0.43 mmol), K$_2$CO$_3$ (70 mg) and ACN (10 mL). The reaction mixture was stirred at refluxing temperature for 3 hr. When TLC indicated complete consumption of starting material, the reaction mixture was poured into a separating funnel containing water. The mixture was continuously extracted with CH$_2$Cl$_2$. The combined organic layers were dried over MgSO$_4$, filtered and evaporated to give a crude reaction mixture, which was subjected to purification by flash column chromatography on silica gel with 10-20% acetone in CH$_2$Cl$_2$ as eluent to furnish the titled compound 40 as pale brown oil (200 mg, 70%): $^1$H NMR (CDCl$_3$) δ 2.90 (br, 4H), 3.66-3.93 (m, 10H), 4.17 (t, J=4.60 Hz, 4H), 6.72 (s, 2H), 6.70-6.89 (m, 2 H), 7.01 (d, J=8.89 Hz, 4 H), 7.40 (t, J=7.61 Hz, 2 H), 7.53 (d, J=8.20 Hz, 2 H), 7.60-7.73 (m, 2 H), 7.85 (d, J=8.98 Hz, 4 H), 8.21 (dd, J=8.00, 1.37 Hz, 2 H); $^{13}$C NMR (CDCl$_3$) δ 51.7, 53.7, 67.6, 69.4, 70.2, 103.6, 106.2, 115.0, 117.9, 123.9, 124.2, 125.1, 125.6, 127.9, 133.6, 156.2, 161.6, 163.2, 178.3; LRMS (ESI) m/z 760 (M$^+$+H, 100), 782 (M$^+$+Na, 15); HRMS (ESI) Calcd for C$_{45}$H$_{40}$NO$_8$F$_2$(M$^+$+H) 760.2722, found 760.2736.

Example 39

1,13-Bis[4'-(4H-chromen-4-on-2-yl)phenyl]-7-(2,6-difluorobenzyl)-1,4,10,13-tetraoxa-7-azamidecane (41). To a round-bottom flask was charged with compound 12a (240 mg, 0.38 mmol), 2,6-difluorobenzyl bromide (90 mg, 0.43 mmol), K$_2$CO$_3$ (70 mg) and ACN (10 mL). The reaction mixture was stirred at refluxing temperature for 3 hr. When TLC indicated complete consumption of starting material, the reaction mixture was poured into a separating funnel containing water. The mixture was continuously extracted with CH$_2$Cl$_2$. The combined organic layers were dried over MgSO$_4$, filtered and evaporated to give a crude reaction mixture, which was subjected to purification by flash column chromatography on silica gel with 10-20% acetone in CH$_2$Cl$_2$ as eluent to furnish the titled compound 41 as pale brown oil (122 mg, 42%): $^1$H NMR (CDCl$_3$) δ 2.91 (br, 4 H), 3.77 (br, 4 H), 3.80-3.89 (m, 4 H), 3.93 (br, 2 H), 4.16 (t, J=4.68 Hz, 4 H), 6.71 (s, 2 H), 6.89 (t, J=7.81 Hz, 2 H), 7.01 (d, J=8.59 Hz, 4 H), 7.21-7.30 (m, 2 H), 7.38 (t, J=7.41 Hz, 2 H), 7.51 (d, J=8.20 Hz, 2 H), 7.63-7.71 (m, 2 H), 7.83 (d, J=8.98 Hz, 4 H), 8.19 (dd, J=8.00, 1.37 Hz, 2 H); $^{13}$C NMR (CDCl$_3$) δ 45.9, 53.6, 67.6, 69.3, 70.0, 106.1, 111.2, 111.5, 115.1, 117.9, 123.9, 124.1, 125.1, 125.6, 127.9, 133.6 156.1, 160.8, 160.9, 161.6, 163.3, 163.4, 178.3; LRMS (ESI) m/z 760 (M$^+$+H, 100), 782 (M$^+$+Na, 10); HRMS (ESI) Calcd for C$_{45}$H$_{40}$NO$_8$F$_2$(M$^+$+H) 760.2722, found 760.2742.

Example 40

1,13-Bis[4'-(4H-chromen-4-on-2-yl)phenyl]-7-(4-methoxybenzyl)-1,4,10,13-tetraoxa-7-azamidecane (42a). To a round-bottom flask was charged with compound 12a (380 mg, 0.60 mmol), 4-methoxybenzyl chloride (120 mg, 0.76 mmol), $K_2CO_3$ (120 mg) and ACN (20 mL). The reaction mixture was stirred at refluxing temperature for 3 hr. When TLC indicated complete consumption of starting material, the reaction mixture was poured into a separating funnel containing water. The mixture was continuously extracted with $CH_2Cl_2$. The combined organic layers were dried over $MgSO_4$, filtered and evaporated to give a crude reaction mixture, which was subjected to purification by flash column chromatography on silica gel with 10-20% acetone in $CH_2Cl_2$ as eluent to furnish the titled compound 42a as a white foam (290 mg, 64%): $^1$H NMR (CDCl$_3$) δ 2.82 (t, J=5.66 Hz, 4 H), 3.64-3.73 (m, 6 H), 3.75-3.85 (m, 7 H), 4.13-4.18 (m, 4 H), 6.72 (s, 2 H), 6.82-6.89 (m, 2 H), 6.99-7.04 (m, 4 H), 7.24-7.32 (m, 2 H), 7.36-7.41 (m, 2 H), 7.52 (d, J=8.59 Hz, 2 H), 7.67 (ddd, J=8.49, 7.12, 1.56 Hz, 2 H), 7.81-7.86 (m, 4 H), 8.20 (dd, J=7.80, 1.56 Hz, 2 H); $^{13}$C NMR (CDCl$_3$) δ 53.7, 55.3, 59.2, 67.7, 69.3, 70.2, 106.2, 113.6, 114.1, 115.0, 118.0, 123.9, 124.1, 125.1, 125.6, 127.9, 130.0, 133.6, 156.1, 158.7, 161.7, 163.3, 178.3; LRMS (ESI) m/z 754 (M$^+$+H, 100), 776 (M$^+$+Na, 50); HRMS (ESI) Calcd for $C_{46}H_{44}NO_9$(M$^+$+H) 754.3016, found 754.2983.

Example 41

1,13-Bis[4'-(4H-chromen-4-on-2-yl)phenyl]-7-(4-trifluoromethoxybenzyl)-1,4,10,13-tetraoxa-7-azamidecane (42b). To a round-bottom flask was charged with compound 12a (210 mg, 0.33 mmol), 4-trifluoromethoxybenzyl bromide (100 mg, 0.39 mmol), $K_2CO_3$ (70 mg) and ACN (10 mL). The reaction mixture was stirred at refluxing temperature for 3 hr. When TLC indicated complete consumption of starting material, the reaction mixture was poured into a separating funnel containing water. The mixture was continuously extracted with $CH_2Cl_2$. The combined organic layers were dried over $MgSO_4$, filtered and evaporated to give a crude reaction mixture, which was subjected to purification by flash column chromatography on silica gel with 10-20% acetone in $CH_2Cl_2$ as eluent to furnish the titled compound 42b as pale brown oil (183 mg, 68%): $^1$H NMR (CDCl$_3$) δ 2.87 (br, 4 H), 3.72 (br, 6 H), 3.83 (br, 4 H), 4.00-4.26 (m, 4 H), 6.73 (s, 2 H), 6.99-7.05 (m, 4 H), 7.15 (d, J=8.20 Hz, 2 H), 7.41 (t, J=7.41 Hz, 4 H), 7.54 (d, J=8.20 Hz, 2 H), 7.68 (ddd, J=8.39, 7.02, 1.76 Hz, 2 H), 7.83-7.89 (m, 4 H), 8.21 (dd, J=8.00, 1.37 Hz, 2 H); $^{13}$C NMR (CDCl$_3$) δ 58.9, 62.9, 67.6, 69.4, 70.1, 106.2, 115.0, 117.93, 120.8, 123.9, 124.3, 125.1, 125.7, 128.0, 133.6, 156.2, 161.6, 163.2, 178.3; LRMS (ESI) m/z 808 (M$^+$+H, 100), 830 (M$^+$+Na, 12); HRMS (ESI) Calcd for $C_{46}H_{41}NO_9F_3$(M$^+$+H) 808.2733, found 808.2751.

Example 42

1,13-Bis[4'-(4H-chromen-4-on-2-yl)phenyl]-7-(4-acetyloxybenzyl)-1,4,10,13-tetraoxa-7-azamidecane (42c). To a round-bottom flask was charged with compound 12a (1.20 g, 1.86 mmol), 4-(chloromethyl)phenyl acetate (0.40 g, 2.16 mmol), $K_2CO_3$ (0.50 g) and acetone (40 mL). The reaction mixture was stirred at refluxing temperature for 3 hr. When TLC indicated complete consumption of starting material, the reaction mixture was cooled, filtered and evaporated to give a crude reaction mixture, which was subjected to purification by flash column chromatography on silica gel with 10-20% acetone in $CH_2Cl_2$ as eluent to furnish the titled compound 42c as a white foam (0.60 g, 41%): $^1$H NMR (CDCl$_3$) δ 2.23 (s, 3 H), 2.78 (t, J=5.87 Hz, 4 H), 3.61 (t, J=5.87 Hz, 4 H), 3.69 (s, 2 H), 3.72-3.76 (m, 4 H), 4.05-4.09 (m, 4 H), 6.63 (s, 2 H), 6.90-6.94 (m, 4 H), 6.95-6.98 (m, 2 H) 7.28-7.33 (m, 5 H), 7.43 (d, J=8.31 Hz, 2 H), 7.56-7.60 (m, 2 H), 7.72-7.76 (m, 4 H), 8.12 (dd, J=7.82, 1.47 Hz, 2 H); $^{13}$C NMR (CDCl$_3$) δ 21.1, 53.9, 59.1, 67.6, 69.2, 70.2, 106.0, 115.0, 117.9, 121.2, 123.8, 123.9, 125.0, 125.5, 127.8, 129.6, 133.5, 137.4, 149.5, 156.0, 161.6, 163.1, 169.5, 178.1; LRMS (ESI) m/z 782 (M$^+$+H, 100), 805 (M$^+$+Na, 23); HRMS (ESI) Calcd for $C_{47}H_{44}NO_{10}$(M$^+$+H) 782.2965, found 782.2994.

Example 43

1,13-Bis[4'-(4H-chromen-4-on-2-yl)phenyl]-7-(4-hydroxybenzyl)-1,4,10,13-tetraoxa-7-azamidecane (42d). To a round-bottom flask was charged with compound 42c (0.30 g, 0.38 mmol) and 2M KOH solution (10 mL) in methanol. The reaction mixture was stirred at room temperature for 2 hr. When TLC indicated complete consumption of starting material, the reaction mixture was poured into a separating funnel containing water. The mixture was continuously extracted with $CH_2Cl_2$. The combined organic layers were dried over $MgSO_4$, filtered and evaporated to give a crude reaction mixture, which was subjected to purification by flash column chromatography on silica gel with 10-20% acetone in $CH_2Cl_2$ as eluent to furnish the titled compound 42d as pale brown oil (150 mg, 53%): $^1$H NMR (CDCl$_3$) δ 2.80 (t, J=6.11 Hz, 4 H), 3.62-3.70 (m, 6 H), 3.75-3.90 (m, 4 H), 4.09-4.19 (m, 4 H), 6.69 (s, 2 H), 6.88 (d, J=8.31 Hz, 2 H), 6.94-7.02 (m, 4 H), 7.20 (d, J=8.80 Hz, 2 H), 7.34-7.42 (m, 2 H), 7.49 (d, J=8.31 Hz, 2 H), 7.64 (ddd, J=8.44, 6.97, 1.71 Hz, 2 H), 7.75-7.96 (m, 4 H), 8.18 (dd, J=7.83, 1.47 Hz, 2 H); $^{13}$C NMR (CDCl$_3$) δ 53.7, 59.3, 67.7, 69.3, 70.1, 105.9, 115.1, 115.3, 118.0, 123.7, 123.9, 125.1, 125.6, 128.0, 130.2, 130.4, 133.7, 155.8, 156.1, 161.7, 163.5, 178.6; LRMS (ESI) m/z 740 (M$^+$+H, 100); HRMS (ESI) Calcd for $C_{45}H_{42}NO_9$(M$^+$+H) 740.2860, found 740.2855.

Example 44

1,13-Bis[4'-(4H-chromen-4-on-2-yl)phenyl]-7-(5-piperonyl)-1,4,10,13-tetraoxa-7-azamidecane (42e). To a round-bottom flask was charged with compound 12a (400 mg, 0.63 mmol), 5-(bromomethyl)-1,3-benzodioxole (160 mg, 0.74 mmol), $K_2CO_3$ (120 mg) and ACN (10 mL). The reaction mixture was stirred at refluxing temperature for 3 hr. When TLC indicated complete consumption of starting material, the hot reaction mixture was filtered to remove solid $K_2CO_3$. The filtrate was cooled in an ice bath and numerous white precipitate was formed. The titled compound 42e was obtained after suction filtration as an off-white solid (190 mg, 39%): m.p.: 69-70° C.; $^1$H NMR (CDCl$_3$) δ 2.78 (t, J=5.87 Hz, 4 H), 3.59-3.69 (m, 6 H), 3.79 (t, J=4.40 Hz, 4 H), 4.03-4.17 (m, 4 H), 5.89 (s, 2 H), 6.65-6.78 (m, 4 H), 6.89 (s, 1 H), 6.98 (d, J=8.80 Hz, 4 H), 7.28-7.39 (m, 2 H), 7.49 (d, J=8.31 Hz, 2 H), 7.63 (t, J=7.58 Hz, 2 H), 7.80 (d, J=8.31 Hz, 4 H), 8.16 (d, J=7.83 Hz, 2 H); $^{13}$C NMR (CDCl$_3$) δ 53.7, 59.5, 60.3, 67.7, 69.3, 70.2, 100.8, 106.1, 107.8, 109.2, 115.0, 117.9, 121.7, 123.9, 124.1, 125.0, 125.6, 127.9, 133.5, 146.5, 147.6, 156.1, 161.7, 163.2, 178.2; LRMS (ESI) m/z 768 (M$^+$+H, 75), 790 (M$^+$+Na, 46); HRMS (ESI) Calcd for $O_{46}H_{42}NO_{10}$(M$^+$+H) 768.2809, found 768.2776.

Example 45

1,13-Bis[4'-(4H-chromen-4-on-2-yl)phenyl]-7-[5-(6-chloropiperonyl)]-1,4,10,13-tetraoxa-7-azamidecane (42f). To a round-bottom flask was charged with compound 12a (0.40 g, 0.63 mmol), 6-chloropiperonyl chloride (0.16 g, 0.78 mmol), K₂CO₃ (120 mg) and ACN (20 mL). The reaction mixture was stirred at refluxing temperature for 3 hr. When TLC indicated complete consumption of starting material, the reaction mixture was poured into a separating funnel containing water. The mixture was continuously extracted with CH₂Cl₂. The combined organic layers were dried over MgSO₄, filtered and evaporated to give a crude reaction mixture, which was subjected to purification by flash column chromatography on silica gel with 10-20% acetone in CH₂Cl₂ as eluent to furnish the titled compound 42f as a white foam (0.17 g, 34%): $^1$H NMR (CDCl₃) δ 2.84 (t, J=5.87 Hz, 4 H), 3.67 (t, J=5.87 Hz, 4 H), 3.75 (s, 2 H), 3.79-3.84 (m, 4 H), 4.11-4.18 (m, 4 H), 5.92 (s, 2 H), 6.71 (s, 2 H), 6.78 (s, 1 H), 6.99-7.02 (m, 4 H), 7.15 (s, 1 H), 7.36-7.41 (m, 2 H), 7.52 (d, J=7.34 Hz, 2 H), 7.66 (ddd, J=8.44, 6.97, 1.71 Hz, 2 H), 7.81-7.85 (m, 4 H), 8.20 (dd, J=8.07, 1.71 Hz, 2 H); $^{13}$C NMR (CDCl₃) δ 54.2, 56.3, 67.7, 69.3, 70.2, 101.5, 106.2, 109.5, 110.0, 115.1, 117.9, 123.9, 124.1, 125.1, 125.6, 127.9, 133.5, 146.7, 146.8, 156.1, 161.7, 163.3, 178.3; LRMS (ESI) m/z 802 (M⁺+H, 100), 824 (M⁺+Na, 25); HRMS (ESI) Calcd for C₄₆H₄₁NO₁₀Cl(M⁺+H) 802.2419, found 802.2380.

Example 46

1,13-Bis[4'-(4H-chromen-4-on-2-yl)phenyl]-7-(3-methoxybenzyl)-1,4,10,13-tetraoxa-7-azamidecane (43). To a round-bottom flask was charged with compound 12a (230 mg, 0.36 mmol), 3-methoxybenzyl bromide (90 mg, 0.45 mmol), K₂CO₃ (70 mg) and ACN (20 mL). The reaction mixture was stirred at refluxing temperature for 3 hr. When TLC indicated complete consumption of starting material, the reaction mixture was poured into a separating funnel containing water. The mixture was continuously extracted with CH₂Cl₂. The combined organic layers were dried over MgSO₄, filtered and evaporated to give a crude reaction mixture, which was subjected to purification by flash column chromatography on silica gel with 10-20% acetone in CH₂Cl₂ as eluent to furnish the titled compound 43 as a white foam (120 mg, 44%): $^1$H NMR (CDCl₃) δ 2.88 (br, 4 H), 3.65-3.90 (m, 13H), 4.17 (t, J=4.49 Hz, 4 H), 6.73 (s, 2 H), 6.81 (d, J=7.80 Hz, 1 H), 6.93-7.16 (m, 6 H), 7.19-7.33 (m, 1 H), 7.40 (t, J=7.41 Hz, 2 H), 7.53 (d, J=8.20 Hz, 2 H), 7.64-7.75 (m, 2 H), 7.85 (d, J=8.98 Hz, 4 H), 8.18-8.24 (m, 2 H); $^{13}$C NMR (CDCl₃) δ 53.9, 55.2, 59.8, 67.7, 69.3, 70.2, 106.2, 115.1, 117.9, 123.9, 124.2, 125.1, 125.6, 128.0, 133.6, 147.5, 156.2, 161.6, 163.3, 178.3; LRMS (ESI) m/z 754 (M⁺+H, 100), 776 (M⁺+Na, 15); HRMS (ESI) Calcd for C₄₆H₄₄NO₉(M⁺+H) 754.3016, found 754.3005.

Example 47

1,13-Bis[4'-(4H-chromen-4-on-2-yl)phenyl]-7-(3,5-dimethoxybenzyl)-1,4,10,13-tetraoxa-7-azamidecane (44). To a round-bottom flask was charged with compound 12a (0.26 g, 0.41 mmol), 3,5-dimethoxybenzyl chloride (0.09 g, 0.48 mmol), K₂CO₃ (0.07 g) and ACN (20 mL). The reaction mixture was stirred at refluxing temperature for 3 hr. When TLC indicated complete consumption of starting material, the reaction mixture was poured into a separating funnel containing water. The mixture was continuously extracted with CH₂Cl₂. The combined organic layers were dried over MgSO₄, filtered and evaporated to give a crude reaction mixture, which was subjected to purification by flash column chromatography on silica gel with 10-20% acetone in CH₂Cl₂ as eluent to furnish the titled compound 44 as a white foam (0.15 g, 48%): $^1$H NMR (CDCl₃) δ 2.84 (br, 4 H), 3.69-3.70 (m, 6 H), 3.77 (s, 6H), 3.74-3.85 (m, 4 H), 4.12-4.19 (m, 4 H), 6.35 (t, J=2.15 Hz, 1 H), 6.56 (br, 2 H), 6.72 (s, 2 H), 7.01 (d, J=8.98 Hz, 4 H), 7.39 (t, J=7.61 Hz, 2 H), 7.52 (d, J=8.20 Hz, 2 H), 7.67 (ddd, J=8.59, 7.02, 1.56 Hz, 2 H), 7.84 (d, J=8.98 Hz, 4 H), 8.20 (dd, J=7.80, 1.17 Hz, 2 H); $^{13}$C NMR (CDCl₃) δ 54.0, 55.3, 56.0, 67.7, 69.3, 70.2, 106.2, 106.6, 115.0, 117.9, 123.9, 124.1, 125.1, 125.6, 127.9, 133.6, 156.1, 160.7, 161.7, 163.3, 178.3; LRMS (ESI) m/z 784 (M⁺+H, 100), 806 (M⁺+Na, 48); HRMS (ESI) Calcd for C₄₇H₄₆NO₁₀(M⁺+H) 784.3122, found 784.3107.

Example 48

1,13-Bis[4'-(4H-chromen-4-on-2-yl)phenyl]-7-(3-methylbenzyl)-1,4,10,13-tetraoxa-7-azamidecane (45). To a round-bottom flask was charged with compound 12a (350 mg, 0.55 mmol), 3-methylbenzyl bromide (120 mg, 0.65 mmol), K₂CO₃ (100 mg) and ACN (20 mL). The reaction mixture was stirred at refluxing temperature for 3 hr. When TLC indicated complete consumption of starting material, the reaction mixture was poured into a separating funnel containing water. The mixture was continuously extracted with CH₂Cl₂. The combined organic layers were dried over MgSO₄, filtered and evaporated to give a crude reaction mixture, which was subjected to purification by flash column chromatography on silica gel with 10-20% acetone in CH₂Cl₂ as eluent to furnish the titled compound 45 as a white foam (190 mg, 47%): $^1$H NMR (CDCl₃) δ 2.34 (s, 3 H), 2.90 (br, 4 H), 3.66-3.93 (m, 10 H), 4.02-4.30 (m, 4 H), 6.73 (s, 2 H), 7.02 (d, J=8.98 Hz, 4 H), 7.09 (br, 1 H), 7.21 (br, 2 H), 7.34-7.44 (m, 2 H), 7.54 (d, J=8.59 Hz, 2 H), 7.68 (ddd, J=8.39, 7.02, 1.76 Hz, 2 H), 7.85 (d, J=8.98 Hz, 4 H), 8.22 (dd, J=7.81, 1.56 Hz, 2 H); $^{13}$C NMR (CDCl₃) δ 21.4, 53.6, 59.7, 67.6, 69.3, 70.2, 106.2, 115.1, 117.9, 123.9, 124.2, 125.1, 125.7, 128.0, 133.6, 156.2, 161.6, 163.3, 178.3; LRMS (ESI) m/z 738 (M⁺+H, 100), 760 (M⁺+Na, 18); HRMS (ESI) Calcd for C₄₆H₄₄NO₈(M⁺+H) 738.3067, found 738.3080.

Example 49

1,13-Bis[4'-(4H-chromen-4-on-2-yl)phenyl]-7-(2-methylbenzyl)-1,4,10,13-tetraoxa-7-azamidecane (46). To a round-bottom flask was charged with compound 12a (400 mg, 0.63 mmol), 2-methylbenzyl bromide (160 mg, 0.86 mmol), K₂CO₃ (100 mg) and ACN (20 mL). The reaction mixture was stirred at refluxing temperature for 3 hr. When TLC indicated complete consumption of starting material, the reaction mixture was poured into a separating funnel containing water. The mixture was continuously extracted with CH₂Cl₂. The combined organic layers were dried over MgSO₄, filtered and evaporated to give a crude reaction mixture, which was subjected to purification by flash column chromatography on silica gel with 10-20% acetone in CH₂Cl₂ as eluent to furnish the titled compound 46 as a white foam (260 mg, 56%): $^1$H NMR (CDCl₃) δ 2.38 (s, 3H), 2.83 (t, J=4.50 Hz, 4H), 3.65 (t, J=4.50 Hz, 4H), 3.69 (s, 2H), 3.79 (t, J=4.50 Hz, 4H), 4.11 (t, J=4.51 Hz, 4H), 6.73 (s, 2H), 7.02 (d, J=8.0 Hz, 4H), 7.16 (br, 3H), 7.38 (br, 1H), 7.41 (dd, J=7.80, 1.60 Hz, 2H), 7.54 (d, J=8.0 Hz, 2H), 7.69 (ddd, J=8.39, 7.02, 1.76 Hz, 2 H), 7.86 (d, J=8.0 Hz, 4H), 8.21 (dd, J=7.80, 1.60 Hz, 2H); $^{13}$C NMR (CDCl₃) δ 19.3, 54.1, 58.3, 67.7, 69.2, 70.3, 106.2, 115.1, 117.9, 123.9, 124.1, 125.1, 125.6, 127.9, 130.2, 133.5, 137.3, 156.2, 161.7, 163.3, 178.3; LRMS (ESI) m/z 738 (M⁺+H, 100), 760 (M⁺+Na, 25); HRMS (ESI) Calcd for C₄₆H₄₄NO₈(M⁺+H) 738.3067, found 738.3049.

Example 50

1,13-Bis[4'-(4H-chromen-4-on-2-yl)phenyl]-7-(4-methylbenzyl)-1,4,10,13-tetraoxa-7-azamidecane (47). To a round-bottom flask was charged with compound 12a (220 mg, 0.35 mmol), 4-methylbenzyl bromide (100 mg, 0.54 mmol), $K_2CO_3$ (80 mg) and ACN (20 mL). The reaction mixture was stirred at refluxing temperature for 3 hr. When TLC indicated complete consumption of starting material, the reaction mixture was poured into a separating funnel containing water. The mixture was continuously extracted with $CH_2Cl_2$. The combined organic layers were dried over $MgSO_4$, filtered and evaporated to give a crude reaction mixture, which was subjected to purification by flash column chromatography on silica gel with 10-20% acetone in $CH_2Cl_2$ as eluent to furnish the titled compound 47 as a white foam (153 mg, 60%): $^1H$ NMR (CDCl$_3$) δ 2.31 (s, 3 H), 2.81 (t, J=5.87 Hz, 4 H), 3.63-3.71 (m, 6 H), 3.77-3.81 (m, 4 H), 4.09-4.14 (m, 4 H), 6.67 (s, 2 H), 6.94-6.98 (m, 4 H), 7.07-7.11 (m, 2 H), 7.22 (d, J=7.82 Hz, 4 H), 7.32-7.37 (m, 2 H), 7.47 (d, J=8.31 Hz, 2 H), 7.62 (ddd, J=8.56, 7.09, 1.96 Hz, 2 H), 7.76-7.80 (m, 4 H), 8.16 (dd, J=8.07, 1.71 Hz, 2 H); $^{13}C$ NMR (CDCl$_3$) δ 21.1, 53.8, 59.5, 67.7, 69.2, 70.2, 106.0, 115.0, 116.4, 117.9, 123.8, 123.9, 125.1, 125.5, 127.9, 128.1, 128.8, 128.9, 133.6, 136.4, 156.1, 161.7, 163.3, 178.3; LRMS (ESI) m/z 738 (M$^+$+H, 100), 760 (M$^+$+Na, 25); HRMS (ESI) Calcd for $C_{46}H_{44}NO_8$(M$^+$+H) 738.3067, found 738.3082.

Example 51

1,13-Bis[4'-(4H-chromen-4-on-2-yl)phenyl]-7-(3-chlorobenzyl)-1,4,10,13-tetraoxa-7-azamidecane (48). To a round-bottom flask was charged with compound 12a (230 mg, 0.36 mmol), 3-chlorobenzyl bromide (90 mg, 0.44 mmol), $K_2CO_3$ (70 mg) and ACN (20 mL). The reaction mixture was stirred at refluxing temperature for 3 hr. When TLC indicated complete consumption of starting material, the reaction mixture was poured into a separating funnel containing water. The mixture was continuously extracted with $CH_2Cl_2$. The combined organic layers were dried over $MgSO_4$, filtered and evaporated to give a crude reaction mixture, which was subjected to purification by flash column chromatography on silica gel with 10-20% acetone in $CH_2Cl_2$ as eluent to furnish the titled compound 48 as a white foam (160 mg, 58%): $^1H$ NMR (CDCl$_3$) δ 2.86 (br, 4 H), 3.63-3.90 (m, 10 H), 4.17 (br, 4 H), 6.72 (s, 2 H), 7.01 (d, J=8.20 Hz, 4 H), 7.23 (br, 2 H), 7.34-7.47 (m, 3 H), 7.53 (d, J=8.20 Hz, 2 H), 7.67 (t, J=7.02 Hz, 2 H), 7.84 (d, J=8.20 Hz, 4 H), 8.21 (d, J=7.41 Hz, 2 H); $^{13}C$ NMR (CDCl$_3$) δ 53.9, 59.2, 67.6, 69.3, 70.1, 106.2, 115.0, 117.9, 123.9, 124.2, 125.1, 125.6, 127.9, 133.6, 134.2, 156.1, 161.6, 163.2, 178.3; LRMS (ESI) m/z 758 (M$^+$+H, 100), 780 (M$^+$+Na, 65); HRMS (ESI) Calcd for $C_{45}H_{41}NO_8Cl$(M$^+$+H) 758.2521, found 758.2495.

Example 52

1,13-Bis[4'-(4H-chromen-4-on-2-yl)phenyl]-7-(4-chlorobenzyl)-1,4,10,13-tetraoxa-7-azamidecane (49). To a round-bottom flask was charged with compound 12a (230 mg, 0.36 mmol), 4-chlorobenzyl bromide (90 mg, 0.44 mmol), $K_2CO_3$ (70 mg) and ACN (10 mL). The reaction mixture was stirred at refluxing temperature for 3 hr. When TLC indicated complete consumption of starting material, the hot reaction mixture was filtered to remove solid $K_2CO_3$. The filtrate was cooled in an ice bath and numerous white precipitate was formed. The titled compound 49 was obtained after suction filtration as an off-white solid (186 mg, 68%): m.p.: 81-82° C.; $^1H$ NMR (CDCl$_3$) δ 2.83 (br, 4 H), 3.55-3.83 (br, 10H), 4.17 (br, 4 H), 6.73 (s, 2 H), 7.01 (d, J=8.59 Hz, 4 H), 7.28 (d, J=4.68 Hz, 4 H), 7.31-7.45 (m, 2 H), 7.54 (d, J=8.20 Hz, 2 H), 7.62-7.75 (m, 2 H), 7.85 (d, J=8.98 Hz, 4 H), 8.21 (d, J=7.81 Hz, 2 H); $^{13}C$ NMR (CDCl$_3$) δ 53.9, 59.1, 67.6, 69.3, 70.3, 106.2, 115.0, 117.9, 123.9, 124.2, 125.1, 125.6, 127.9, 133.6, 138.8, 156.2, 161.6, 163.2, 175.7, 178.3; LRMS (ESI) m/z 758 (M$^+$+H, 100); HRMS (ESI) Calcd for $C_{45}H_{41}NO_8Cl$(M$^+$+H) 758.2521, found 758.2512.

Example 53

1,13-Bis[4'-(4H-chromen-4-on-2-yl)phenyl]-7-(2-chlorobenzyl)-1,4,10,13-tetraoxa-7-azamidecane (50). To a round-bottom flask was charged with compound 12a (230 mg, 0.36 mmol), 2-chlorobenzyl bromide (90 mg, 0.44 mmol), $K_2CO_3$ (70 mg) and ACN (10 mL). The reaction mixture was stirred at refluxing temperature for 3 hr. When TLC indicated complete consumption of starting material, the reaction mixture was poured into a separating funnel containing water. The mixture was continuously extracted with $CH_2Cl_2$. The combined organic layers were dried over $MgSO_4$, filtered and evaporated to give a crude reaction mixture, which was subjected to purification by flash column chromatography on silica gel with 10-20% acetone in $CH_2Cl_2$ as eluent to furnish the titled compound 50 as a white foam (163 mg, 59%): $^1H$ NMR (CDCl$_3$) δ 2.93 (br, 4 H), 3.75-3.83 (m, 10 H), 4.00-4.26 (m, 4 H), 6.73 (s, 2 H), 7.01 (d, J=8.59 Hz, 4 H), 7.17-7.44 (m, 4 H), 7.53 (d, J=8.20 Hz, 2 H), 7.60-7.75 (m, 2 H) 7.84 (d, J=8.98 Hz, 4 H), 8.18-8.27 (m, 2 H); $^{13}C$ NMR (CDCl$_3$) δ 54.1, 59.7, 67.6, 69.4, 70.5, 106.2, 115.0, 117.9, 123.9, 124.2, 125.1, 125.6, 127.9, 133.6, 156.2, 161.6, 163.3, 175.5, 178.4; LRMS (ESI) m/z 758 (M$^+$+H, 100); HRMS (ESI) Calcd for $C_{45}H_{41}NO_8Cl$(M$^+$+H) 758.2521, found 758.2486.

Example 54

1,13-Bis[4'-(4H-chromen-4-on-2-yl)phenyl]-7-(4-cyanobenzyl)-1,4,10,13-tetraoxa-7-azamidecane (51). To a round-bottom flask was charged with compound 12a (210 mg, 0.33 mmol), 4-(bromomethyl)benzonitrile (91 mg, 0.46 mmol), $K_2CO_3$ (70 mg) and ACN (10 mL). The reaction mixture was stirred at refluxing temperature for 3 hr. When TLC indicated complete consumption of starting material, the reaction mixture was poured into a separating funnel containing water. The mixture was continuously extracted with $CH_2Cl_2$. The combined organic layers were dried over $MgSO_4$, filtered and evaporated to give a crude reaction mixture, which was subjected to purification by flash column chromatography on silica gel with 10-20% acetone in $CH_2Cl_2$ as eluent to furnish the titled compound 51 as a white foam (153 mg, 62%): $^1H$ NMR (CDCl$_3$) δ 2.83 (br, 4 H), 3.67 (br, 4 H), 3.74-3.94 (m, 6 H), 4.16 (br, 4 H), 6.73 (s, 2 H), 7.00 (d, J=8.59 Hz, 4 H), 7.40 (t, J=7.41 Hz, 2 H), 7.47-7.61 (m, 6 H), 7.62-7.74 (m, 2 H), 7.85 (d, J=8.59 Hz, 4 H), 8.20 (d, J=7.41 Hz, 2 H); $^{13}C$ NMR (CDCl$_3$) δ 54.1, 59.4, 67.6, 69.3, 70.2, 106.2, 110.6, 115.0, 118.0, 123.9, 124.2, 125.1, 125.6, 128.0, 129.1, 132.0, 133.6, 146.1, 156.1, 161.5, 163.2, 178.3; LRMS (ESI) m/z 749 (M$^+$+H, 50), 771 (M$^+$+Na, 100); HRMS (ESI) Calcd for $C_{46}H_{41}N_2O_8$(M$^+$+H) 749.2863, found 749.2847.

Example 55

1,13-Bis[4'-(4H-chromen-4-on-2-yl)phenyl]-7-(4-vinylbenzyl)-1,4,10,13-tetraoxa-7-azamidecane (52). To a round-bottom flask was charged with compound 12a (210 mg, 0.33 mmol), 4-vinylbenzyl chloride (91 mg, 0.59 mmol), $K_2CO_3$ (70 mg) and ACN (10 mL). The reaction mixture was stirred at refluxing temperature for 3 hr. When TLC indicated complete consumption of starting material, the reaction mixture was poured into a separating funnel containing water. The mixture was continuously extracted with $CH_2Cl_2$. The combined organic layers were dried over $MgSO_4$, filtered and evaporated to give a crude reaction mixture, which was subjected to purification by flash column chromatography on silica gel with 10-20% acetone in $CH_2Cl_2$ as eluent to furnish the titled compound 52 as a white foam (142 mg, 57%): $^1H$ NMR ($CDCl_3$) δ 2.83 (br, 4 H), 3.67 (br, 4 H), 3.74 (br, 4 H), 3.77-3.94 (m, 6 H), 4.14 (br, 4 H), 5.21 (d, J=10.54 Hz, 1 H), 5.71 (d, J=17.56 Hz, 1 H), 6.62-6.81 (m, 3 H), 6.99 (d, J=8.59 Hz, 4 H), 7.24-7.44 (m, 6 H), 7.50 (d, J=8.20 Hz, 2 H), 7.65 (t, J=7.02 Hz, 2 H), 7.82 (d, J=8.20 Hz, 4 H), 8.18 (d, J=7.41 Hz, 2 H); $^{13}C$ NMR ($CDCl_3$) δ 53.9, 59.5, 67.7, 69.2, 70.1, 106.1, 113.4, 115.0, 117.9, 123.9, 124.0, 125.1, 125.6, 126.1, 127.9, 129.0, 133.6, 136.3, 136.6, 139.2, 156.1, 161.6, 163.3, 178.3; LRMS (ESI) m/z 750 ($M^+$+H, 100), 772 ($M^+$+Na, 35); HRMS (ESI) Calcd for $C_{47}H_{44}NO_8(M^++H)$ 750.3067, found 750.3073.

Example 56

1,13-Bis[4'-(4H-chromen-4-on-2-yl)phenyl]-7-(4-ethylbenzyl)-1,4,10,13-tetraoxa-7-azamidecane (53). To a round-bottom flask was charged with compound 52 (90 mg, 0.12 mmol), 10% Pd/C (50 mg) and chloroform (20 mL). The reaction mixture was stirred at room temperature for 4 hr under hydrogen atmosphere at balloon pressure. When TLC indicated complete consumption of starting material, the reaction mixture was filtered and evaporated to give a crude reaction mixture, which was subjected to purification by flash column chromatography on silica gel with 10-20% acetone in $CH_2Cl_2$ as eluent to furnish the titled compound 53 as a white foam (60 mg, 66%): $^1H$ NMR ($CDCl_3$) δ 1.23 (t, J=7.61 Hz, 3 H), 2.64 (q, J=7.80 Hz, 2 H), 2.85 (br, 4 H), 3.66-3.78 (m, 6 H), 3.78-3.90 (m, 4 H), 4.14-4.22 (m, 4 H), 6.72 (s, 2 H), 6.99-7.07 (m, 4 H), 7.14 (d, J=7.81 Hz, 2 H), 7.28 (d, J=7.02 Hz, 2 H), 7.37-7.43 (m, 2 H), 7.51-7.56 (m, 2 H), 7.65-7.71 (m, 2 H), 7.82-7.90 (m, 4 H), 8.21 (dd, J=7.81, 1.56 Hz, 2 H); $^{13}C$ NMR ($CDCl_3$) δ 15.6, 28.5, 53.8, 59.5, 67.7, 69.3, 70.1, 106.2, 115.0, 117.9, 123.9, 124.1, 125.1, 125.6, 127.7, 127.9, 129.0, 133.6, 156.1, 161.6, 163.3, 178.3; LRMS (ESI) m/z 752 ($M^+$+H, 100), 774 ($M^+$+Na, 41); HRMS (ESI) Calcd for $C_{47}H_{46}NO_8(M^++H)$ 752.3223, found 752.3201.

Example 57

1,13-Bis[4'-(4H-chromen-4-on-2-yl)phenyl]-7-(4-tert-butyloxycarbonylaminobenzyl)-1,4,10,13-tetraoxa-7-azamidecane (54). To a round-bottom flask was charged with compound 12a (550 mg, 0.87 mmol), tert-butyl (4-(bromomethyl)phenyl)carbamate (150 mg, 0.52 mmol), $K_2CO_3$ (130 mg) and ACN (20 mL). The reaction mixture was stirred at refluxing temperature for 3 hr. When TLC indicated complete consumption of starting material, the reaction mixture was poured into a separating funnel containing water. The mixture was continuously extracted with $CH_2Cl_2$. The combined organic layers were dried over $MgSO_4$, filtered and evaporated to give a crude reaction mixture, which was subjected to purification by flash column chromatography on silica gel with 10-20% acetone in $CH_2Cl_2$ as eluent to furnish the titled compound 54 as a white foam (340 mg, 77%): $^1H$ NMR ($CDCl_3$) δ 1.48 (s, 9 H), 2.79 (t, J=5.87 Hz, 4 H), 3.60-3.72 (m, 6 H), 3.78 (t, J=5.14 Hz, 4 H), 4.06-4.18 (m, 4 H), 6.66 (s, 2 H), 6.90 (br, 1 H), 6.93-7.14 (m, 4 H), 7.23-7.40 (m, 6 H), 7.42-7.53 (m, 2 H), 7.55-7.69 (m, 2 H), 7.73-7.87 (m, 4 H), 8.17 (dd, J=7.83, 1.96 Hz, 2 H); $^{13}C$ NMR ($CDCl_3$) δ 28.3, 53.8, 59.3, 67.7, 69.2, 70.2, 80.2, 106.1, 115.0, 117.9, 118.4, 123.9, 124.0, 125.0, 125.6, 127.9, 129.4, 133.5, 137.4, 152.9, 156.1, 161.7, 163.3, 178.3; LRMS (ESI) m/z 839 ($M^+$+H, 100), 861 ($M^+$+Na, 26); HRMS (ESI) Calcd for $C_{50}H_{51}N_2O_{10}(M^++H)$ 839.3544, found 839.3511.

Example 58

1,13-Bis[4'-(4H-chromen-4-on-2-yl)phenyl]-7-(4-aminobenzyl)-1,4,10,13-tetraoxa-7-azamidecane (55). The titled compound 55 was obtained from 54 (310 mg, 0.37 mmol), TFA (10 mL) and $CH_2Cl_2$ (10 mL) as a white foam (260 mg, 95%) according to the general procedure II described above: $^1H$ NMR ($CDCl_3$) δ 2.81 (br, 4 H), 3.66 (br, 6 H), 3.82-3.81 (m, 4 H), 4.12-4.19 (m, 4 H), 6.61-6.66 (m, 2 H), 6.71 (s, 2 H), 6.98-7.04 (m, 4 H), 7.12 (d, J=8.31 Hz, 2 H), 7.33-7.41 (m, 2 H), 7.49-7.54 (m, 2 H), 7.63-7.68 (m, 2 H), 7.80-7.86 (m, 4 H), 8.20 (dd, J=7.82, 1.47 Hz, 2 H); $^{13}C$ NMR ($CDCl_3$) δ 53.6, 59.3, 67.7, 69.2, 70.2, 106.1, 114.9, 115.1, 117.9, 123.9, 124.1, 125.0, 125.6, 127.9, 129.4, 133.5, 156.1, 161.7, 163.3, 178.3; LRMS (ESI) m/z 739 ($M^+$+H, 20), 761 ($M^+$+Na, 10); HRMS (ESI) Calcd for $C_{45}H_{43}N_2O_8(M^++H)$ 739.3019, found 739.3004.

Example 59

1,13-Bis[4'-(4H-chromen-4-on-2-yl)phenyl]-7-(3-phenylbenzyl)-1,4,10,13-tetraoxa-7-azamidecane (56). To a round-bottom flask was charged with compound 12a (280 mg, 0.44 mmol), 3-phenylbenzyl bromide (150 mg, 0.61 mmol), $K_2CO_3$ (80 mg) and ACN (10 mL). The reaction mixture was stirred at refluxing temperature for 3 hr. When TLC indicated complete consumption of starting material, the reaction mixture was poured into a separating funnel containing water. The mixture was continuously extracted with $CH_2Cl_2$. The combined organic layers were dried over $MgSO_4$, filtered and evaporated to give a crude reaction mixture, which was subjected to purification by flash column chromatography on silica gel with 10-20% acetone in $CH_2Cl_2$ as eluent to furnish the titled compound 56 as a white foam (225 mg, 64%): $^1H$ NMR ($CDCl_3$) δ 2.90 (br, 4 H), 3.73-3.99 (m, 10 H), 4.07-4.26 (m, 4 H), 6.71 (s, 2 H), 6.97 (d, J=8.98 Hz, 4 H), 7.32-7.55 (m, 7 H), 7.56-7.72 (m, 9 H), 7.81 (d, J=8.59 Hz, 4 H), 8.21 (d, J=7.80 Hz, 2 H); $^{13}C$ NMR ($CDCl_3$) δ 53.9, 59.8, 67.6, 69.3, 70.7, 106.1, 115.0, 116.3, 117.9, 123.9, 124.1, 125.1, 125.6, 125.8, 127.1, 127.2, 127.9, 128.7, 133.5, 141.1, 156.1, 161.6, 163.2, 178.3; LRMS (ESI) m/z 800 ($M^+$+H, 100), 822 ($M^+$+Na, 17); HRMS (ESI) Calcd for $C_{51}H_{46}NO_8(M^++H)$ 800.3223, found 800.3190.

Example 60

1,13-Bis[4'-(4H-chromen-4-on-2-yl)phenyl]-7-(4-phenylbenzyl)-1,4,10,13-tetraoxa-7-azamidecane (57). To a round-bottom flask was charged with compound 12a (220 mg, 0.35 mmol), 4-phenylbenzyl chloride (120 mg, 0.59 mmol), $K_2CO_3$ (70 mg) and ACN (10 mL). The reaction mixture was stirred at refluxing temperature for 3 hr. When TLC indicated complete consumption of starting material, the hot reaction mixture was filtered to remove solid $K_2CO_3$. The filtrate was cooled in an ice bath and numerous white precipitate was formed. The titled compound 57 was obtained after suction filtration as a white solid (148 mg, 53%): m.p.: 106-107° C.; $^1H$ NMR ($CDCl_3$) δ 2.90 (br, 4 H), 3.80-3.85 (br, 10 H), 4.02-4.28 (m, 4 H), 6.73 (m, 2 H), 7.02 (d, J=8.98 Hz, 4 H), 7.34 (d, J=7.02 Hz, 1 H), 7.38-7.62 (m, 12 H), 7.63-7.74 (m, 2 H), 7.84 (d, J=8.98 Hz, 4 H), 8.19-8.26 (m, 2 H); $^{13}C$ NMR ($CDCl_3$) δ 53.7, 59.4, 67.6, 69.3, 70.8, 106.2, 115.1, 117.9, 123.9, 124.2, 125.1, 125.6, 126.9, 127.5, 127.9, 128.7, 133.6, 156.2, 161.6, 163.3, 178.3; LRMS (ESI) m/z 800 (M$^+$+H, 100), 822 (M$^+$+Na, 17); HRMS (ESI) Calcd for $C_{51}H_{46}NO_8$ (M$^+$+H) 800.3223, found 800.3199.

Example 61

1,13-Bis[4'-(4H-chromen-4-on-2-yl)phenyl]-7-(2-naphthalenylmethyl)-1,4,10,13-tetraoxa-7-azamidecane (58). To a round-bottom flask was charged with compound 12a (230 mg, 0.36 mmol), 2-(bromomethyl)naphthalene (85 mg, 0.38 mmol), $K_2CO_3$ (70 mg) and ACN (10 mL).

The reaction mixture was stirred at refluxing temperature for 3 hr. When TLC indicated complete consumption of starting material, the reaction mixture was poured into a separating funnel containing water. The mixture was continuously extracted with $CH_2Cl_2$. The combined organic layers were dried over $MgSO_4$, filtered and evaporated to give a crude reaction mixture, which was subjected to purification by flash column chromatography on silica gel with 10-20% acetone in $CH_2Cl_2$ as eluent to furnish the titled compound 58 as a white foam (149 mg, 54%): $^1$H NMR (CDCl$_3$) δ 2.89-2.97 (m, 4 H), 3.68-3.93 (m, 6 H), 4.10-4.20 (m, 4 H), 6.71 (m, 2 H), 6.96-7.04 (m, 4 H), 7.36-7.55 (m, 5 H), 7.63-7.72 (m, 2 H), 7.74-7.87 (m, 7 H) 8.18-8.23 (m, 2 H); $^{13}$C NMR (CDCl$_3$) δ 54.1, 60.1, 67.6, 69.3, 70.3, 106.2, 115.0, 117.9, 123.9, 124.1, 124.2, 125.1, 125.5, 125.6, 125.9, 127.2, 127.7, 127.8, 127.9, 128.0, 132.7, 133.3, 133.6, 156.1, 161.6, 161.6, 163.2, 163.3, 178.3, 178.3; LRMS (ESI) m/z 774 (M$^+$+H, 42), 796 (M$^+$+Na, 20); HRMS (ESI) Calcd for $C_{49}H_{44}NO_8$(M$^+$+H) 774.3067, found 774.3052.

Example 62

1,13-Bis[4'-(4H-chromen-4-on-2-yl)phenyl]-7-(1-naphthalenylmethyl)-1,4,10,13-tetraoxa-7-azamidecane (59). To a round-bottom flask was charged with compound 12a (230 mg, 0.36 mmol), 1-(bromomethyl)naphthalene (85 mg, 0.38 mmol), $K_2CO_3$ (70 mg) and ACN (10 mL). The reaction mixture was stirred at refluxing temperature for 3 hr. When TLC indicated complete consumption of starting material, the hot reaction mixture was filtered to remove solid $K_2CO_3$. The filtrate was cooled in an ice bath and numerous white precipitate was formed. The titled compound 59 was obtained after suction filtration as a white solid (178 mg, 63%): m.p.: 96-97° C.; $^1$H NMR (CDCl$_3$) δ 2.91 (br, 4 H), 3.68 (br, 4 H), 3.77 (br, 4 H), 4.09 (br, 4 H), 4.18 (br, 2 H), 6.72 (s, 2 H), 6.93-7.07 (m, 4 H), 7.41 (d, J=7.02 Hz, 4 H), 7.45-7.59 (m, 4 H), 7.68 (br, 2 H), 7.72-7.95 (m, 6 H), 8.22 (d, J=7.41 Hz, 2 H) 8.36 (s, 1 H); $^{13}$C NMR (CDCl$_3$) δ 54.3, 62.9, 67.7, 69.2, 70.2, 106.2, 115.0, 117.9, 123.9, 124.2, 125.1, 125.7, 127.9, 128.5, 133.6, 133.9, 135.9, 156.2, 161.6, 163.3, 178.3; LRMS (ESI) m/z 774 (M$^+$+H, 100), 796 (M$^+$+Na, 14); HRMS (ESI) Calcd for $C_{49}H_{44}NO_8$(M$^+$+H) 774.3067, found 774.3102.

Example 63

1,13-Bis[4'-(4H-chromen-4-on-2-yl)phenyl]-7-(2-benzimidazolylmethyl)-1,4,10,13-tetraoxa-7-azamidecane (60). To a round-bottom flask was charged with compound 12a (300 mg, 0.47 mmol), 2-(chloromethyl)benzimidazole (100 mg, 0.60 mmol), $K_2CO_3$ (90 mg) and ACN (20 mL). The reaction mixture was stirred at refluxing temperature for 3 hr. When TLC indicated complete consumption of starting material, the reaction mixture was poured into a separating funnel containing water. The mixture was continuously extracted with $CH_2Cl_2$. The combined organic layers were dried over $MgSO_4$, filtered and evaporated to give a crude reaction mixture, which was subjected to purification by flash column chromatography on silica gel with 10-20% acetone in $CH_2Cl_2$ as eluent to furnish the titled compound 60 as a white foam (163 mg, 45%): $^1$H NMR (CDCl$_3$) δ 2.90 (t, J=5.07 Hz, 4 H), 3.67 (t, J=4.88 Hz, 4 H), 3.77-3.81 (m, 4 H), 4.10-4.20 (m, 6 H), 6.63 (s, 2 H), 6.88-6.92 (m, 4 H), 7.10-7.15 (m, 2 H), 7.28-7.35 (m, 2 H), 7.42-7.49 (m, 4 H), 7.58-7.68 (m, 2 H), 7.71-7.75 (m, 4 H), 8.14 (dd, J=8.00, 1.76 Hz, 2 H); $^{13}$C NMR (CDCl$_3$) δ 53.3, 54.9, 67.5, 69.2, 69.8, 106.1, 114.7, 114.9, 117.9, 122.0, 123.8, 124.2, 125.0, 125.5, 127.8, 127.9, 133.6, 154.0, 156.0, 161.3, 163.1, 178.2; LRMS (ESI) m/z 764 (M$^+$+H, 100); HRMS (ESI) Calcd for $C_{46}H_{42}N_3O_8$(M$^+$+H) 764.2972, found 764.2948.

Example 64

1,13-Bis[4'-(4H-chromen-4-on-2-yl)phenyl]-7-(4-benzoylbenzyl)-1,4,10,13-tetraoxa-7-azamidecane (61). To a round-bottom flask was charged with compound 12a (280 mg, 0.44 mmol), 4-(bromomethyl)benzophenone (150 mg, 0.55 mmol), $K_2CO_3$ (80 mg) and ACN (10 mL). The reaction mixture was stirred at refluxing temperature for 3 hr. When TLC indicated complete consumption of starting material, the hot reaction mixture was filtered to remove solid $K_2CO_3$. The filtrate was cooled in an ice bath and numerous white precipitate was formed. The titled compound 61 was obtained after suction filtration as a white solid (239 mg, 65%): m.p.: 71-72° C.; $^1$H NMR (CDCl$_3$) δ 2.89 (br, 4 H), 3.72 (br, 4 H), 3.83 (br, 6 H), 4.16 (br, 4 H), 6.70 (s, 2 H), 7.00 (d, J=7.80 Hz, 4 H), 7.36-7.59 (m, 10 H), 7.66-7.88 (m, 11 H), 8.19 (d, J=7.41 Hz, 2 H); $^{13}$C NMR (CDCl$_3$) δ 54.1, 59.5, 67.7, 68.2, 69.3, 106.2, 115.0, 116.3, 117.9, 123.9, 124.2, 125.1, 125.6, 127.9, 128.2, 128.8, 129.9, 130.2, 130.9, 132.3, 133.6, 145.3, 156.1, 161.6, 162.5, 163.2, 178.3; LRMS (ESI) m/z 828 (M$^+$+H, 100), 850 (M$^+$+Na, 30); HRMS (ESI) Calcd for $C_{52}H_{46}NO_9$(M$^+$+H) 828.3173, found 828.3206.

Example 65

1,13-Bis[4'-(4H-chromen-4-on-2-yl)phenyl]-7-(cyclohexanylmethyl)-1,4,10,13-tetraoxa-7-azamidecane (62). To a round-bottom flask was charged with compound 12a (350 mg, 0.55 mmol), (bromomethyl)cyclohexane (180 mg, 1.02 mmol), $K_2CO_3$ (150 mg) and DMF (10 mL). The reaction mixture was stirred at refluxing temperature for 3 hr. When TLC indicated complete consumption of starting material, the reaction mixture was poured into a separating funnel containing water. The mixture was continuously extracted with $CH_2Cl_2$. The combined organic layers were dried over $MgSO_4$, filtered and evaporated to give a crude reaction mixture, which was subjected to purification by flash column chromatography on silica gel with 10-20% acetone in $CH_2Cl_2$ as eluent to furnish the titled compound 62 as a white foam (130 mg, 32%): $^1$H NMR (CDCl$_3$) δ 0.83 (d, J=11.74 Hz, 2 H), 1.10-1.29 (m, 3 H), 1.31-1.34 (m, 1 H), 1.63-1.74 (m, 3 H), 1.80 (d, J=12.72 Hz, 2 H), 2.32 (d, J=6.85 Hz, 2 H), 2.76 (t, J=5.87 Hz, 4 H), 3.64 (t, J=6.11 Hz, 4 H), 3.81-3.89 (m, 4 H), 4.14-4.22 (m, 4 H), 6.73 (s, 2 H), 6.97-7.07 (m, 4 H), 7.37-7.43 (m, 2 H), 7.53 (d, J=8.31 Hz, 2 H), 7.67 (ddd, J=8.56, 7.09, 1.47 Hz, 2 H), 7.83-7.90 (m, 4 H), 8.20 (dd, J=8.07, 1.71 Hz, 2 H); $^{13}$C NMR (CDCl$_3$) δ 26.2, 26.8, 31.8, 36.5, 54.9, 62.9, 67.8, 69.3, 70.3, 106.2, 115.0, 117.9, 123.9, 124.1, 125.1, 125.6, 127.9, 133.6, 156.1, 161.7, 163.3, 178.3; LRMS (ESI) m/z 730 (M$^+$+H, 100), 752 (M$^+$+Na, 30); HRMS (ESI) Calcd for $C_{45}H_{48}NO_8$(M$^+$+H) 730.3380, found 730.3344.

General Procedure III for Synthesis of Diols 63a-g According to Scheme 3. To a round-bottom flask was charged with amino diol 65, corresponding arylmethyl bromide, excess $K_2CO_3$ and acetone. The reaction mixture was stirred at refluxing temperature for 3 hr. When TLC indicated complete consumption of starting material, the reaction mixture was cooled and filtered to remove excess $K_2CO_3$. The obtained filtrate was evaporated to give a crude reaction mixture, which was subjected to purification by flash column chromatography on silica gel with 3-20% MeOH in $CH_2Cl_2$ as eluent to furnish the desired compound.

Example 66

N-(Pyridin-3'-ylmethyl)-3,9-dioxa-6-azaunedecane-1,1'-diol (63a). This compound was obtained as a pale brown oil (1.1 g, 36%) from 65 (2.0 g, 10.4 mmol), 3-(bromomethyl)pyridine hydrobromide (2.7 g, 10.7 mmol), $K_2CO_3$ (3.1 g, 22.5 mmol) and acetone (40 mL) according to the general procedure III described above. $^1$H NMR (CDCl$_3$) δ 2.74 (t, J=5.38 Hz, 4 H), 3.52-3.61 (m, 8 H), 3.67-3.74 (m, 6 H), 4.26 (br, 2 H), 7.26-7.30 (m, 1 H), 7.75-7.79 (m, 1 H), 8.49-8.54 (m, 2 H); $^{13}$C NMR (CDCl$_3$) δ 54.4, 56.8, 61.6, 68.7, 72.5, 123.4, 133.7, 137.0, 148.7, 150.4; LRMS (ESI) m/z 285 (M$^+$+H, 97), 307 (M$^+$+Na, 100); HRMS (ESI) Calcd for $C_{14}H_{24}N_2O_4Na(M^++Na)$ 307.1634, found 307.1631.

Example 67

N-(2'-bromopyridin-4'-ylmethyl)-3,9-dioxa-6-azaunedecane-1,11-diol (63b). This compound was obtained as a pale brown oil (0.7 g, 38%) from 65 (1.0 g, 5.2 mmol), 4-(bromomethyl)-2-bromopyridine (1.3 g, 5.1 mmol), $K_2CO_3$ (0.8 g, 5.9 mmol) and acetone (40 mL) according to the general procedure III described above. $^1$H NMR (CDCl$_3$) δ 2.77 (t, J=5.14 Hz, 4 H), 3.55-3.64 (m, 8 H), 3.67-3.80 (m, 6 H), 7.28-7.47 (m, 1 H), 7.59 (s, 1 H), 8.31 (d, J=4.89 Hz, 1 H); $^{13}$C NMR (CDCl$_3$) δ 54.6, 58.1, 61.5, 68.8, 72.4, 122.8, 127.9, 142.4, 149.9, 152.1; LRMS (ESI) m/z 363 (M$^+$+H, 100), 385 (M$^+$+Na, 38); HRMS (ESI) Calcd for $C_{14}H_{24}N_2O_4Br(M^++H)$ 363.0919, found 363.0921.

Example 68

N-(2'-cyanopyridin-4'-ylmethyl)-3,9-dioxa-6-azaunedecane-1,11-diol (63c). This compound was obtained as a pale brown oil (0.9 g, 36%) from 65 (1.5 g, 7.8 mmol), 4-bromomethyl-2-pyridinecarbonitrile (1.6 g, 8.1 mmol), $K_2CO_3$ (1.2 g, 8.7 mmol) and acetone (50 mL) according to the general procedure III described above. $^1$H NMR (CDCl$_3$) δ 2.75 (t, J=5.14 Hz, 4 H), 3.50-3.61 (m, 8 H), 3.65-3.74 (m, 4 H), 3.77 (s, 2 H), 7.58-7.60 (m, 1 H), 7.82 (s, 1 H), 8.61 (d, J=5.87 Hz, 1 H); $^{13}$C NMR (CDCl$_3$) δ 54.7, 58.0, 61.6, 68.8, 72.4, 117.4, 126.8, 128.5, 133.8, 150.9, 150.9; LRMS (ESI) m/z 310 (M$^+$+H, 100), 332 (M$^+$+Na, 18); HRMS (ESI) Calcd for $C_{15}H_{24}N_3O_4(M^++H)$ 310.1767, found 310.1755.

Example 69

N-(3'-bromopyridin-4'-ylmethyl)-3,9-dioxa-6-azaunedecane-1,1'-diol (63d). This compound was obtained as a pale brown oil (1.0 g, 43%) from 65 (1.5 g, 7.8 mmol), 4-(bromomethyl)-3-bromopyridine (1.6 g, 6.4 mmol), $K_2CO_3$ (1.2 g, 8.7 mmol) and acetone (40 mL) according to the general procedure III described above. $^1$H NMR (CDCl$_3$) δ 2.75 (t, J=5.14 Hz, 4 H), 3.44-3.66 (m, 8 H), 3.72 (s, 2 H), 7.64 (d, J=4.89 Hz, 1 H), 8.40 (d, J=5.38 Hz, 1 H), 8.54 (s, 1 H); $^{13}$C NMR (CDCl$_3$) δ 54.9, 58.4, 61.5, 69.1, 72.5, 124.9, 126.7, 128.5, 148.2, 151.3; LRMS (ESI) m/z 363 (M$^+$+H, 78), 385 (M$^+$+Na, 15); HRMS (ESI) Calcd for $C_{14}H_{24}N_2O_4Br(M^++H)$ 363.0919, found 363.0930.

Example 70

N-(Pyrimidin-4'-ylmethyl)-3,9-dioxa-6-azaunedecane-1,11-diol (63e). This compound was obtained as a pale brown oil (0.44 g, 50%) from 65 (0.74 g, 3.83 mmol), 4-bromomethylpyrimidine (0.53 g, 3.07 mmol), $K_2CO_3$ (0.50 g, 3.62 mmol) and acetone (40 mL) according to the general procedure III described above. $^1$H NMR (CDCl$_3$) δ 2.74 (t, J=5.14 Hz, 4 H) 3.42-3.55 (m, 8 H), 3.56-3.70 (m, 4 H), 3.80 (s, 2 H), 7.56-7.59 (m, 1 H), 8.60 (d, J=5.38 Hz, 1 H), 9.01 (d, J=1.47 Hz, 1 H); $^{13}$C NMR (CDCl$_3$) δ 54.6, 59.9, 61.4, 68.6, 72.3, 120.4, 157.1, 158.1, 168.5; LRMS (ESI) m/z 286 (M$^+$+H, 100), 308 (M$^+$+Na, 81); HRMS (ESI) Calcd for $C_{13}H_{24}N_3O_4$ (M$^+$+H) 286.1767, found 286.1764.

Example 71

N-(Quinolin-4'-ylmethyl)-3,9-dioxa-6-azaunedecane-1,11-diol (63f). This compound was obtained as a pale brown oil (1.10 g, 46%) from 65 (1.50 g, 7.78 mmol), 4-bromomethylquinoline (1.60 g, 7.21 mmol), $K_2CO_3$ (1.20 g, 8.70 mmol) and acetone (40 mL) according to the general procedure III described above. $^1$H NMR (CDCl$_3$) δ 2.82-2.87 (m, 4 H), 3.46-3.63 (m, 4 H), 3.63-3.88 (m, 4 H), 4.13 (s, 2 H), 7.55-7.60 (m, 2 H), 7.69-7.74 (m, 1 H) 8.12 (dd, J=8.31, 1.47 Hz, 1 H), 8.26-8.30 (m, 1 H), 8.85-8.88 (m, 1 H); $^{13}$C NMR (CDCl$_3$) δ 54.8, 56.5, 61.4, 69.1, 72.4, 121.2, 123.9, 126.4, 127.4, 129.2, 129.6, 145.3, 147.9, 150.0; LRMS (ESI) m/z 335 (M$^+$+H, 100), 357 (M$^+$+Na, 45); HRMS (ESI) Calcd for $C_{18}H_{27}N_2O_4(M^++H)$ 335.1971, found 335.1965.

Example 72

N-(Quinolin-2'-ylmethyl)-3,9-dioxa-6-azaunedecane-1,1'-diol (63g). This compound was obtained as a pale brown oil (2.1 g, 59%) from 65 (2.0 g, 10.4 mmol), 2-(chloromethyl)quinoline hydrochloride (2.3 g, 10.8 mmol), $K_2CO_3$ (3.1 g, 22.5 mmol) and acetone (40 mL) according to the general procedure III described above. $^1$H NMR (CDCl$_3$) δ 2.84-2.89 (m, 4 H), 3.51-3.55 (m, 4 H), 3.59-3.65 (m, 4 H), 3.66-3.76 (m, 4 H), 4.07 (d, J=2.45 Hz, 2 H), 7.48-7.53 (m, 1 H), 7.66-7.71 (m, 2 H), 7.79 (dt, J=6.36, 1.71 Hz, 1 H), 8.07 (d, J=8.31 Hz, 1 H) 8.12-8.16 (m, 1 H); $^{13}$C NMR (CDCl$_3$) δ 54.6, 61.2, 61.6, 68.6, 72.4, 121.4, 126.2, 127.4, 127.6, 128.7, 129.5, 136.6, 147.4, 159.9; LRMS (ESI) m/z 335 (M$^+$+H, 100), 357 (M$^+$+Na, 65); HRMS (ESI) Calcd for $O_{18}H_{27}N_2O_4$ (M$^+$+H) 335.1971, found 335.1967.

General procedure IV for the synthesis of flavonoid dimers 64. To a round-bottom flask containing corresponding amino diol 63, 4'-hydroxyflavone 27a, triphenylphosphine and THF was charged with diisopropyl azodicarboxylate (DIAD) dropwise. The reaction mixture was stirred at refluxing temperature under nitrogen atmosphere for 12 hr. When TLC indicated complete consumption of starting material, the reaction mixture was cooled and filtered through a short pad of silica gel. The obtained filtrate was evaporated to give a crude reaction mixture, which was subjected to purification by flash column chromatography on silica gel with 10-30% acetone in $CH_2Cl_2$ as eluent to furnish the desired compound.

Example 73

1,13-Bis[4'-(4H-chromen-4-on-2-yl)phenyl]-7-(3-pyridylmethyl)-1,4,10,13-tetraoxa-7-azamidecane (64a). This compound was obtained as a white foam (1.20 g, 36%) from 63a (1.30 g, 4.58 mmol), 4'-hydroxyflavone 27a (2.20 g, 9.24 mmol), triphenylphosphine (2.50 g, 9.54 mmol), THF (30 mL) and DIAD (2.00 g, 9.90 mmol) according to the general procedure IV described above. $^1$H NMR (CDCl$_3$) δ 2.78-2.83 (m, 4 H), 3.62-3.66 (m, 4 H), 3.75-3.79 (m, 6 H), 4.11 (t, J=4.65 Hz, 4 H), 6.65-6.67 (m, 2 H), 6.94-6.98 (m, 4 H), 7.19 (dd, J=7.83, 4.89 Hz, 1 H), 7.32-7.36 (m, 2 H), 7.45-7.49 (m, 2 H), 7.59-7.64 (m, 2 H), 7.68 (d, J=7.82 Hz, 1 H), 7.76-7.80 (m, 4 H), 8.13-8.17 (m, 2 H), 8.45-8.47 (m, 1 H), 8.57 (s, 1 H); $^{13}$C NMR (CDCl$_3$) δ 53.8, 57.1, 67.6, 69.3, 70.2, 106.1, 115.0, 117.9, 123.2, 123.9, 124.1, 125.0, 125.5, 127.9, 133.5, 135.1, 136.4, 148.4, 150.2, 156.1, 161.6, 163.2, 178.2; LRMS (ESI) m/z 725 (M$^+$+H, 100), 747 (M$^+$+Na, 29); HRMS (ESI) Calcd for C$_{44}$H$_{41}$N$_2$O$_8$(M$^+$+H) 725.2863, found 725.2883.

Example 74

1,13-Bis[4'-(4H-chromen-4-on-2-yl)phenyl]-7-(4-(2-bromopyridyl)methyl)-1,4,10,13-tetraoxa-7-azamidecane (64b). This compound was obtained as a white foam (1.40 g, 37%) from 63b (1.70 g, 4.68 mmol), 4'-hydroxyflavone 27a (2.23 g, 9.37 mmol), triphenylphosphine (2.65 g, 10.11 mmol), THF (30 mL) and DIAD (2.02 g, 10.00 mmol) according to the general procedure IV described above. $^1$H NMR (CDCl$_3$) δ 2.77 (t, J=5.38 Hz, 4 H), 3.60 (t, J=5.38 Hz, 4 H), 3.68-3.77 (m, 6 H), 4.09 (t, J=4.65 Hz, 4 H), 6.63 (s, 2 H), 6.92 (d, J=8.80 Hz, 4 H), 7.21 (d, J=4.89 Hz, 1 H), 7.31 (td, J=7.46, 1.22 Hz, 1 H), 7.44 (d, J=8.80 Hz, 2 H), 7.52 (s, 1 H), 7.59 (ddd, J=8.56, 7.09, 1.47 Hz, 2 H), 7.73-7.78 (m, 4 H), 8.11 (dd, J=8.07, 1.71 Hz, 2 H), 8.17 (d, J=4.89 Hz, 1 H); $^{13}$C NMR (CDCl$_3$) δ 54.2, 58.1, 67.6, 69.3, 70.1, 106.0, 114.9, 117.9, 122.6, 123.8, 124.0, 125.0, 125.5, 127.5, 127.9, 133.5, 142.4, 149.8, 153.4, 156.0, 161.5, 163.1, 178.1; LRMS (ESI) m/z 803 (M$^+$+H, 68), 825 (M$^+$+Na, 91); HRMS (ESI) Calcd for C$_{44}$H$_{40}$N$_2$O$_8$Br(M$^+$+H) 803.1968, found 803.1975.

Example 75

1,13-Bis[4'-(4H-chromen-4-on-2-yl)phenyl]-7-(4-(2-cyanopyridyl)methyl)-1,4,10,13-tetraoxa-7-azamidecane (64c). This compound was obtained as a white foam (0.64 g, 30%) from 63c (0.89 g, 2.88 mmol), 4'-hydroxyflavone 27a (1.38 g, 5.80 mmol), triphenylphosphine (1.59 g, 6.07 mmol), THF (20 mL) and DIAD (1.22 g, 6.04 mmol) according to the general procedure IV described above. $^1$H NMR (CDCl$_3$) δ 2.82 (t, J=5.38 Hz, 4 H), 3.65 (t, J=5.38 Hz, 4 H), 3.79 (t, J=5.38 Hz, 4 H), 3.85 (s, 2 H), 4.12-4.16 (m, 4 H), 6.69 (s, 2 H), 6.89-6.99 (m, 4 H), 7.34-7.39 (m, 2 H), 7.48-7.52 (m, 2 H), 7.62-7.67 (m, 2H), 7.77-7.84 (m, 4 H), 8.17 (dd, J=8.07, 1.71 Hz, 2 H), 8.54 (d, J=4.89 Hz, 1H); $^{13}$C NMR (CDCl$_3$) δ 54.3, 58.1, 67.6, 69.4, 70.2, 106.1, 115.0, 117.6, 118.0, 123.9, 124.2, 125.1, 125.5, 126.5, 128.0, 128.3, 133.6, 133.8, 150.7, 152.1, 156.1, 161.5, 163.2, 178.2; LRMS (ESI) m/z 750 (M$^+$+H, 100), 772 (M$^+$+Na, 35); HRMS (ESI) Calcd for C$_{45}$H$_{40}$N$_3$O$_8$(M$^+$+H) 750.2815, found 750.2803.

Example 76

1,13-Bis[4'-(4H-chromen-4-on-2-yl)phenyl]-7-(4-(3-bromopyridyl)methyl)-1,4,10,13-tetraoxa-7-azamidecane (64d). This compound was obtained as a white foam (0.39 g, 26%) from 63d (0.67 g, 1.85 mmol), 4'-hydroxyflavone 27a (0.88 g, 3.70 mmol), triphenylphosphine (1.06 g, 4.05 mmol), THF (20 mL) and DIAD (0.82 g, 4.06 mmol) according to the general procedure IV described above. $^1$H NMR (CDCl$_3$) δ 2.84 (t, J=5.38 Hz, 4 H), 3.62 (t, J=5.62 Hz, 4 H), 3.71-3.77 (m, 4 H), 3.81 (s, 2 H), 4.04-4.10 (m, 4 H), 6.63 (s, 2 H), 6.91 (d, J=9.29 Hz, 4 H), 7.28-7.35 (m, 2 H), 7.44 (d, J=8.31 Hz, 2 H), 7.56-7.65 (m, 3 H), 7.73-7.77 (m, 4 H), 8.12 (dd, J=8.07, 1.71 Hz, 2 H), 8.37 (d, J=4.89 Hz, 1 H), 8.54 (s, 1 H); $^{13}$C NMR (CDCl$_3$) δ 54.7, 58.5, 67.6, 69.3, 70.1, 106.0, 114.9, 117.9, 121.9, 123.8, 124.0, 124.8, 125.0, 125.5, 127.9, 133.5, 148.1, 148.9, 151.3, 156.0, 161.5, 163.1, 178.1; LRMS (ESI) m/z 803 (M$^+$+H, 95), 825 (M$^+$+Na, 34); HRMS (ESI) Calcd for C$_{44}$H$_{40}$N$_2$O$_8$Br(M$^+$+H) 803.1968, found 803.1937.

Example 77

1,13-Bis[4'-(4H-chromen-4-on-2-yl)phenyl]-7-(4-pyrimidinylmethyl)-1,4,10,13-tetraoxa-7-azamidecane (64e). This compound was obtained as a white foam (0.29 g, 29%) from 63e (0.39 g, 1.37 mmol), 4'-hydroxyflavone 27a (0.65 g, 2.73 mmol), triphenylphosphine (0.74 g, 2.82 mmol), THF (20 mL) and DIAD (0.57 g, 2.82 mmol) according to the general procedure IV described above. $^1$H NMR (CDCl$_3$) δ 2.91 (t, J=5.38 Hz, 4 H), 3.66-3.87 (m, 8 H), 3.94 (s, 2 H), 4.11-4.25 (m, 4 H), 6.70-6.75 (m, 2 H), 6.97-7.06 (m, 4 H), 7.36-7.43 (m, 2 H), 7.52 (d, J=8.31 Hz, 2 H), 7.63-7.71 (m, 3 H), 7.81-7.90 (m, 4 H), 8.20 (dd, J=7.83, 1.47 Hz, 2 H), 8.59-8.62 (m, 1 H), 9.10 (s, 1 H); $^{13}$C NMR (CDCl$_3$) δ 54.7, 60.7, 67.6, 69.3, 70.1, 106.2, 115.0, 117.9, 120.0, 123.9, 124.2, 125.1, 125.6, 128.0, 133.6, 156.1, 156.9, 158.3, 161.6, 163.2, 169.7, 178.3; LRMS (ESI) m/z 726 (M$^+$+H, 100), 748 (M$^+$+Na, 28); HRMS (ESI) Calcd for C$_{43}$H$_{40}$N$_3$O$_8$(M$^+$+H) 726.2815, found 726.2789.

Example 78

1,13-Bis[4'-(4H-chromen-4-on-2-yl)phenyl]-7-(4-quinolinylmethyl)-1,4,10,13-tetraoxa-7-azamidecane (64f). This compound was obtained as a white foam (0.43 g, 26%) from 63f (0.71 g, 2.13 mmol), 4'-hydroxyflavone 27a (1.03 g, 4.33 mmol), triphenylphosphine (1.20 g, 4.58 mmol), THF (20 mL) and DIAD (0.92 g, 4.55 mmol) according to the general procedure IV described above. $^1$H NMR (CDCl$_3$) δ 2.88 (t, J=5.62 Hz, 4 H), 3.63-3.76 (m, 8 H), 4.03 (t, J=5.38 Hz, 4 H), 4.20 (s, 2 H), 6.63-6.66 (m, 2 H), 6.84-6.91 (m, 4 H), 7.28-7.34 (m, 2 H), 7.43-7.48 (m, 3 H), 7.54-7.67 (m, 4 H), 7.71-7.76 (m, 4 H), 8.06-8.09 (m, 1 H), 8.14 (dd, J=8.07, 1.71 Hz, 2 H), 8.19 (d, J=7.82 Hz, 1 H), 8.80 (d, J=4.40 Hz, 1 H); $^{13}$C NMR (CDCl$_3$) δ 54.6, 56.8, 67.6, 69.2, 70.2, 106.0, 114.9, 117.9, 121.0, 123.8, 124.0, 125.0, 125.5, 126.1, 127.4, 127.8, 129.0, 129.9, 133.5, 145.8, 148.2, 150.2, 156.0; LRMS (ESI) m/z 775 (M$^+$+H, 100), 797 (M$^+$+Na, 30); HRMS (ESI) Calcd for C$_{48}$H$_{43}$N$_2$O$_8$(M$^+$+H) 775.3019, found 775.3005.

Example 79

1,13-Bis[4'-(4H-chromen-4-on-2-yl)phenyl]-7-(2-quinolinylmethyl)-1,4,10,13-tetraoxa-7-azamidecane (64g). This compound was obtained as a white foam (0.53 g, 27%) from 63g (0.84 g, 2.51 mmol), 4'-hydroxyflavone 27a (1.21 g, 5.08 mmol), triphenylphosphine (1.37 g, 5.23 mmol), THF (30 mL) and DIAD (1.05 g, 5.20 mmol) according to the general procedure IV described above. $^1$H NMR (CDCl$_3$) δ 2.93 (t, J=5.62 Hz, 4 H), 3.68 (t, J=5.87 Hz, 4 H), 3.74-3.78 (m, 4 H), 4.06-4.11 (m, 6 H), 6.64-6.67 (m, 2 H), 6.89-6.93 (m, 4 H), 7.31-7.35 (m, 2 H), 7.43-7.47 (m, 3 H), 7.58-7.66 (m, 3 H), 7.69-7.77 (m, 6 H), 8.00-8.03 (m, 3 H), 8.15 (dd, J=7.82, 1.47 Hz, 2 H); $^{13}$C NMR (CDCl$_3$) δ 54.6, 62.2, 67.6, 69.2, 70.1, 106.0, 115.0, 117.9, 121.1, 123.8, 123.9, 125.0, 125.5, 126.1, 127.2, 127.3, 127.5, 127.8, 128.8, 129.3, 133.5, 136.2, 127.4, 156.0, 161.6, 163.2, 178.2; LRMS (ESI) m/z 775 (M$^+$+H, 100), 797 (M$^+$+Na, 32); HRMS (ESI) Calcd for C$_{48}$H$_{43}$N$_2$O$_8$ (M$^+$+H) 775.3019, found 775.3034.

Example 80

1,13-Bis[4'-(4H-chromen-4-on-2-yl)phenyl]-7-(phenyl)-1,4,10,13-tetraoxa-7-azamidecane (64h). This compound was obtained as a white foam (0.54 g, 31%) from 63h (0.67 g, 2.49 mmol), 4'-hydroxyflavone 27a (1.21 g, 5.08 mmol), triphenylphosphine (1.37 g, 5.23 mmol), THF (20 mL) and DIAD (1.05 g, 5.20 mmol) according to the general procedure IV described above. $^1$H NMR (CDCl$_3$) δ 3.65 (t, J=6.11 Hz, 4 H), 3.75 (t, J=6.11 Hz, 4 H), 3.81-3.85 (m, 4 H), 4.14-4.17 (m, 4 H), 6.70-6.77 (m, 5 H), 6.98-7.03 (m, 4 H), 7.24 (dd, J=8.80, 7.34 Hz, 2 H), 7.36-7.40 (m, 2 H), 7.45-7.58 (m, 4 H), 7.64-7.72 (m, 2 H), 7.81-7.85 (m, 4 H), 8.20 (dd, J=8.07, 1.71 Hz, 2 H); $^{13}$C NMR (CDCl$_3$) δ 51.2, 67.7, 69.0, 69.6, 106.2, 115.0, 117.9, 123.9, 124.2, 125.1, 125.6, 127.9, 128.4, 128.6, 129.4, 132.0, 133.6, 156.1, 161.6, 163.2, 178.3; LRMS (ESI) m/z 710 (M$^+$+H, 100), 732 (M$^+$+Na, 28); HRMS (ESI) Calcd for C$_{44}$H$_{40}$NO$_8$(M$^+$+H) 710.2754, found 710.2732.

Effect of Flavonoid Dimers on Reversing Paclitaxel Resistance in MDA435/LCC6MDR Cells:

With reference to Table 1, paclitaxel is over ninety-fold weaker (IC$_{50}$=152.9±3.5 nM) toward LCC6MDR cells compared to parental LCC6 cells (IC$_{50}$=1.6±0.3 nM). It has been demonstrated that paclitaxel resistance is mediated by overexpression of Pgp (Sparreboom, A. et al. *Proc Natl Acad Sci USA* 1997, 94, 2031-2035). The Relative Fold (RF) index, defined as the ratio of the IC$_{50}$ without modulator to IC$_{50}$ with modulator, serves a the measure of potency of a compound to reverse Pgp-mediated resistance to Paclitaxel.

(1) Boc-Group Protected Amine Linked Flavonoid Homodimers. With reference to Table 1 the parent compound 16a displays P-gp-modulating activity with a RF of 69.5 at 1.0 μM. Its ability to restore paclitaxel sensitivity is 24-fold higher than verapamil (RF=2.9). A methoxy group at the C3' position of the B ring (16b) considerably reduced potency with a RF of 16.8 at 1.0 whereas substitution of a methyl group at C6 position (17) or methoxy group at C5 (16d) of A ring confers improved efficacy with a RF of 139.0 and 109.2 at 1.0 μM, respectively. Thus the IC$_{50}$ of paclitaxel in LCC6MDR is restored to that of parental LCC6's cell line (Table 1). A benzyloxy group at C5 position of A ring (16e) or C3 position of C ring (16g) showed no modulating activity with a RF of 1.6 and 1.2 at 1.0 μM, respectively. Substitution of a hydroxyl group at the C5 of A ring (16f) also resulted in a very weak reversal activity with a RF of 2.9 at 1.0 μM. In terms of cytotoxicity, the unsubstituted compound (16a) and C5-methoxy substituted compound (16d) displayed killing activity to cancer lines (IC$_{50}$<8.0 μM) and normal cell L929 (IC$_{50}$<11.1 μM) (Table 1). In contrast, C6-methyl substituted compound (17) showed no cytotoxicity to all different cell lines (IC$_{50}$>100 μM).

(2) Secondary Amines 12a to 12f. Compounds (12a) and C6-methyl substituted compound (12c) consistently displayed potent reversal of resistance to paclitaxel with RF values of 139.0 at 1.0 μM. (Table 1). C3'-methoxy substituted compound 12b (RF=1.1) and C5-methoxy substituted compound 12d (RF=1.2) were inactive compared to corresponding compounds 16b (RF=16.8) and 16d (RF=109.4). In contrast, C3-benzyloxy substituted compound 12e (RF=127.6) regained reversal potency compared to the respective counterparts 16e(RF=1.2) (Table 1).

TABLE 1

Paclitaxel-resistance reversal activity and cytotoxicity of amine-linked flavonoid dimers.

| Classifications | Cpds[a] | Cytotoxicity (μM) | | | IC$_{50}$ of paclitaxel of LCC6MDR [nM] (RF) | | | |
|---|---|---|---|---|---|---|---|---|
| | | LCC6MDR | LCC6 | L929 | cpd at 1 μM | | cpd at 0.5 μM | |
| N-Boc protected amines | 16a | 6.2 ± 0.8 | 8.0 ± 2.5 | 11.1 ± 0.0 | 2.2 ± 0.5 | (69.6) | 13.8 ± 3.7 | (11.1) |
| | 16b | 6.9 ± 2.9 | 8.3 ± 1.4 | 33.3 | 9.1 ± 3.6 | (16.8) | 17.6 ± 1.8 | (8.7) |
| | 17c | >100 | >100 | >100 | 1.1 ± 0.3 | (139.2) | 16.0 ± 3.1 | (9.6) |
| | 16d | 5.4 ± 0.5 | 4.6 ± 0.2 | 5.5 ± 0.4 | 1.4 ± 0.3 | (109.4) | 10.3 ± 3.2 | (14.9) |
| | 16e | >100 | >100 | / | 131.4 ± 4.9 | (1.2) | 137.6 ± 20.6 | (1.1) |
| | 16f | >100 | >100 | >100 | 4.8 ± 1.4 | (31.9) | 13.5 ± 0.5 | (11.3) |
| Secondary amines | 12a | 2.4 ± 0.7 | 3.3 ± 1.0 | 5.9 ± 0.6 | 1.1 ± 0.1 | (139.2) | 2.1 ± 0.3 | (72.9) |
| | 12b | 23.8 ± 12.8 | 12.8 ± 1.1 | / | 134.9 | (1.1) | 194.0 ± 5.1 | (0.8) |
| | 12c | 7.0 ± 1.4 | 7.5 ± 0.9 | 6.0 ± 0.6 | 1.1 ± 0.1 | (139.2) | 11.0 ± 2.0 | (13.9) |
| | 12d | 10.2 ± 3.8 | 8.8 ± 2.7 | / | 126.6 ± 11.4 | (1.2) | 124.9 ± 10.4 | (1.2) |
| | 12e | 4.4 ± 0.1 | 4.3 ± 0.5 | 4.2 | 1.2 ± 0.1 | (127.6) | 2.8 ± 0.6 | (54.7) |
| | 12f | 3.3 ± 0.5 | 5.3 ± 1.0 | 5.7 ± 0.4 | 1.4 ± 0.1 | (109.4) | 2.1 ± 0.4 | (72.9) |
| | Verapamil | 63.9 ± 1.7 | 63.8 ± 0.1 | 89.2 ± 8.2 | 43.9 ± 5.2 | (3.5) | 76.4 ± 10.4 | (2.0) |
| | PSC833 | 14.6 ± 2.2 | 25.3 ± 4.3 | >100 | 1.8 ± 0.3 | (85.1) | / | / |
| | Cyclosporine A | 2.8 ± 0.6 | 8.3 ± 1.5 | 33.9 ± 5.2 | 2.0 ± 0.2 | (76.6) | / | / |
| | DMSO | / | / | / | 148.0 ± 13.9[b] | (1.0) | 138.4 ± 8.6[c] | (1.1) |
| | LCC6MDR | / | / | / | 153.1 ± 2.9[d] | (1.0) | / | |
| | LCC6 | / | / | / | 1.6 ± 0.3[e] | (95.7) | / | |

For determining Pgp-modulating activity, the IC$_{50}$ value was determined after exposure to a series of paclitaxel concentrations with different amine linked flavonoid dimers at 1.0 and 0.5 μM using LCC6MDR cells, as described in the experimental section. At such low modulator concentration, no observable cytotoxic effect was observed in all compounds in either LCC6 or LCC6MDR cell; Relative Fold (RF) represents fold-change in drug sensitivity. RF = (IC$_{50}$ without modulator)/(IC$_{50}$ with 1.0 or 0.5 □M modulator). Known Pgp-inhibitor verapamil was included for comparison.
N = 1-4 independent experiments and the values were presented as mean ± standard error of mean.
[a]All compounds were dissolved in DMSO for testing.
[b]0.1% of DMSO and
[c]0.05% of DMSO were solvent controls for testing the modulating activity.
[d,e]The cytotoxicity of LCC6 and LCC6MDR to paclitaxel was tested in the absence of modulators. For cytotoxicity assay, the IC$_{50}$ values of different flavonoid dimers for LCC6, LCC6MDR and L929 cell lines were determined as described in the part of materials and methods.
N = 1-3 independent experiment and the values were presented as mean ± standard error of mean.
L929: mouse fibroblast.
/: Not determined

TABLE 2

Paclitaxel-resistance reversal activity and cytotoxicity of other amine-linked flavonoid dimers.

| Classifications | Cpds[a] | Cytoxicity (µM) LCC6MDR | LCC6 | L929 | $IC_{50}$ of paclitaxel of LCC6MDR [nM] (RF) cpd at 1 µM | | cpd at 0.5 µM | |
|---|---|---|---|---|---|---|---|---|
| Amides | 23a | >100 | 78.4 ± 8.1 | / | 164.5 | (0.9) | 144.6 | (1.1) |
| | 23b | 4.6 ± 0.2 | 4.4 ± 0.0 | / | 173.1 ± 40.0 | (0.9) | 145.9 ± 13.8 | (1.0) |
| | 23d | >100 | >100 | 95.0 | 3.6 ± 0.7 | (42.5) | 20.4 ± 2.0 | (7.5) |
| | 33 | >100 | >100 | >100 | 2.1 ± 0.5 | (72.9) | 8.1 ± 1.4 | (18.9) |
| Sulfonamide | 24 | 42.6 ± 5.4 | 27.5 ± 8.4 | 13.4 ± 3.9 | 7.6 | (20.1) | 12.0 | (12.8) |
| | 25a | >100 | >100 | >100 | 7.1 ± 0.9 | (21.6) | 26.3 ± 5.6 | (5.8) |
| | 25b | >100 | >100 | / | 116.8 ± 9.5 | (1.3) | 111.2 ± 10.2 | (1.4) |
| Tertiary amines with aliphatic alkyl group R1 | 13 | 17.3 ± 3.8 | 10.3 ± 2.2 | 6.9 ± 2.0 | 1.6 ± 0.3 | (95.7) | 5.7 ± 0.2 | (26.9) |
| | 14 | 14.8 ± 5.9 | 10.7 ± 3.3 | 6.9 ± 1.4 | 4.7 ± 0.6 | (32.6) | 30.6 ± 3.8 | (5.0) |
| | 15 | 17.7 ± 3.7 | 13.5 ± 0.5 | 18.1 ± 3.4 | 3.5 ± 0.5 | (43.7) | 28.9 ± 9.5 | (5.3) |
| | 23c | 4.9 ± 0.1 | 8.6 ± 3.4 | 17.0 ± 4.3 | 1.3 ± 0.0 | (117.8) | 16.0 ± 0.8 | (9.6) |
| | 26 | >100 | >100 | 9.5 ± 0.6 | 2.7 ± 1.7 | (56.7) | 12.2 ± 8.5 | (12.5) |
| | 62 | 7.9 ± 2.7 | 10.0 ± 4.7 | 18.9 ± 2.3 | 1.3 ± 0.0 | (117.8) | 2.7 ± 0.4 | (56.7) |
| Tertiary amines with aromatic group R1: 1) have no benzylic carbon | 64h | >100 | >100 | >100 | 2.1 ± 0.3 | (72.9) | 13.2 ± 2.4 | (11.6) |
| Tertiary amines with aromatic group R1: 1) have benzylic carbon 2) aromatic ring containing No nitrogen atom 3) with No-substituted | 18 | >63 | >75 | 85.0 ± 5.0 | 1.1 ± 0.1 | (139.2) | 2.6 ± 0.6 | (58.9) |
| Tertiary amines with aromatic group R1: 1) have benzylic carbon 2) aromatic ring containing No nitrogen atom 3) with o-monosubstituted | 36 | >100 | >100 | >100 | 1.5 ± 0.2 | (102.1) | 3.5 ± 0.5 | (43.7) |
| | 46 | >100 | >100 | >100 | 1.3 ± 0.0 | (117.8) | 4.7 ± 0.8 | (32.6) |
| | 50 | >100 | >100 | >100 | 1.6 ± 0.2 | (95.7) | 12.9 ± 2.5 | (11.9) |
| Tertiary amines with aromatic group R1: 1) have benzylic carbon 2) aromatic ring containing No nitrogen atom 3) with m-monosubstituted | 37 | >100 | >100 | >87 | 1.3 ± 0.0 | (117.8) | 4.2 ± 1.0 | (36.5) |
| | 43 | >100 | >100 | >100 | 1.6 ± 0.1 | (95.7) | 6.8 ± 1.1 | (22.5) |
| | 45 | >66 | 57.7 ± 5.9 | 55.0 ± 4.4 | 1.5 ± 0.1 | (102.1) | 4.7 ± 0.5 | (32.6) |
| | 48 | >98 | >100 | >100 | 1.9 ± 0.2 | (80.6) | 7.8 ± 1.2 | (19.6) |
| | 56 | >100 | >100 | >100 | 4.2 ± 1.3 | (38.5) | 55.9 ± 11.7 | (2.7) |
| Tertiary amines with aromatic group R1: 1) have benzylic carbon 2) aromatic ring containing No nitrogen atom 3) with p-monosubstituted | 19 | >90 | 86.8 ± 1.8 | 88.0 ± 6.1 | 1.2 ± 0.1 | (127.6) | 3.5 ± 1.2 | (43.7) |
| | 20 | 64.8 ± 14.1 | 33.3 ± 10.8 | 11.4 ± 4.4 | 8.1 ± 3.5 | (18.9) | 72.3 ± 15.4 | (2.1) |
| | 34 | >83 | >100 | 19.7 ± 0.1 | 1.4 ± 0.1 | (109.4) | 4.9 ± 1.8 | (31.2) |
| | 35 | >100 | >100 | 32.7 ± 8.7 | 1.7 ± 0.4 | (90.1) | 4.1 ± 1.1 | (37.3) |
| | 42a | >100 | >91 | >100 | 1.3 ± 0.0 | (117.8) | 2.5 ± 0.6 | (61.2) |
| | 42b | >100 | >100 | >83 | 3.2 ± 0.7 | (47.8) | 40.7 ± 4.2 | (3.8) |
| | 42c | 5.9 ± 0.7 | 6.6 ± 1.0 | 4.5 ± 0.1 | 1.3 ± 0.0 | (117.8) | 1.6 ± 0.1 | (95.7) |
| | 42d | 5.3 ± 0.7 | 5.4 ± 0.6 | 4.8 ± 0.3 | 1.3 ± 0.0 | (117.8) | 1.3 ± 0.0 | (117.8) |
| | 47 | >81 | >100 | 66.4 ± 16.8 | 1.4 ± 0.1 | (109.4) | 4.9 ± 0.1 | (31.2) |
| | 49 | >100 | >100 | >78 | 1.6 ± 0.2 | (95.7) | 3.7 ± 0.6 | (41.4) |
| | 51 | >100 | >100 | 25.2 ± 12.4 | 25.9 ± 3.3 | (5.9) | 62.2 ± 10.0 | (2.6) |
| | 52 | 28.3 ± 8.2 | 21.0 ± 4.7 | 7.4 ± 1.0 | 1.3 ± 0.0 | (117.8) | 2.1 ± 0.4 | (72.9) |
| | 53 | >100 | >100 | 25.4 ± 8.1 | 2.2 ± 0.5 | (69.6) | 6.4 ± 2.1 | (23.9) |
| | 54 | >50 | >50 | >50 | 1.6 ± 0.0 | (95.7) | 3.4 ± 0.9 | (45.0) |
| | 55 | >50 | >50 | >50 | 2.1 ± 0.4 | (72.9) | 17.4 ± 2.0 | (8.8) |
| | 57 | >62 | >99 | >69 | 1.3 ± 0.1 | (117.8) | 1.5 ± 0.2 | (102.1) |
| | 61 | >100 | >91 | >100 | 5.1 ± 0.8 | (30.0) | 80.5 ± 11.8 | (1.9) |
| Tertiary amines with aromatic group R1: 1) have benzylic carbon 2) aromatic ring containing No nitrogen atom 3) with Di-substituted | 38 | 33.6 ± 4.3 | 32.5 ± 11.0 | 42.2 ± 2.1 | 1.4 ± 0.0 | (109.4) | 3.1 ± 0.6 | (49.3) |
| | 40 | >100 | >100 | >100 | 1.3 ± 0.0 | (117.8) | 4.7 ± 0.4 | (32.6) |
| | 41 | >100 | >100 | >100 | 1.7 ± 0.3 | (90.1) | 4.5 ± 1.1 | (34.0) |
| | 42e | >100 | >100 | >100 | 1.3 ± 0.0 | (117.8) | 4.2 ± 0.9 | (31.2) |
| | 44 | >100 | >100 | >100 | 3.0 ± 1.3 | (51.0) | 8.0 ± 1.6 | (19.1) |
| | 58 | 8.9 ± 3.3 | 4.8 ± 0.4 | 5.1 ± 0.3 | 1.3 ± 0.0 | (117.8) | 1.6 ± 0.3 | (95.7) |
| | 59 | >100 | >100 | >100 | 1.9 ± 0.2 | (80.6) | 70.3 ± 10.0 | (2.2) |
| Tertiary amines with aromatic group R1: 1) have benzylic carbon 2) aromatic ring containing No nitrogen atom 3) with Tri-substituted | 39 | >100 | >75 | >100 | 1.9 ± 0.3 | (80.6) | 46.8 ± 23.2 | (3.3) |
| | 42f | >100 | >100 | >100 | 1.9 ± 0.5 | (80.6) | 32.2 ± 12.6 | (4.8) |
| Tertiary amines with aromatic group R1: 1) have benzylic carbon 2) aromatic ring containing nitrogen atom | 21 | >100 | >100 | 26.4 ± 2.7 | 5.5 ± 1.4 | (27.8) | 22.3 ± 0.2 | (6.9) |
| | 22 | 29.7 ± 16.4 | 10.0 ± 1.2 | 10.0 ± 2.8 | 1.6 ± 0.1 | (95.7) | 9.7 ± 0.1 | (15.8) |
| | 60 | >100 | >100 | >70 | 1.3 ± 0.0 | (117.8) | 7.0 ± 1.1 | (21.9) |
| | 64a | 4.7 ± 0.2 | 5.7 ± 1.4 | 2.3 ± 0.2 | 3.3 ± 0.6 | (46.4) | 18.0 ± 2.3 | (8.5) |
| | 64b | >100 | >100 | >100 | 2.0 ± 0.2 | (76.6) | 18.2 ± 3.3 | (8.4) |
| | 64c | >100 | >100 | >50 | 2.3 ± 0.4 | (66.6) | 7.9 ± 1.6 | (19.4) |
| | 64d | >100 | >100 | >50 | 2.5 ± 0.4 | (61.2) | 14.5 ± 2.6 | (10.6) |
| | 64e | >50 | >50 | >50 | 2.5 ± 0.3 | (61.2) | 18.5 ± 1.0 | (8.3) |
| | 64f | >100 | >100 | >100 | 2.2 ± 0.3 | (69.6) | 9.6 ± 1.6 | (15.9) |
| | 64g | >100 | >100 | 8.5 ± 2.3 | 1.5 ± 0.1 | (102.1) | 2.3 ± 0.3 | (66.6) |

For determining Pgp-modulating activity, the $IC_{50}$ value was determined after exposure to a series of paclitaxel concentrations with different amine linked flavonoid dimers at 1.0 and 0.5 µM using LCC6MDR cells, as described in the experimental section. RF value was determined and the $IC_{50}$ values were presented as mean ± standard error of mean.
N = 1-4 independent experiments.
For cytotoxicity assay, the $IC_{50}$ values of different flavonoid dimers for LCC6, LCC6MDR and L929 cell lines were determined as described in the part of materials and methods.
N = 1-3 independent experiment and the values were presented as mean ± standard error of mean.
L929: mouse fibroblast.
/: Not determined.

(3) Tertiary Amines. With respect to Table 2, the amino group on the linker is substituted with different groups. Generally the Pgp modulating activity varies significantly among the compounds of this series. Some amino substituents do not confer enhancement of P-gp-mediated resistance reversal potency including N-Succinyl (23a, RF=0.9), N-Danysl (25b, RF=1.3) and N-Alanyl (23b, RF=0.9) at 1.0 µM. The N-substitutions that imparted moderate activity at 1.0 µM with $IC_{50}$ values of paclitaxel ranged from 2.1 to 7.6 nM included ethyl propanoate group (15, RF=43.7), hydroxyethyl group (14, RF=32.5), pyridine ring with nitrogen atom at position 4 (21, RF=27.8), mesylate group (24, RF=20.1), tosylate group (25a, RF=21.6), propyl phenyl group (26, RF=56.7), 4-methoxycarbonyllbenzyl group (20, RF=18.9), benzoyl group (23d, RF=42.5) and tert-butylacetyl group (33, RF=72.9). The groups that gave the highest activity with $IC_{50}$ value of paclitaxel lower than 2.0 nM at 1.0 µM modulator included benzyl group (18, RF=139.2), 4-nitrobenzyl group (19, RF=127.6), 4-fluorobenzyl group (34, RF=109.4), 4-trifluoromethylbenzyl group (35, RF=90.1), 2-fluorobenzyl group (36, RF=102.1), 3-fluorobenzyl group (37, RF=117.8), 3,4-difluorobenzyl group (38, RF=109.4), 3,4,5-trifluorobenzyl group (39, RF=80.6), ethyl group (13, RF=95.7), 2-(phthalimido)-ethyl group (23c, RF=117.8) and pyridine ring with nitrogen atom at position 2 (22, RF=95.7). In addition to modulating the activity of paclitaxel, the amine linker also plays an important role in determining cytotoxicity. N-Alkyl amine substituted flavonoid dimers were found to induce toxic effect to cancer cells and L929 cells. These included the ethyl propanoate group (15, $IC_{50}$ ranged from 13.5 to 17.7 µM), hydroxyethyl group (14, $IC_{50}$ ranged from 6.9 to 14.8 µM) and ethyl group (13, $IC_{50}$ ranged from 6.9 to 17.3 µM). Similarly, amine linked dimers with the propyl phenyl group (26, $IC_{50}$ for L929=9.5 µM), pyridine ring with nitrogen atom at position 2 (22, $IC_{50}$ for L929=10.0 µM), 2-(phthalimido)-ethyl group (23c, $IC_{50}$ ranged from 4.9 to 8.6 µM) are quite cytotoxic although they possessed marked reversal potency. Comparatively, benzyl group was demonstrated to be a desirable substitution for making potent Pgp inhibitor while remaining relatively non-toxic to L929 cells. Most of them were shown to be non-cytotoxic and to completely reverse 95.6-fold resistance of LCC6MDR to paclitaxel at 1.0 µM. These benzyl substituted compounds included 18 ($IC_{50}$>63 µM, RF=139.2 at 1.0 µM and RF=58.9 at 0.5 µM), 19 ($IC_{50}$>90.0 µM, RF=127.6 at 1.0 µM and RF=43.7 at 0.5 µM), 36 ($IC_{50}$>100 µM, RF=102.1 at 1.0 µM and RF=43.7 at 0.5 µM), 37 ($IC_{50}$>100 µM, RF=117.8 at 1.0 µM and RF=36.5 at 0.5 µM) and 39 ($IC_{50}$>100 µM, RF=80.6 at 1.0 µM and RF=3.3 at 0.5 µM). However, an addition of a fluorine atom at the position 4 of benzyl group (34, $IC_{50}$ for L929=19.7 µM and 35, $IC_{50}$ for L929=32.7 µM) leads to an increase of cytotoxicity compared to the parent compound 18 ($IC_{50}$ for L929=85.0 µM), 2-fluorobenzyl substituted compound 36 ($IC_{50}$ for L929>100 µM) and 3-fluorobenzyl substituted compound 37 ($IC_{50}$ for L929>87 µM). A number of compounds showed low cytotoxicity to normal L929 cell and high RF in reversing cancer drug resistance. Their EC50 values and therapeutic indexes were determined and compiled in Table 3. Compounds 18, 42a and 57 exhibited the highest therapeutic indexes among this group.

TABLE 3

$EC_{50}$ values and therapeutic indexes of flavonoid dimers for lowering anticancer drug resistance in LCC6?MDR cells.

| | $EC_{50}$ of compounds for reversing anticancer drug resistance (nM) | | | | | | |
|---|---|---|---|---|---|---|---|
| Compounds | Paclitaxel | Vinblasinte | Vincristine | Doxorubicin | Daunorubicin | Mitoxantrone | Therapeutic index |
| 12a | 305 ± 35 | / | / | / | / | / | 19.3 |
| 13 | 200 ± 0 | / | / | / | / | / | 34.5 |
| 16a | 320 ± 40 | / | / | / | / | / | 34.7 |
| 18 | 148 ± 18 | 173 ± 27 | 179 ± 32 | 131 ± 13 | 95 ± 25 | 90 ± 20 | 574.3 |
| 19 | 189 ± 1 | / | / | / | / | / | 465.6 |
| 26 | 250 | / | / | / | / | / | 38.0 |
| 34 | 255 ± 5 | / | / | / | / | / | 77.3 |
| 35 | 150 | / | / | / | / | / | 218.0 |
| 36 | 179 ± 44 | / | / | / | / | / | >558.7 |
| 37 | 258 ± 103 | / | / | / | / | / | >337.2 |
| 40 | 246 ± 66 | / | / | / | / | / | >406.5 |
| 41 | 237 ± 91 | / | / | / | / | / | >421.9 |
| 42a | 104 ± 7 | 94 ± 13 | 98 ± 5 | 63 ± 8 | 61 ± 6 | 96 ± 27 | >961.5 |
| 42c | 140 ± 12 | / | / | / | / | / | 32.1 |
| 42d | 141 ± 9 | / | / | / | / | / | 34.0 |
| 42e | 204 ± 20 | / | / | / | / | / | >490.2 |
| 49 | 177 ± 14 | / | / | / | / | / | >440.7 |
| 54 | 188 | / | / | / | / | / | 266.0 |
| 55 | 244 | / | / | / | / | / | 204.9 |
| 57 | 72 ± 21 | 38 ± 10 | 83 ± 12 | 94 ± 1 | 76 ± 14 | 65 ± 19 | >958.3 |
| 58 | 92 ± 11 | / | / | / | / | / | 55.4 |
| 62 | 132 ± 7 | / | / | / | / | / | 143.2 |
| Verapamil | 428 ± 40 | 500 ± 22 | 385 ± 35 | 245 ± 23 | / | / | 208.4 |
| PSC833 | 2.3 ± 1 | / | / | 1.9 ± 0 | / | / | >43478.3 |
| Cyclosporine A | 32 ± 1 | / | / | 43 ± 4 | / | / | 1059.4 |

$EC_{50}$ values were presented as mean ± standard error of mean.
N = 1-7 independent experiments.
/: not determined.
Therapeutic index = $IC_{50}$ of compounds for L929/$EC_{50}$ of compounds for lowering paclitaxel drug resistance.

Effect of Compound 18 on Intracellular Doxorubicin Accumulation in MDA435/LCC6MDR Cells. FIG. 1A shows that the level of doxorubicin accumulation in parental LCC6 cells is about 2.9-fold (P<0.001) higher than that of LCC6MDR cells. Treatment of parental LCC6 cells which do not overexpress Pgp with 1 µM of compound 18 or verapamil does not increase intracellular doxorubicin accumulation. In contrast, treatment of Pgp-overexpressed LCC6MDR cells with 1 µM of compound 18 or verapamil significantly resulted in 2.7-fold (P<0.001) and 2.3-fold (P<0.005) increase in intracellular doxorubicin accumulation.

FIGS. 1B and 1C show that doxorubicin accumulation is dose-dependent with respect to 18 and verapamil. Flavonoid dimer 18 at 0.5 μM was sufficient to restore accumulation of doxorubicin in LCC6MDR to levels of parental LCC6 cells (FIG. 1B). The concentration of verapamil required to restore doxorubicin accumulation is in the order of 8 μM (FIG. 1C). Compound 18 is therefore roughly 16-fold more active than verapamil in inhibiting the doxorubicin transport activity of Pgp.

Figure 2:
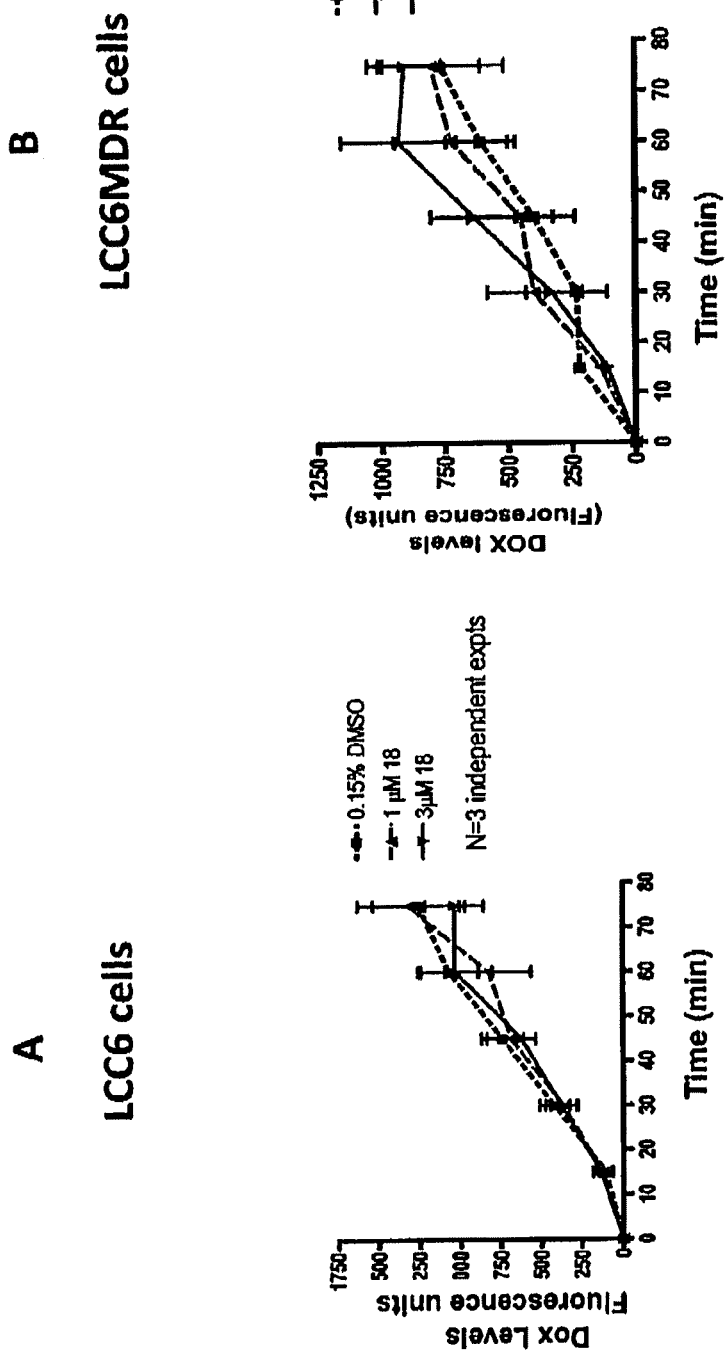
FIG. 2 shows the effect of compound 18 on Doxorubicin influx in LCC6 cells (A) compared to LCC6MDR cells (B)

Effect of Compound 18 on Doxorubicin Influx and Efflux of MDA435/LCC6MDR Cells. Experiments were performed to determine whether the increased accumulation of doxorubicin in LCC6MDR cells caused by 18 is due to potentiation of doxorubicin influx or inhibition of efflux. For influx experiments, both LCC6 and LCC6MDR cells were co-incubated with doxorubicin and compound 18 (0 μM, 1 μM or 3 μM) and intracellular doxorubicin concentration was determined after 0, 15, 30, 45, 60 and 75 minutes, in each case. In the absence of 18, it was found that the intracellular doxorubicin level increased in the range of 0-1255 and 0-764 fluorescence units (FU) in LCC6 and LCC6MDR after 75 min, respectively (FIGS. 2A and 2B). In the presence of 1 or 3 μM of 18, doxorubicin influx rate remained unchanged in both LCC6 (0-1320 FU at 1 μM and 0-1035 FU at 3 μM) and LCC6MDR (0-803 FU at 1 μM and 0-909 FU at 3 μM) cells, indicating that 18 has no effect on doxorubicin influx.

Figure 3:
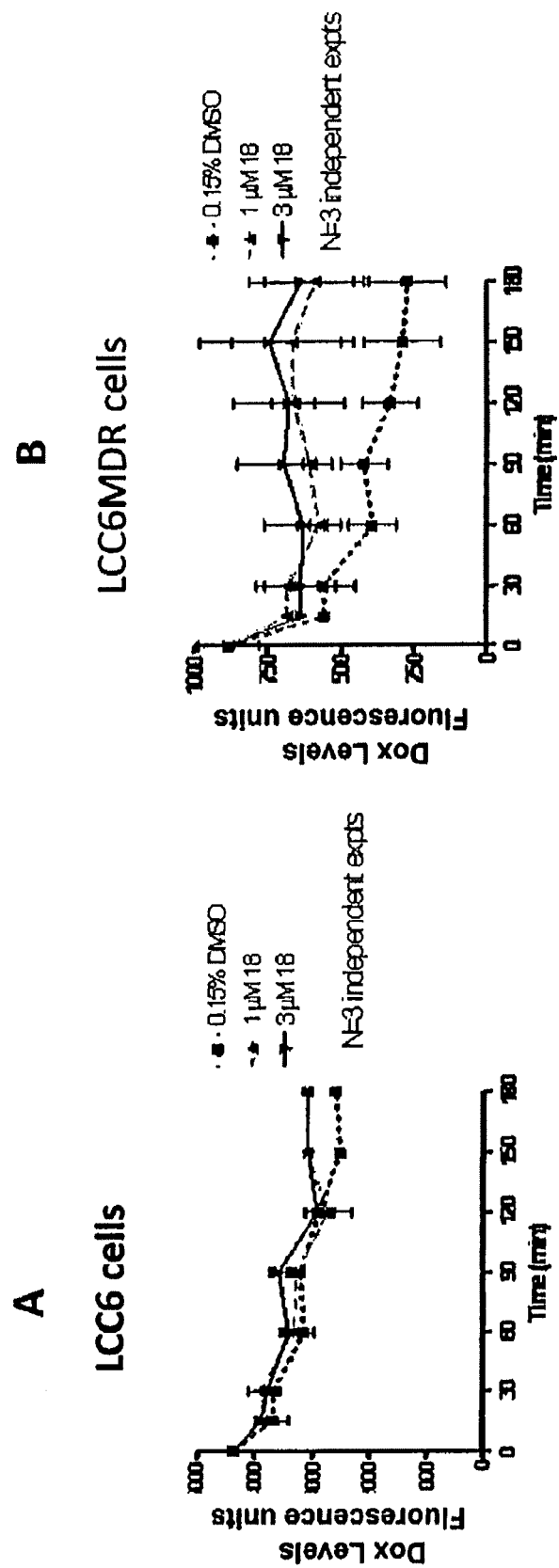
FIG. 3 shows the effect of compound 18 on Doxorubicin efflux in LCC6 cells (A) compared to LCC6MDR cells (B)

In the efflux experiments, both LCC6 and LCC6MDR were first pre-loaded with doxorubicin for 2 hrs, washed and the remaining doxorubicin was measured after 0, 15, 30, 60, 90, 120, 150 and 180 min. At 0 μM of 18, the doxorubicin level of parental LCC6 cells gradually diminished from 4376 FU to 2601 FU after 3 hrs (FIG. 3A), indicating that there was about 60% of doxorubicin remaining. In contrast at 0 μM of 18, the doxorubicin level of LCC6MDR cells was dramatically reduced from 883 FU to 273 FU after 3 hrs (FIG. 3B), indicating that there was about 30% of doxorubicin remaining. Thus efflux rate of LCC6MDR is higher than LCC6. At 1DM or 3 μM of 18, the doxorubicin efflux rate was unaltered in the wild type LCC6 cells. After 3 hrs, the intracellular doxorubicin levels of LCC cells at 1 μM (3122 FU, 71% of doxorubicin remained) and 3 μM (3103 FU, 71% of doxorubicin remained) were very close to that at 0 μM (2601 FU, 60% of doxorubicin remained), respectively (FIG. 3A). On the contrary, at 1 or 3 μM of 18, the doxorubicin efflux rate was markedly decreased in LCC6MDR cells. After 3 hrs, the intracellular doxorubicin level of LCC6MDR cells was about 2.2-fold at 1 μM (591 FU, 67% of doxorubicin remained) and 2.3-fold at 3 μM (640 FU, 72% of doxorubicin remained) higher than that at 0 μM (273 FU, 30% of doxorubicin remained), respectively (FIG. 3B).

Anti-Promastigotes Activity of Flavonoid Dimers. With reference to Table 4, compounds 12-26 are characterized by a fixed length linker having 4 EG units containing a tertiary amino group. Surprisingly, the anti-promastigote activity of the compounds was found to be greatly improved when they are compared with compounds of similar structure but with the amino group replaced by an oxygen atom. The parent compound 12 displayed killing activity to both parasites and macrophage Raw264.7 cells with $IC_{50}$ value lower than 4 μM (Table 5). Addition of ethyl group (13), hydroxyethyl group (14) or ethyl propanoate group (15) on the amino PEG linker did not diminish cytotoxicity toward macrophage Raw264.7 cells ($IC_{50}$ for Raw264.7=6.4 to 16.0 μM).

Bulky N-substitution (16-26) trends toward lower cytotoxic effects on macrophage Raw264.7 cells with $IC_{50}$ values ranged from 45.7 μM to greater than 100 μM.

Compound 21, with a nitrogen atom on position 4 of the pyridine ring, exhibited the lowest $IC_{50}$ values ($IC_{50}$=0.13 to 0.35 μM) among the compounds and was not cytotoxic to the Raw264.7 cells ($IC_{50}$>100 μM). Compound 22, the nitrogen atom on position 2 of the pyridine ring, displayed about 10-fold lower leishmanicidal activity ($IC_{50}$=1.8 to 2.4 μM) than the compound 21.

With reference to Table 4, among the compounds devoid of cytotoxicity upon macrophage Raw264.7 cells at 100 μM, compound 21 exhibited the strongest antileishmanial activity with $IC_{50}$ values ranging from 0.13 μM to 0.35 μM against several different species of *Leishmania*, particularly sodium stibogluconate-resistant Ld39 and pentamidine-resistant LdAG83PentR50. With reference to Table 5, the activity and cytotoxicity of compound 21 is compared to commonly clinically used antileishmanials. The first-line antileishmanial, sodium stibogluconate, was the weakest compound for killing promastigotes with an $IC_{50}$ value greater than 1000 μM. Ld39 is 2.7-fold more resistant to sodium stibogluconate than the wild type LdAG83 (Wong, I. L. et al. *Antimicrob Agents Chemother* 2007, 51, 930-940). Among the second-line anti-leishmaials, pentamidine and miltefosine display moderate anti-promastigote activity with $IC_{50}$ values ranging from 5.3 to 74.7 μM and 4.3 to 17.3 μM, respectively. Both also exert moderate cytotoxicity for macrophage Raw264.7 cell line with $IC_{50}$ values of 30.0 μM and 20.0 μM, respectively. The pentamidine-selected strain, LdAG83-PentR50, is about 4.6-fold more resistant to pentamidine than wild type LdAG83. While the aminoglycoside paromomycin, exhibits no cytotoxicity upon Raw 264.7 ($IC_{50}$>100 μM), it also displays poorer leishmanicidial activity with $IC_{50}$ values ranging from 24.5 to 94.5 μM.

TABLE 4

Anti-promastigotes activity of N-substituted flavonoid dimers.

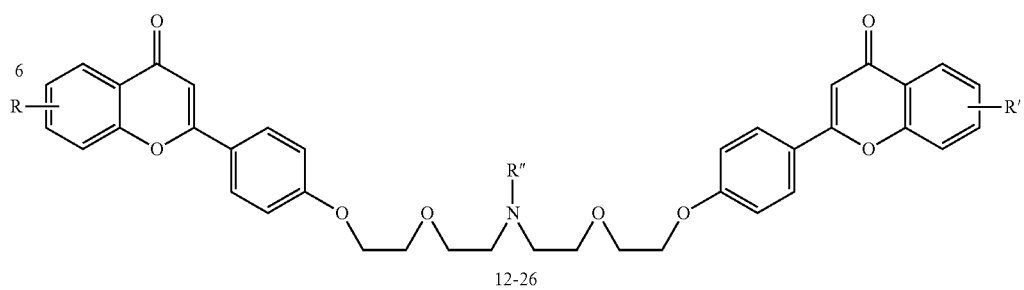

12-26

Anti-promastigotes activity ($IC_{50}$, μM)

| Cpd | R | R' | R'' | LdAG83 | Ld39 | LdAG83PentR50 | Lm50122 | Raw264.7 |
|---|---|---|---|---|---|---|---|---|
| 12 | H | H | H | 3.3 | 2.3 | 1.1 | ND | 2.1 ± 0.9 |
| 13 | H | H | $CH_2CH_3$ | 3.2 ± 0.8 | 5.5 ± 1.1 | ND | ND | 8.3 ± 1.0 |

TABLE 4-continued

| | | | | | | | | |
|---|---|---|---|---|---|---|---|---|
| 14 | H | H | $CH_2CH_2OH$ | 3.2 ± 1.1 | 7.2 ± 2.2 | ND | ND | 6.4 ± 1.5 |
| 15 | H | H | $(CH_2)_2CO_2CH_2CH_3$ | 3.8 ± 0.8 | 6.6 ± 0.2 | ND | ND | 16.0 ± 6.2 |
| 16 | H | H | $C(=O)OC(CH_3)_3$ | 3.2 | 1.6 | 1.1 | ND | >100.0 |
| 17 | 6-Me | 6-Me | $C(=O)OC(CH_3)_3$ | 21.0 | 100.0 | ND | >100.0 | >100.0 |
| 18 | H | H | $CH_2C_6H_5$ | 8.4 ± 6.1 | 12.3 ± 6.0 | ND | ND | >79.0 |
| 19 | H | H | $CH_2(4NO_2-C_6H_4)$ | >100.0 | >100.0 | ND | >100.0 | 70.3 ± 9.7 |
| 20 | H | H | $CH_2(4CO_2CH_3-C_6H_4)$ | >100.0 | >100.0 | ND | >100.0 | 45.7 ± 19.1 |
| 21 | H | H | $CH_2(4-C_5H_4N)$ | 0.18 ± 0.02 | 0.19 ± 0.03 | 0.13 ± 0.04 | 0.35 ± 0.07 | >100.0 |
| 22 | H | H | $CH_2(2-C_5H_4N)$ | 2.3 ± 0.8 | 2.4 ± 1.0 | ND | 1.8 ± 0.6 | 53.0 ± 12.7 |
| 23 | H | H | $C=O(CH_2)_2CO_2H$ | >100.0 | >100.0 | 27.0 | ND | 65.0 |
| 24 | H | H | $SO_2CH_3$ | 0.5 | 1.5 | ND | ND | 96.0 ± 4.0 |
| 25 | H | H | $SO_2(4CH_3-C_6H_4)$ | 100.0 | >100.0 | ND | ND | >100.0 |
| 26 | H | H | $(CH_2)_3C_6H_5$ | 8.9 | 18.4 | ND | ND | 85.0 |

The $IC_{50}$ value is a parameter of antileishmanial activity. The *Leishmania* promastigotes were treated with various concentrations of the test compound and incubated for 3 days at 27° C. The % of survivors was determined by colorimetric MTS assay as described in Materials and Methods. The values are mean ± standard error of mean. N = 1-4 independent experiments. The susceptibility of mouse macrophage Raw264.7 cell to the compounds in Table 3 was determined in order to assess the selective cytotoxicity of these dimers.
ND = not determined Amphotericin B is the most potent drug against promastigotes with $IC_{50}$ values ranging between 0.051 to 0.34 µM. It is also the most toxic compound for the Raw264.7 with an $IC_{50}$ value of 12.0 µM. Compound 21 is superior to most of the clinically used antileishmanials and slightly less potent than amphotericin B in killing promastigotes. Compound 21 exhibits 2-fold lower anti *L. donovani* promastigote activity than amphotericin B. There was no difference between 21 and amphotericin in killing *L. major* promastigotes Importantly, compound 21 displayed no cytotoxicity for the macrophage cell Raw264.7.

TABLE 5

Anti-promastigotes activity of common antileishmanials compared to compound 21

| | Anti-promastigotes activity ($IC_{50}$, µM) | | | | |
|---|---|---|---|---|---|
| Compounds | LdAG83 | Ld39 | LdAG83PentR50 | Lm50122 | Raw264.7 |
| Sodium stibogluconate | 2659[a] | 7090[a] | ND | 1050 ± 500 | >11000 |
| Pentamidine | 16.2[b] | 5.3 ± 0.8 | 74.7[b] | 7.7 ± 1.0 | 30.0 ± 5.0 |
| Amphotericin B | 0.090 ± 0.02 | 0.095 ± 0.02 | 0.051 ± 0.00 | 0.34 ± 0.06 | 12.0 ± 2.5 |
| Miltefosine | 4.3 ± 1.1 | 17.3 ± 2.1 | 9.3 ± 2.4 | 9.8 ± 2.3 | 20.0 ± 3.6 |
| Paromomycin | 62.6 ± 9.5 | 24.5 ± 2.4 | 85.5 ± 13.5 | 94.5 ± 5.5 | >100.0 |
| 21 | 0.18 ± 0.02 | 0.19 ± 0.03 | 0.13 ± 0.04 | 0.35 ± 0.07 | >100.0 |

With reference to Table 6, the cytotoxicity against the mouse primary peritoneal elicited macrophage (PEM) of compound 21 was compared with currently used antileishmanials in order to determine the therapeutic index. A safe antileishmanial should be potent against intracellular *Leishmania* parasite and induce no cytotoxicity for its mammalian host macrophage cells. A therapeutic index lower than 10 would indicate probable non-selective cytotoxicity for a compound. Amphotericin B is the most toxic among the clinically used compounds with an $IC_{50}$ of 7.4 µM (Table 6). Pentamidine induced a moderate cytotoxicity for PEM with an $IC_{50}$ of 30.4 µM. Other compounds generally displayed less or no toxicity for the PEM with $IC_{50}$ values greater than 75.3 µM.

In terms of therapeutic index ($IC_{50}$ against PEM/$IC_{50}$ against promastigotes), compound 21 is the highest among all compounds shown in Table 6, ranging from >251 to >677 for different strains of promastigotes. This is followed by amphotericin B which has a thereapeutic index ranging from 22 to 145. Other compounds displayed a relatively low therapeutic index ranging from 0.4 to 17.5.

TABLE 6

Anti-promastigotes activity and therapeutic index of compound

| | | Therapeutic index relative to PEM | | | |
|---|---|---|---|---|---|
| Compounds | PEM ($IC_{50}$, µM) | LdAG83 | Ld39 | LdAG83PentR50 | Lm50122 |
| Sodium stibogluconate | >11000 | >4.1 | >1.6 | ND | >10.5 |
| Pentamdine | 30.4 ± 10.5 | 1.9 | 5.7 | 0.4 | 3.9 |
| Amphotericin B | 7.4 ± 0.4 | 82.2 | 77.9 | 145.1 | 21.8 |
| Miltefosine | 75.3 ± 9.4 | 17.5 | 4.4 | 8.1 | 7.7 |
| Paromomycin | >100.0 | >1.6 | >4.1 | >1.2 | >1.1 |
| Luteolin | 77.7 ± 7.7 | 0.7 | 0.9 | 0.9 | 0.8 |
| Quercetin | >100.0 | >1.0 | >1.0 | >1.4 | >1.0 |
| 21 | >88.0 | >488.9 | >463.2 | >676.9 | >251.4 |

In vitro Anti-amastigote Activity of Compound 21 and its Therapeutic Index

Figure 4:
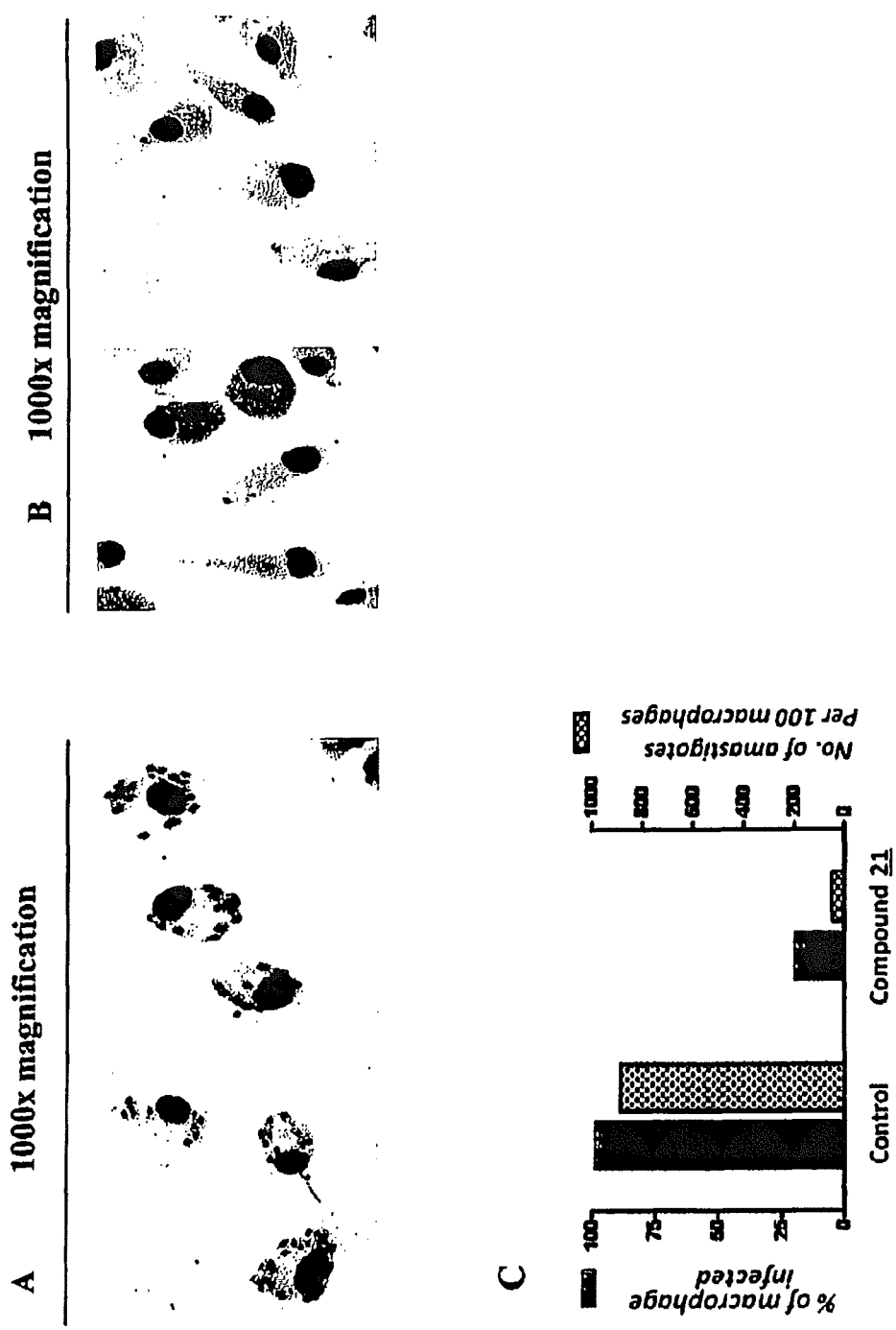
FIG. 4 shows the anti-amastigotes activity of solvent control (A) or compound 21 (B) against sodium stibogluconate-resistant *L. donovani* Ld39 amastigotes grown in mouse peritoneal elicited macrophage (PEM) cells. Extent of infection as enumerated by percentage of infection or number of amastigotes per 100 macrophages is shown in (C).

Mouse primary peritoneal elicited macrophage cells were infected with sodium stibogluconate-resistant Ld39 promastigotes, allowed 24 hours for transformation into amastigotes, and were then further incubated with different concentrations of compound 21 or the current clinically used antileishmanials for 3 days. The % of infected macrophage and the number of amastigotes per 100 macrophages were counted by staining with Giemsa. FIG. 4 shows pronounced anti-amastigote activity for compound 21. In controls, numerous dark-blue dots representing amastigotes were observed in host macrophages (FIG. 4A). Only a few amastigotes were noted in the macrophages after addition of 5 μM of compound 21 (FIG. 4B). FIG. 4C shows that the % of macrophage infected was decreased from 100% to 20% and the number of amastigotes per 100 macrophages also dropped dramatically from 887 to 48 in the presence of 5 μM of compound 21 compared to solvent control.

Table 7 list the cytotoxicity of different antileishmanial compounds on PEM and Ld39 amastigotes. Amphotericin B is the most potent one against amastigotes with an $IC_{50}$ value of 0.062 μM, followed by compound 21 with an $IC_{50}$ value of 0.63 μM. Although amphotericin B exhibited the strongest anti-amastigote activity, it also displayed the highest toxicity against PEM cells ($IC_{50}$=7.4 μM). Compound 21 was non cytotoxic to

TABLE 7

Anti-amastigotes activity and therapeutic index of compound 21 compared to known compounds.

| Compounds | PEM ($IC_{50}$, mM) | Ld39 ($IC_{50}$, mM) | Therapeutic index relative to PEM |
|---|---|---|---|
| Sodium stibogluconate | >11000 | 675 ± 75 | >16.3 |
| Pentamidine | 30.4 ± 10.5 | >30.0 | >1.0 |
| Amphotericin B | 7.4 ± 0.4 | 0.062 ± 0.00 | 119.4 |
| Miltefosine | 75.3 ± 9.4 | 16.0 ± 6.4 | 4.7 |
| Paromomycin | >100.0 | 41.0 | >2.4 |
| Luteolin | 77.7 ± 7.7 | 7.7 ± 3.6 | 10.1 |
| Quercetin | >100.0 | 6.0 ± 1.1 | >16.7 |
| 21 | >88.0 | 0.63 ± 0.12 | >139.7 |

PEM cells ($IC_{50}$ > 88 μM). In terms of therapeutic index, compound 21 has the highest therapeutic index (>139.7), followed by amphotericin B (119.4), suggesting that both possess very high selective cytotoxicity for Leishmania amastigotes. Both current antileishmanials (sodium stibogluncanate, pentamidine, miltefosine and paromomycin) or flavonoids (luteolin and quercetin) have lower therapeutic index ranging from >2.4 to >16.7, which are significantly lower than that of compound 21 or amphotericin B.

While specific embodiments of the present invention have been described in the examples, it is apparent that modifications and adaptations of the present invention will occur to those skilled in the art. The embodiments of the present invention are not intended to be restricted by the examples. It is to be expressly understood that such modifications and adaptations which will occur to those skilled in the art are within the scope of the present invention, as set forth in the following claims. For instance, features illustrated or described as part of one embodiment can be used in another embodiment, to yield a still further embodiment. Thus, it is intended that the present invention cover such modifications and variations as come within the scope of the claims and their equivalents.

The invention claimed is:
1. A compound of formula II:

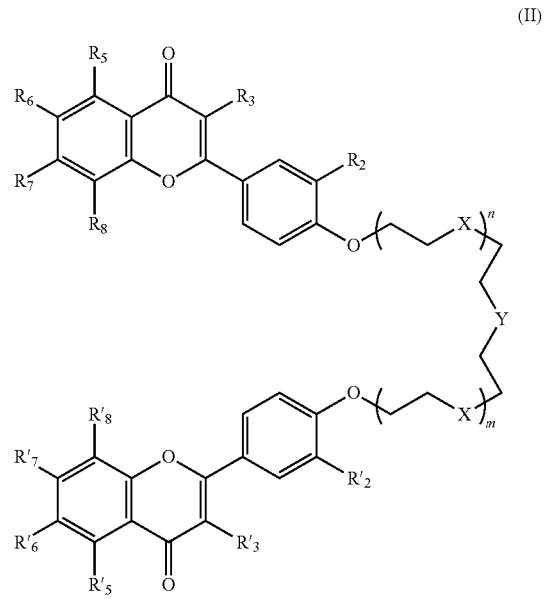

(II)

or a pharmaceutically acceptable salt or solvate thereof, wherein
Y is N—$R_1$
$R_1$ is independently selected from the group consisting of H, alkyl, alkenyl, alkoxy, cycloalkyl, heterocycloalkyl, cycloalkenyl, heterocycloalkenyl, aryl, heteroaryl, —$(CH_2)_q$-aryl, —$(CH_2)_q$-heteroaryl, —$(CH_2)_q$-cycloalkyl, —$(CH_2)_q$-cycloalkenyl, —$(CH_2)_q$-heterocycloalkyl, —$(CH_2)_q$-heterocycloalkenyl, —C(O)-alkyl, —C(O)-aryl, —C(O)-heteroaryl, —C(O)-cycloalkyl, —C(O)-cycloalkenyl, —C(O)-heterocycloalkyl, —C(O)-heterocycloalkenyl, —C(O)O-alkyl, —C(O)O-aryl, —C(O)O-heteroaryl, —C(O)O-cycloalkyl, —C(O)O-cycloalkenyl, —C(O)O-heterocycloalkyl, —C(O)O-heterocycloalkenyl, —S-alkyl, —S-aryl, —S-heteroaryl, —S-cycloalkyl, —S-heterocycloalkyl, —SO-alkyl, —SO-aryl, —SO-heteroaryl, —SO-cycloalkyl, —SO-heterocycloalkyl, —$SO_2$-alkyl, —$SO_2$-aryl, —$SO_2$-heteroaryl, —$SO_2$-cycloalkyl, or —$SO_2$-heterocycloalkyl, any of which may be optionally substituted;
$R_2$ and $R'_2$ are each independently selected from the group consisting of H, OH, halogen, alkyl, alkenyl, alkoxy, aryloxy, cycloalkyl, heterocycloalkyl, cycloalkenyl, heterocycloalkenyl, aryl, —O—$(CH_2)_q$-aryl, —$(CH_2)_q$-cycloalkyl, —$(CH_2)_q$-heterocycloalkyl, —$(CH_2)_q$-aryl, —$(CH_2)_q$-heteroaryl, —C(O)-alkyl, —C(O)-aryl, —C(O)-heteroaryl, —C(O)-cycloalkyl, —C(O)-heterocycloalkyl, —C(O)O-alkyl, —C(O)O-aryl, —C(O)O-heteroaryl, —C(O)O-cycloalkyl, or —C(O)O-heterocycloalkyl, any of which may be optionally substituted;
n, and m are independently an integer from 1 to 6;
X is selected from $CH_2$, O or N—$R_1$;
$R_3$; $R'_3$; $R_5$; $R'_5$; $R_6$; $R'_6$; $R_7$; $R'_7$; $R_8$; $R'_8$ are each independently H, OH, halogen, alkyl, alkenyl, alkoxy, cycloalkyl, heterocycloalkyl, cycloalkenyl, heterocycloalkenyl, aryl, aryloxy, —O—$(CH_2)_q$-aryl, —$(CH_2)_q$-aryl, —C(O)-alkyl, —C(O)-aryl, —C(O)-heteroaryl, —C(O)-cycloalkyl, —C(O)-heterocycloalkyl, —C(O)

O-alkyl, —C(O)O-aryl, —C(O)O-heteroaryl, —C(O)O-cycloalkyl, or C(O)O-heterocycloalkyl, nitro, amino, cyano, nitroso, or azido group, any of which may be optionally substituted; and q is an integer from 1 to 6.

2. The compound of claim 1 having the structure of formula

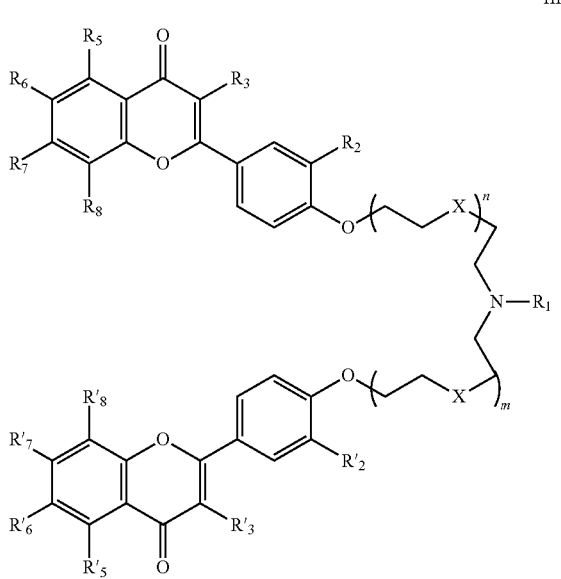

IIIa or a pharmaceutically acceptable salt or solvate thereof;
wherein $R_2$ and $R'_2$ are each independently selected from the group consisting of H, OH, halogen, alkyl, alkoxy, aryloxy, —O—$(CH_2)_q$-aryl, and $(CH_2)_q$-aryl, any of which may be optionally substituted;

n and m are independently an integer ranging between 1 and 4;

X is selected from $CH_2$ or O;

$R_3$; $R'_3$; $R_5$; $R'_5$; $R_6$; $R'_6$; $R_7$; $R'_7$; $R_8$; $R'_8$ are each independently H, OH, halogen, alkyl, alkoxy, aryloxy, —O—$(CH_2)_q$-aryl, —$(CH_2)_q$-aryl, any of which may be optionally substituted; and q is an integer from 1 to 6.

3. The compound of claim 1, or a pharmaceutically acceptable salt or solvate thereof, wherein $R_1$ is selected from the group consisting of H, alkyl, aryl, —$(CH_2)_q$-aryl, —$(CH_2)_q$-heteroaryl, —$(CH_2)_q$-cycloalkyl, —C(O)-alkyl, —C(O)-aryl, —C(O)O-alkyl, —$SO_2$—alkyl, and —$SO_2$-aryl, any of which may be optionally substituted.

4. The compound of claim 1, or a pharmaceutically acceptable salt or solvate thereof, wherein $R_1$ is selected from the group consisting of H, methyl, ethyl, phenyl, —$(CH_2)$-phenyl, —$(CH_2)$-pyridyl, —$(CH_2)$-phthalimidyl, —$(CH_2)$-piridinyl, —$(CH_2)$-naphthyl, —$(CH_2)$-benzimidazolyl, —$(CH_2)$-pyrimidinyl, —$(CH_2)$-quinolinyl, —$(CH_2)$-cyclohexyl, —C(O)-methyl, —C(O)-ethyl, —C(O)-phenyl, —C(O)O-tert-butyl, —$SO_2$- methyl, —$SO_2$-phenyl and $SO_2$-naphthyl, any of which may be optionally substituted.

5. The compound of claim 4, or a pharmaceutically acceptable salt or solvate thereof, wherein the optional substituent of $R_1$ is one or more carboxy, azido, cyano, hydroxyl, nitro, nitroso, $NR_{20}R_{21}$, $CF_3$, $OCF_3$, —C(O)-aryl, —C(O)O-alkyl, alkyl, alkoxy, aryl, aryloxy, heteroaryl, alkenyl, cycloalkyl, heterocycloalkyl, cycloalkenyl, heterocycloalkenyl, or halogen, and $R_{20}$ and $R_{21}$ each independently are H, alkyl or a protecting group.

6. The compound of claim 1, or a pharmaceutically acceptable salt or solvate thereof, wherein $R_1$ is selected from the group consisting of $CH_2CH_3$, $CH_2CH_2$-phthalimido, $CH_2CH_2CH_2$—$C_6H_4$, $CH_2C_6H_5$, $CH_2(2$-F—$C_6H_4)$, $CH_2(3$-F—$C_6H_4)$, $CH_2(4$-$NO_2$—$C_6H_4)$, $CH_2(4$-F—$C_6H_4)$, $CH_2(4$-$CF_3$—$C_6H_4)$, $CH_2(4$-MeO—$C_6H_4)$, $CH_2(4$-$C_6H_5$—$C_6H_4)$, $CH_2(3,4$-F—$C_6H_3)$, $CH_2(3,4,5$-F—$C_6H_2)$, $CH_2(4$-$C_5H_4N)$ and $CH_2(2$-$C_5H_4N)$.

7. The compound of claim 1, or a pharmaceutically acceptable salt or solvate thereof, wherein $R_1$ is selected from the group consisting of $CH_2C_6H_5$, $CH_2(2$-F—$C_6H_4)$, $CH_2(3$-F—$C_6H_4)$, $CH_2(4$-$NO_2$—$C_6H_4)$, $CH_2(4$-F—$C_6H_4)$, $CH_2(4$-$CF_3$—$C_6H_4)$, $CH_2(4$-MeO—$C_6H_4)$, $CH_2(4$-$C_6H_5$—$C_6H_4)$, $CH_2(3,4$-F—$C_6H_3)$, and $CH_2(3,4,5$-F—$C_6H_2)$.

8. The compound of claim 1, or a pharmaceutically acceptable salt or solvate thereof, wherein $R_1$ is selected from the group consisting of $CH_2CH_3$, $CH_2CH_2OH$, $(CH_2)_2CO_2CH_2CH_3$, C(=O)OC($CH_3)_3$, $CH_2C_6H_5$, $CH_2(4$-$NO_2$—$C_6H_4)$, $CH_2(4$-MeOCO—$C_6H_4)$, $CH_2(4$-$C_5H_4N)$, $CH_2(2$-$C_5H_4N)$, C=O($CH_2)_2CO_2H$, $SO_2CH_3$, $SO_2(4$-$CH_3$—$C_6H_4)$, Dansyl and $(CH_2)_3C_6H_5$.

9. The compound of claim 1, or a pharmaceutically acceptable salt or solvate thereof, wherein $R_2$ and $R'_2$ are each independently selected from the group consisting of H, OH, halogen, —O—$(CH_2)$-aryl, C1-6alkyl, and C1-6alkoxy.

10. The compound of claim 4, or a pharmaceutically acceptable salt or solvate thereof, wherein $R_3$; $R'_3$; $R_5$; $R'_5$; $R_6$; $R'_6$; $R_7$; $R'_7$; $R_8$; $R'_8$ are each independently H, OH, halogen, C1-4alkyl, C1-4alkoxy, C6-10aryloxy, —O—$(CH_2)$-aryl, $NO_2$, $NH_2$, $N_3$ or $(CH_2)$-phenyl.

11. The compound of claim 1, or a pharmaceutically acceptable salt or solvate thereof, wherein n, m and q are 1.

12. The compound of claim 4, or a pharmaceutically acceptable salt or solvate thereof, wherein X is O.

13. A method of reducing P-glycoprotein based multidrug resistance comprising the step of administering an effective amount of a compound as defined in claim 1, or a pharmaceutically acceptable salt or solvate thereof.

14. A method of reducing P-glycoprotein based multidrug resistance comprising the step of administering an effective amount of a compound as defined in claim 1, or a pharmaceutically acceptable salt or solvate thereof and an effective amount of an additional agent.

15. A method of treating cancer comprising the step of administering an effective amount of a compound as defined in claim 1, or a pharmaceutically acceptable salt or solvate thereof and an effective amount of an anti-cancer agent.

16. The method of claim 15, wherein the cancer is selected from the group consisting of prostate cancer, leukemia, hormone dependent cancer, breast cancer, colon cancer, lung cancer, epidermal cancer, liver cancer, esophageal cancer, stomach cancer, cancer of the brain, or cancer of the kidney.

17. The method of claim 15, wherein the anti-cancer agent is at least one of Paclitaxel, Doxoribicin, Daunorubicin, Mitoxantrone, Taxol, Docetaxel, Vinblastine, Vincristine, Camptothecin, Topotecan, Etoposide, or Teniposide.

18. A method of inhibiting a parasitic disease comprising the step of administering an effective amount of a compound as defined in claim 1, or a pharmaceutically acceptable salt or solvate thereof.

19. The method of claim 18, wherein the parasitic diseases is caused by genus *Leishmania*.

20. The method of claim 18, wherein the parasitic diseases is caused by one of the parasites selected from the group consisting of *L. donovani, L. amazonensis, L. tarentolae, L. tropica, L. enriettii, L. Mexicana*, and *L. major*.

21. A method of treating a protozoan infection comprising the step of administering an effective amount of a compound as defined in claim 1, or a pharmaceutically acceptable salt or solvate thereof.

22. The method of claim 21, wherein the protozoan infection is selected from the group consisting of malaria, leishmaniasis, Chagas disease, trypanosomiasis, and toxoplasmosis.

23. A pharmaceutical composition comprising an effective amount of a compound as defined in claim 1, or a pharmaceutically acceptable salt or solvate thereof and a pharmaceutically acceptable carrier.

* * * * *